US007144915B2

(12) United States Patent
Byrn et al.

(10) Patent No.: US 7,144,915 B2
(45) Date of Patent: Dec. 5, 2006

(54) **CRYSTALLINE FORMS OF [R-(R*,R*)]-2-(4-FLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID CALCIUM SALT (2:1)**

(75) Inventors: Stephen Robert Byrn, West Lafayette, IN (US); David Andrew Coates, West Lafayette, IN (US); Karen Sue Gushurst, Lafayette, IN (US); Joseph Francis Krzyzaniak, Pawcatuck, CT (US); Zheng Jane Li, Quaker Hill, CT (US); Henry Grant Morrison, II, Lafayette, IN (US); Aeri Park, West Lafayette, IN (US); Petinka Ivanova Vlahova, Lafayette, IN (US)

(73) Assignee: Warner-Lambert Company, LLC, Morris Plains, NJ (US)

( * ) Notice: Subject to any disclaimer, the term of this patent is extended or adjusted under 35 U.S.C. 154(b) by 0 days.

(21) Appl. No.: 10/456,046

(22) Filed: Jun. 6, 2003

(65) Prior Publication Data

US 2004/0054193 A1 Mar. 18, 2004

Related U.S. Application Data

(63) Continuation of application No. 10/184,669, filed on Jun. 28, 2002, now Pat. No. 6,605,729.

(60) Provisional application No. 60/302,049, filed on Jun. 29, 2001.

(51) Int. Cl.
| | |
|---|---|
| *A61K 31/40* | (2006.01) |
| *A61P 3/06* | (2006.01) |
| *A61P 19/10* | (2006.01) |
| *A61P 25/28* | (2006.01) |
| *C07D 207/34* | (2006.01) |

(52) U.S. Cl. .................................................... 514/423
(58) Field of Classification Search ................ 548/537; 514/423
See application file for complete search history.

(56) References Cited

U.S. PATENT DOCUMENTS

| | | | | |
|---|---|---|---|---|
| 5,969,156 A | * | 10/1999 | Briggs et al. | ................ 548/537 |
| 6,121,461 A | * | 9/2000 | McKenzie | .................. 548/530 |
| 6,274,740 B1 | | 8/2001 | Lin et al. | |
| 6,605,636 B1 | * | 8/2003 | Aronhime et al. | .......... 514/423 |
| 2003/0212279 A1 | * | 11/2003 | Tessler et al. | .............. 548/537 |

FOREIGN PATENT DOCUMENTS

| | | |
|---|---|---|
| WO | WO 02/051804 A1 | 9/2000 |
| WO | WO 00/71116 A1 | 11/2000 |
| WO | WO 01/42209 A1 | 6/2001 |
| WO | WO 02/43667 A2 | 6/2002 |
| WO | WO 02/057228 A1 | 7/2002 |
| WO | WO 02/057229 A1 | 7/2002 |
| WO | WO 02/057274 A1 | 7/2002 |
| WO | WO 02/059087 A1 | 8/2002 |
| WO | WO 02/072073 A2 | 9/2002 |
| WO | WO 02/083637 A1 | 10/2002 |
| WO | WO 02/083638 A1 | 10/2002 |
| WO | WO 02/089788 A2 | 11/2002 |

OTHER PUBLICATIONS

Rouhi, Chemical & Engineering News, Feb. 24, 2003, 32-35.*
Cucchiara et al., Journal of the Neurological Sciences, 187, 81-89, 2001.*
Mundy et al., Science, 286, 1946-1949, Dec. 3, 1999.*

* cited by examiner

*Primary Examiner*—Fiona T. Powers
(74) *Attorney, Agent, or Firm*—Francis J. Tinney; Charles W. Ashbrook

(57) ABSTRACT

Novel crystalline forms of [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt designated Form V, Form VI, Form VII, Form VIII, Form IX, Form X, Form XI, Form XII, Form XIII, Form XIV, Form XV, Form XVI, Form XVII, Form XVIII, and Form XIX are characterized by their X-ray powder diffraction, solid-state NMR, and/or Raman spectroscopy are described, as well as methods for the preparation and pharmaceutical composition of the same, which are useful as agents for treating hyperlipidemia, hypercholesterolemia, osteoporosis, and Alzheimer's disease.

46 Claims, 35 Drawing Sheets

CRYSTALLINE FORMS OF [R-(R*,R*)]-2-(4-FLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID CALCIUM SALT (2:1)

This application is a continuation application of U.S. Ser. No. 10/184,669, filed Jun. 28, 2002, now U.S. Pat. No. 6,605,729, which claims benefit of provisional application U.S. Ser. No. 60/302,049, filed Jun. 29, 2001, all of which are incorporated herein by reference in their entirety.

FIELD OF THE INVENTION

The present invention relates to novel crystalline forms of atorvastatin which is known by the chemical name [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt useful as pharmaceutical agents, to methods for their production and isolation, to pharmaceutical compositions which include these compounds and a pharmaceutically acceptable carrier, as well as methods of using such compositions to treat subjects, including human subjects, suffering from hyperlipidemia, hypercholesterolemia, osteoporosis, and Alzheimer's disease.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium, disclosed in U.S. Pat. No. 5,273,995, which is incorporated herein by reference, is currently sold as Lipitor® having the chemical name [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate and the formula

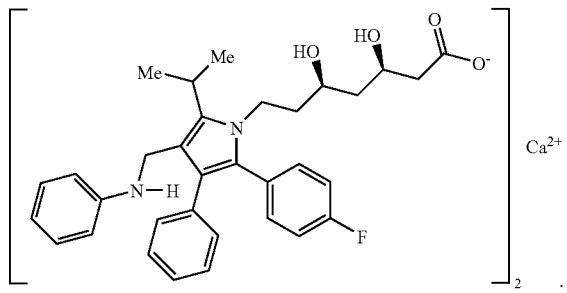

Atorvastatin calcium is a selective, competitive inhibitor of HMG-CoA reductase. As such, atorvastatin calcium is a potent lipid lowering compound and is thus useful as a hypolipidemic and/or hypocholesterolemic agent.

U.S. Pat. No. 4,681,893, which is incorporated herein by reference, discloses certain trans-6-[2-(3- or 4-carboxamido-substituted-pyrrol-1-yl)alkyl]-4-hydroxy-pyran-2-ones including trans (±)-5-(4-fluorophenyl)-2-(1-methylethyl)-N, 4-diphenyl-1-[(2-tetrahydro-4-hydroxy-6-oxo-2H-pyran-2-yl)ethyl]-1H-pyrrole-3-carboxamide.

U.S. Pat. No. 5,273,995, which is herein incorporated by reference, discloses the enantiomer having the R form of the ring-opened acid of trans-5-(4-fluorophenyl)-2-(1-methylethyl)-N, 4-diphenyl-1-[(2-tetrahydro-4-hydroxy-6-oxo-2H-pyran-2-yl)ethyl]-1H-pyrrole-3-carboxamide, ie, [R-(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid which is atorvastatin.

U.S. Pat. Nos. 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,998,633; and 6,087,511, which are herein incorporated by reference, disclose various processes and key intermediates for preparing amorphous atorvastatin. Amorphous atorvastatin has unsuitable filtration and drying characteristics for large-scale production and must be protected from heat, light, oxygen, and moisture.

Crystalline forms of atorvastatin calcium are disclosed in U.S. Pat. Nos. 5,969,156 and 6,121,461 which are herein incorporated by reference.

International Published Patent Application Number WO 01/36384 allegedly discloses a polymorphic form of atorvastatin calcium.

Stable oral formulations of atorvastatin calcium are disclosed in U.S. Pat. Nos. 5,686,104 and 6,126,971.

Atorvastatin is prepared as its calcium salt, ie, [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1). The calcium salt is desirable since it enables atorvastatin to be conveniently formulated in, for example, tablets, capsules, lozenges, powders, and the like for oral administration. Additionally, there is a need to produce atorvastatin in a pure and crystalline form to enable formulations to meet exacting pharmaceutical requirements and specifications.

Furthermore, the process by which atorvastatin is produced needs to be one which is amenable to large-scale production. Additionally, it is desirable that the product should be in a form that is readily filterable and easily dried. Finally, it is economically desirable that the product be stable for extended periods of time without the need for specialized storage conditions.

We have now surprisingly and unexpectedly found novel crystalline forms of atorvastatin. Thus, the present invention provides atorvastatin in new crystalline forms designated Forms V, VI, VII, VIII, IX, X, XI, XII, XIII, XIV, XV, XVI, XVII, XVIII, and XIX. The new crystalline forms of atorvastatin are purer, more stable, or have advantageous manufacturing properties than the amorphous product.

SUMMARY OF THE INVENTION

Accordingly, the present invention is directed to crystalline Form V atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%)[a] |
|---|---|
| 4.9 (broad) | 9 |
| 6.0 | 15 |
| 7.0 | 100 |
| 8.0 (broad) | 20 |
| 8.6 | 57 |
| 9.9 | 22 |
| 16.6 | 42 |
| 19.0 | 27 |
| 21.1 | 35 |

[a]Relative intensity of 4.9 (broad) 2θ is 9.

Additionally, the following X-ray powder diffraction pattern of crystalline Form V atorvastatin expressed in terms of the 2θ values was measured on an Inel (capillary) diffractometer:

| 2θ |
|---|
| 5.0 |
| 6.1 |
| 7.5 |
| 8.4 (broad) |
| 8.7 (broad) |
| 9.9 |
| 16.7 |
| 19.0 |
| 21.2 |

Further, the present invention is directed to crystalline Form V atorvastatin and hydrates thereof characterized by the following solid-state $^{13}$C nuclear magnetic resonance (ssNMR) spectrum wherein chemical shift is expressed in parts per million:

| Assignment | Chemical Shift |
|---|---|
| C12 or C25 | 185.7 |
| C12 or C25 | 176.8 |
| C16 | 166.9 |
| Aromatic Carbons | 138.7 |
| C2–C5, C13–C18, C19–C24, C27–C32 | 136.3 |
|  | 133.0 |
|  | 128.4 |
|  | 122.0 |
|  | 117.0 |
|  | 116.3 |
| C8, C10 | 68.0 |
| Methylene Carbons C6, C7, C9, C11 | 43.1 |
| C33 | 25.6 |
| C34 | 19.9 |

Additionally, the present invention is directed to crystalline Form V atorvastatin and hydrates thereof characterized by the following Raman spectrum having peaks expressed in cm$^{-1}$:

| |
|---|
| 3062 |
| 1652 |
| 1604 |
| 1528 |
| 1478 |
| 1440 |
| 1413 |
| 1397 |
| 1368 |
| 1158 |
| 1034 |
| 1001 |
| 825 |
| 245 |
| 224 |
| 130 |

In a preferred embodiment of the first aspect of the invention, crystalline Form V atorvastatin is a trihydrate.

In a second aspect, the present invention is directed to crystalline Form VI atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%)[a] |
|---|---|
| 7.2 | 11 |
| 8.3 | 77 |
| 11.0 | 20 |
| 12.4 | 11 |
| 13.8 | 9 |
| 16.8 | 14 |
| 18.5 | 100 |
| 19.7 (broad) | 22 |
| 20.9 | 14 |
| 25.0 (broad) | 15 |

[a]Relative intensity of 13.8 (broad) 2θ is 9.

Additionally, the following X-ray powder diffraction pattern of crystalline Form VI atorvastatin expressed in terms of the 2θ values was measured on an Inel (capillary) diffractometer:

| 2θ |
|---|
| 7.3 |
| 8.5 |
| 11.2 |
| 12.7 |
| 14.0 |
| 17.1 (broad) |
| 18.7 |
| 19.9 |
| 21.1 (broad) |
| 25.2 (broad) |

Further, the present invention is directed to crystalline Form VI atorvastatin and hydrates thereof characterized by the following solid-state $^{13}$C nuclear magnetic resonance spectrum wherein chemical shift is expressed in parts per million:

| Assignment | Chemical Shift |
|---|---|
| C12 or C25 | 176.5 |
| C16 or C12 or C25 | 168.2 |
| C16 or C12 or C25 | 163.1 |

-continued

| Assignment | Chemical Shift |
|---|---|
| C16 or C12 or C25 | 159.8 |
| Aromatic Carbons | 136.8 |
| C2–C5, C13–C18, C19–C24, C27–C32 | 127.8 |
|  | 122.3 |
|  | 118.8 |
|  | 113.7 |
| C8, C10 | 88.2 |
| C8, C10 | 79.3 |
|  | 70.5 |
| Methylene Carbons C6, C7, C9, C11 | 43.3 |
|  | 36.9 |
|  | 31.9 |
| C33, C34 | 25.9 |
| C33, C34 | 22.5 |

In a third aspect, the present invention is directed to crystalline Form VII atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%) |
|---|---|
| 8.6 | 76 |
| 10.2 | 70 |
| 12.4 (broad) | 12 |
| 12.8 (broad) | 15 |
| 17.6 | 20 |
| 18.3 (broad) | 43 |
| 19.3 | 100 |
| 22.2 (broad) | 14 |
| 23.4 (broad) | 23 |
| 23.8 (broad) | 26 |
| 25.5 (broad) | 16 |

Additionally, the following X-ray powder diffraction pattern of crystalline Form VII atorvastatin expressed in terms of the 2θ values was measured on an Inel (capillary) diffractometer:

| 2θ |
|---|
| 8.7 |
| 10.2 |
| 12.4 |
| 12.9 |
| 17.6 |
| 18.4 |
| 19.4 |
| 22.2 |
| 23.5 |
| 23.9 |
| 25.6 |

Further, the present invention is directed to crystalline Form VII atorvastatin and hydrates thereof characterized by the following solid-state $^{13}$C nuclear magnetic resonance spectrum wherein chemical shift is expressed in parts per million:

| Assignment | Chemical Shift |
|---|---|
| C12 or C25 | 186.5 |
| C12 or C25 | 183.3 |
| C12 or C25 | 176.8 |
| C16 | 166.5 |
|  | 159.2 |
| Aromatic Carbons | 137.6 |
| C2–C5, C13–C18, C19–C24, C27–C32 | 128.3 |
|  | 122.3 |
|  | 119.2 |
| C8, C10 | 74.5 |
| C8, C10 | 70.3 |
| C8, C10 | 68.3 |
| C8, C10 | 66.2 |
| Methylene Carbons C6, C7, C9, C11 | 43.5 |
|  | 40.3 |
| C33, C34 | 26.3 |
| C33, C34 | 24.9 |
| C33, C34 | 20.2 |

Additionally, the present invention is directed to crystalline Form VII atorvastatin and hydrates thereof characterized by the following Raman spectrum having peaks expressed in cm$^{-1}$:

| Raman Spectrum |
|---|
| 3060 |
| 2927 |
| 1649 |
| 1603 |
| 1524 |
| 1476 |
| 1412 |
| 1397 |
| 1368 |
| 1159 |
| 1034 |
| 998 |
| 824 |
| 114 |

In a preferred embodiment of the third aspect of the invention, crystalline Form VII atorvastatin is a sesquihydrate.

In a fourth aspect, the present invention is directed to crystalline Form VIII atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%)[a] |
|---|---|
| 7.5 | 61 |
| 9.2 | 29 |
| 10.0 | 16 |
| 12.1 | 10 |
| 12.8 | 6 |
| 13.8 | 4 |
| 15.1 | 13 |
| 16.7 (broad) | 64 |
| 18.6 (broad) | 100 |
| 20.3 (broad) | 79 |
| 21.2 | 24 |
| 21.9 | 30 |

| 2θ | Relative Intensity (>10%)[a] |
|---|---|
| 22.4 | 19 |
| 25.8 | 33 |
| 26.5 | 20 |
| 27.4 (broad) | 38 |
| 30.5 | 20 |

[a]Relative intensity of 12.8 2θ is 6 and 13.8 2θ is 4.

Additionally, the following X-ray powder diffraction pattern of crystalline Form VIII atorvastatin expressed in terms of the 2θ values was measured on an Inel (capillary) diffractometer:

| 2θ |
|---|
| 7.5 |
| 9.3 |
| 10.1 |
| 12.2 |
| 12.8 |
| 13.8 |
| 15.1 |
| 16.6–16.9 |
| 18.5–18.9 |
| 20.2–20.6 |
| 21.3 |
| 22.0 |
| 22.5 |
| 25.9 |
| 26.5 |
| 27.4 (broad) |
| 30.6 |

Further, the present invention is directed to crystalline Form VIII atorvastatin and hydrates thereof characterized by the following solid-state $^{13}C$ nuclear magnetic resonance spectrum wherein chemical shift is expressed in parts per million:

| Assignment | Chemical Shift |
|---|---|
| C12 or C25 | 186.1 |
| C12 or C25 | 179.5 |
| C16 | 167.9 |
| C16 | 161.0 |
| Aromatic Carbons | 139.4 |
| C2–C5, C13–C18, C19–C24, C27–C32 | 132.9 |
|  | 128.7 |
|  | 124.7 |
|  | 121.8 |
|  | 116.6 |
| C8, C10 | 67.0 |
| Methylene Carbons C6, C7, C9, C11 | 43.3 |
| C33, C34 | 26.7 |
| C33, C34 | 24.7 |
| C33, C34 | 20.9 |
| C33, C34 | 20.1 |

Additionally, the present invention is directed to crystalline Form VIII atorvastatin and hydrates thereof characterized by the following Raman spectrum having peaks expressed in cm$^{-1}$:

| Raman Spectrum |
|---|
| 3065 |
| 2923 |
| 1658 |
| 1603 |
| 1531 |
| 1510 |
| 1481 |
| 1413 |
| 997 |
| 121 |

In a preferred embodiment of the fourth aspect of the invention, crystalline Form VIII atorvastatin is a dihydrate.

In a fifth aspect, the present invention is directed to crystalline Form IX atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%) |
|---|---|
| 8.8 | 50 |
| 9.4 (broad) | 32 |
| 11.2–11.7 (broad) | 26 |
| 16.7 | 59 |
| 17.5 (broad) | 33 |
| 19.3 (broad) | 55 |
| 21.4 (broad) | 100 |
| 22.4 (broad) | 33 |
| 23.2 (broad) | 63 |
| 29.0 (broad) | 15 |

Additionally, the following X-ray powder diffraction pattern of crystalline Form IX atorvastatin expressed in terms of the 2θ values was measured on an Inel (capillary) diffractometer:

| 2θ |
|---|
| 9.0 |
| 9.4 |
| 10.0–10.5 (broad) |
| 11.8–12.0 (broad) |
| 16.9 |
| 17.5 (broad) |
| 19.4 (broad) |
| 21.6 (broad) |
| 22.6 (broad) |
| 23.2 (broad) |
| 29.4 (broad) |

In a sixth aspect, the present invention is directed to crystalline Form X atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%) |
|---|---|
| 4.7 | 35 |
| 5.2 | 24 |
| 5.8 | 11 |
| 6.9 | 13 |
| 7.9 | 53 |
| 9.2 | 56 |
| 9.5 | 50 |
| 10.3 (broad) | 13 |
| 11.8 | 20 |
| 16.1 | 13 |
| 16.9 | 39 |
| 19.1 | 100 |
| 19.8 | 71 |
| 21.4 | 49 |
| 22.3 (broad) | 36 |
| 23.7 (broad) | 37 |
| 24.4 | 15 |
| 28.7 | 31 |

Additionally, the following X-ray powder diffraction pattern of crystalline Form X atorvastatin expressed in terms of the 2θ values was measured on an Inel (capillary) diffractometer:

| 2θ |
|---|
| 4.7 |
| 5.2 |
| 5.8 |
| 6.9 |
| 7.9 |
| 9.2 |
| 9.6 |
| 10.2–10.4 |
| 11.9 |
| 16.2 |
| 16.9 |
| 19.1 |
| 19.9 |
| 21.5 |
| 22.3–22.6 |
| 23.7–24.0 (broad) |
| 24.5 |
| 28.8 |

Further, the present invention is directed to crystalline Form X atorvastatin and hydrates thereof characterized by the following solid-state $^{13}$C nuclear magnetic resonance spectrum wherein chemical shift is expressed in parts per million:

| Assignment | Chemical Shift |
|---|---|
| C12 or C25 | 187.0 |
| C12 or C25 | 179.5 |
| C16 | 165.5 |
| C16 | 159.4 |
| Aromatic Carbons | 137.9 |
| C2–C5, C13–C18, | 134.8 |
| C19–C24, C27–C32 | 129.4 |
|  | 127.9 |
|  | 123.2 |
|  | 119.9 |
| C8, C10 | 71.1 |
| Methylene Carbons | 43.7 |
| C6, C7, C9, C11 | 40.9 |

| Assignment | Chemical Shift |
|---|---|
| C33 | 26.4 |
|  | 25.3 |
| C34 | 20.3 |
|  | 18.3 |

Additionally, the present invention is directed crystalline Form X atorvastatin and hydrates thereof characterized by the following Raman spectrum having peaks expressed in cm$^{-1}$:

| Raman Spectrum |
|---|
| 3062 |
| 2911 |
| 1650 |
| 1603 |
| 1525 |
| 1478 |
| 1411 |
| 1369 |
| 1240 |
| 1158 |
| 1034 |
| 999 |
| 824 |
| 116 |

In a preferred embodiment of the sixth aspect of the invention, crystalline Form X atorvastatin is a trihydrate.

In a seventh aspect, the present invention is directed to crystalline Form XI atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%) |
|---|---|
| 10.8 (broad) | 58 |
| 12.0 | 12 |
| 13.5 | 11 |
| 16.5 | 52 |
| 17.6–18.0 (broad) | 35 |
| 19.7 | 82 |
| 22.3 | 100 |
| 23.2 | 26 |
| 24.4 | 28 |
| 25.8 | 17 |
| 26.5 | 30 |
| 27.3 | 31 |
| 28.7 | 19 |
| 29.5 | 12 |
| 30.9 (broad) | 17 |
| 32.8 (broad) | 11 |
| 33.6 (broad) | 15 |
| 36.0 (broad) | 15 |
| 38.5 (broad) | 14 |

In an eighth aspect, the present invention is directed to crystalline Form XII atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%)[a] |
|---|---|
| 5.4 | 11 |
| 7.7 | 24 |
| 8.0 | 25 |
| 8.6 | 42 |
| 8.9 | 25 |
| 9.9 | 36 |
| 10.4 (broad) | 24 |
| 12.5 | 18 |
| 13.9 (broad) | 9 |
| 16.2 | 10 |
| 17.8 | 70 |
| 19.4 | 100 |
| 20.8 | 51 |
| 21.7 | 13 |
| 22.4–22.6 (broad) | 18 |
| 24.3 | 19 |
| 25.5 | 24 |
| 26.2 | 11 |
| 27.1 | 8 |

[a] Relative intensity of 13.9 (broad) 2θ is 9 and 27.1 2θ is 8.

Additionally, the following X-ray powder diffraction pattern of crystalline Form XII atorvastatin expressed in terms of the 2θ values was measured on an Inel (capillary) diffractometer:

| 2θ |
|---|
| 5.4 |
| 7.7 |
| 8.1 |
| 8.6 |
| 8.9 |
| 10.0 |
| 10.5 |
| 12.6 |
| 14.0 (broad) |
| 16.2 |
| 17.9 |
| 19.4 |
| 20.9 |
| 21.8 |
| 22.5–22.8 (broad) |
| 24.4 |
| 25.6 |
| 26.4 |
| 27.2 |

Additionally, the present invention is directed crystalline Form XII atorvastatin and hydrates thereof characterized by the following Raman spectrum having peaks expressed in cm$^{-1}$:

| Raman Spectrum |
|---|
| 3064 |
| 2973 |
| 2926 |
| 1652 |
| 1603 |
| 1527 |
| 1470 |
| 1410 |
| 1367 |
| 1240 |
| 1159 |
| 1034 |
| 1002 |
| 823 |

In a ninth aspect, the present invention is directed to crystalline Form XIII atorvastatin and hydrates thereof characterized by the following X-ray powder diffraction pattern expressed in terms of the 2θ and relative intensities with a relative intensity of >10% measured on a Shimadzu diffractometer with CuK$_\alpha$ radiation:

| 2θ | Relative Intensity (>10%) |
|---|---|
| 8.4 | 100 |
| 8.9 | 82 |
| 15.7 (broad) | 45 |
| 16.4 (broad) | 46 |
| 17.6 (broad) | 57 |
| 18.1 (broad) | 62 |
| 19.7 (broad) | 58 |
| 20.8 (broad) | 91 |
| 23.8 (broad | 57 |

In a tenth aspect, the present invention is directed to crystalline Form XIV atorvastatin and hydrates thereof characterized by the following X-ray powder diffraction pattern expressed in terms of the 2θ and relative intensities with a relative intensity of >10% measured on a Bruker D5000 diffractometer with CuK$_\alpha$ radiation:

| 2θ | Relative Intensity (>10%) |
|---|---|
| 5.4 | 41 |
| 6.7 | 31 |
| 7.7 | 100 |
| 8.1 | 35 |
| 9.0 | 65 |
| 16.5 (broad) | 15 |
| 17.6 (broad) | 17 |
| 18.0–18.7 (broad) | 21 |
| 19.5 (broad) | 18 |

In an eleventh aspect, the present invention is directed to crystalline Form XV atorvastatin and hydrates thereof characterized by the following X-ray powder diffraction pattern expressed in terms of the 2θ and relative intensities with a relative intensity of >10% measured on a Bruker D5000 diffractometer with CuK$_\alpha$ radiation:

| 2θ | Relative Intensity (>10%) |
|---|---|
| 5.7 | 26 |
| 6.1 | 21 |
| 6.8 | 18 |
| 7.5 | 39 |
| 8.1 | 39 |
| 8.5 | 42 |
| 9.5 | 33 |

-continued

| 2θ | Relative Intensity (>10%) |
|---|---|
| 10.5 (broad) | 18 |
| 19.1–19.6 (broad) | 32 |

In a twelfth aspect, the present invention is directed to crystalline Form XVI atorvastatin and hydrates thereof characterized by the following X-ray powder diffraction pattern expressed in terms of the 2θ and relative intensities with a relative intensity of >10% measured on a Bruker D5000 diffractometer with CuK$_\alpha$ radiation:

| 2θ | Relative Intensity (>10%) |
|---|---|
| 5.2 | 37 |
| 6.4 | 34 |
| 7.5 | 100 |
| 8.7 | 79 |
| 10.5 (broad) | 19 |
| 12.0 (broad) | 10 |
| 12.7 (broad) | 17 |
| 16.7 | 26 |
| 18.3 (broad) | 27 |
| 19.5 | 23 |
| 20.1–20.4 (broad) | 37 |
| 21.2–21.9 (broad) | 32 |
| 22.9–23.3 (broad) | 38 |
| 24.4–25.0 (broad) | 35 |

Additionally, the following X-ray powder diffraction pattern of crystalline Form XVI atorvastatin expressed in terms of the 2θ values was measured on a Shimadzu diffractometer with CuK$_\alpha$ radiation:

| 2θ |
|---|
| 7.6 |
| 8.8 |
| 10.2 |
| 12.5 |
| 16.8 |
| 18.2 |
| 19.3 |
| 20.5 |
| 23.0 |
| 24.8 |

In addition, the following X-ray powder diffraction pattern of crystalline Form XVI atorvastatin expressed in terms of the 2θ values was measured on an Inel (capillary) diffractometer:

| 2θ |
|---|
| 5.1 |
| 6.2 |
| 7.3 |
| 8.7 |
| 10.2 (broad) |
| 12.0 (broad) |
| 12.7 (broad) |
| 16.7 |
| 18.0 (broad) |
| 19.5 (broad) |

-continued

| 2θ |
|---|
| 20.0–20.5 (broad) |
| 21.5–21.6 (broad) |
| 22.9–23.3 (broad) |
| 24.0–25.0 (broad) |

In a thirteenth aspect, the present invention is directed to crystalline Form XVII atorvastatin and hydrates thereof characterized by the following X-ray powder diffraction pattern expressed in terms of the 2θ and relative intensities with a relative intensity of >10% measured on a Bruker D5000 diffractometer with CuK$_\alpha$ radiation:

| 2θ | Relative Intensity (>10%) |
|---|---|
| 5.0 | 27 |
| 6.1 | 33 |
| 7.3 | 100 |
| 7.9 | 30 |
| 8.5 | 29 |
| 9.1 | 22 |
| 10.0 | 45 |
| 12.1 (broad) | 24 |
| 14.8 | 17 |
| 16.0–16.5 (broad) | 20 |
| 17.5 (broad) | 28 |
| 19.0 (broad) | 46 |
| 19.5 | 65 |
| 20.2 (broad) | 47 |
| 21.3 | 64 |
| 21.6 | 55 |
| 22.0 | 45 |

In a fourteenth aspect, the present invention is directed to crystalline Form XVIII atorvastatin and hydrates thereof characterized by the following X-ray powder diffraction pattern expressed in terms of the 2θ and relative intensities with a relative intensity of >10% measured on a Bruker D5000 diffractometer with CuK$_\alpha$ radiation:

| 2θ | Relative Intensity (>10%) |
|---|---|
| 8.0 | 100 |
| 9.2 (broad) | 52 |
| 9.7 (broad) | 40 |
| 12.1 | 24 |
| 16.6 (broad) | 48 |
| 18.5 | 67 |

Additionally, the following X-ray powder diffraction pattern of crystalline Form XVIII atorvastatin expressed in terms of the 2θ values was measured on a Shimadzu diffractometer with CuK$_\alpha$ radiation:

| 2θ |
|---|
| 7.7 |
| 9.3 |
| 9.9 |
| 12.2 |
| 16.8 |
| 18.5 |

In addition, the following X-ray powder diffraction pattern of crystalline Form XVIII atorvastatin expressed in terms of the 2θ values was measured on an Inel (capillary) diffractometer:

| 2θ |
|---|
| 7.9 |
| 9.2 (broad) |
| 9.8 (broad) |
| 12.2 (broad) |
| 16.7 (broad) |
| 18.5 |

In a fifteenth aspect, the present invention is directed to crystalline Form XIX atorvastatin and hydrates thereof characterized by the following X-ray powder diffraction pattern expressed in terms of the 2θ and relative intensities with a relative intensity of >10% measured on a Bruker D5000 diffractometer with CuK$_\alpha$ radiation:

| 2θ | Relative Intensity (>10%) |
|---|---|
| 5.2 | 32 |
| 6.3 | 28 |
| 7.0 | 100 |
| 8.6 | 74 |
| 10.5 | 34 |
| 11.6 (broad) | 26 |
| 12.7 (broad) | 35 |
| 14.0 | 15 |
| 16.7 (broad) | 30 |
| 18.9 | 86 |
| 20.8 | 94 |
| 23.6 (broad) | 38 |
| 25.5 (broad) | 32 |

As inhibitors of HMG-CoA reductase, the novel crystalline forms of atorvastatin are useful hypolipidemic and hypocholesterolemic agents as well as agents in the treatment of osteoporosis and Alzheimer's disease.

A still further embodiment of the present invention is a pharmaceutical composition for administering an effective amount of crystalline Form V, Form VI, Form VII, Form VIII, Form IX, Form X, Form XI, Form XII, Form XIII, Form XIV, Form XV, Form XVI, Form XVII, Form XVIII, or Form XIX atorvastatin in unit dosage form in the treatment methods mentioned above. Finally, the present invention is directed to methods for production of Form V, Form VI, Form VII, Form VIII, Form IX, Form X, Form XI, Form XII, Form XIII, Form XIV, Form XV, Form XVI, Form XVII, Form XVIII, or Form XIX atorvastatin.

BRIEF DESCRIPTION OF THE DRAWINGS

The invention is further described by the following non-limiting examples which refer to the accompanying FIGS. 1 to 35, short particulars of which are given below.

Figure 1:
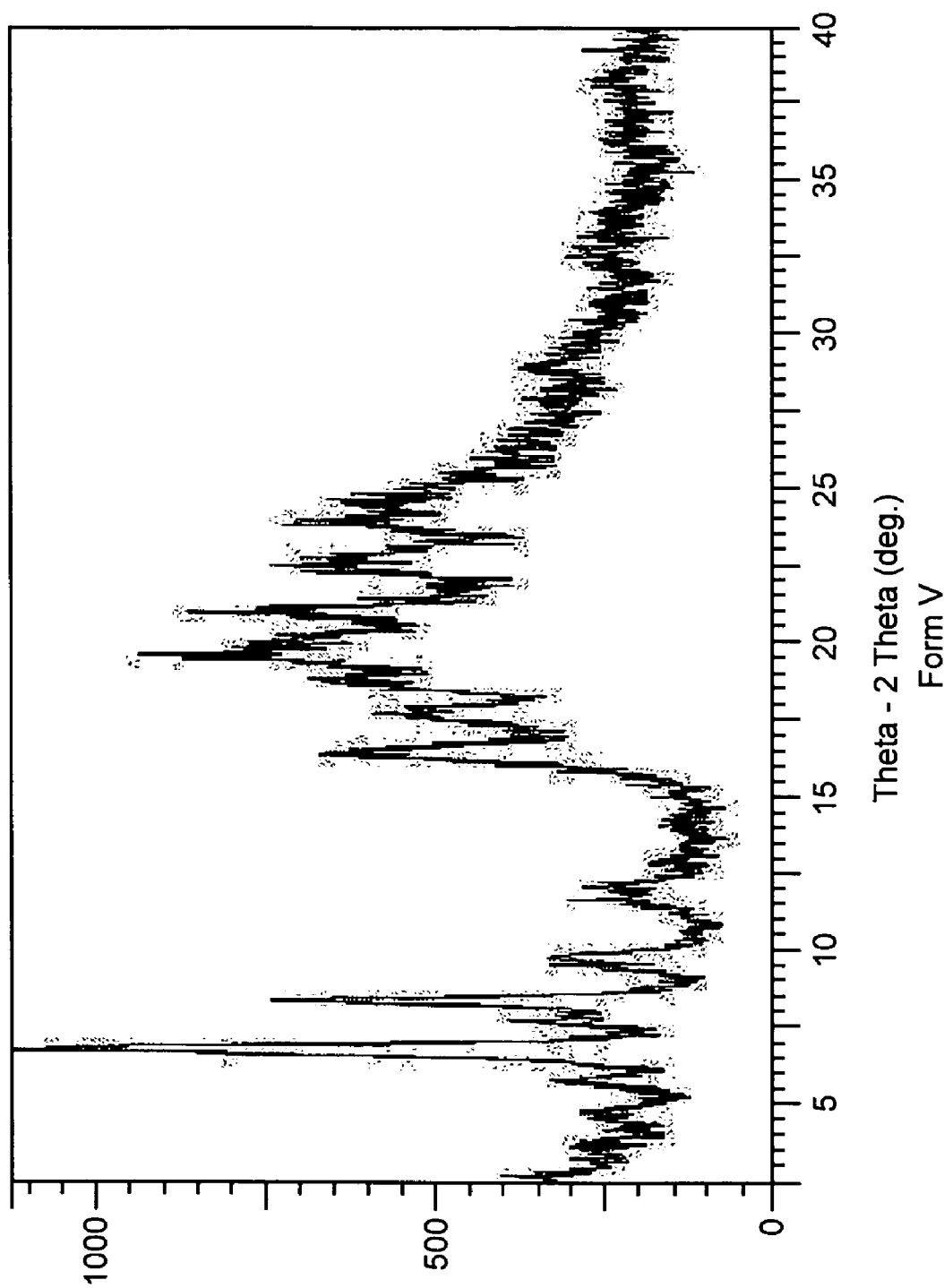
FIG. 1
Diffractogram of Form V atorvastatin carried out on Shimadzu XRD-6000 diffractometer.
Figure 2:
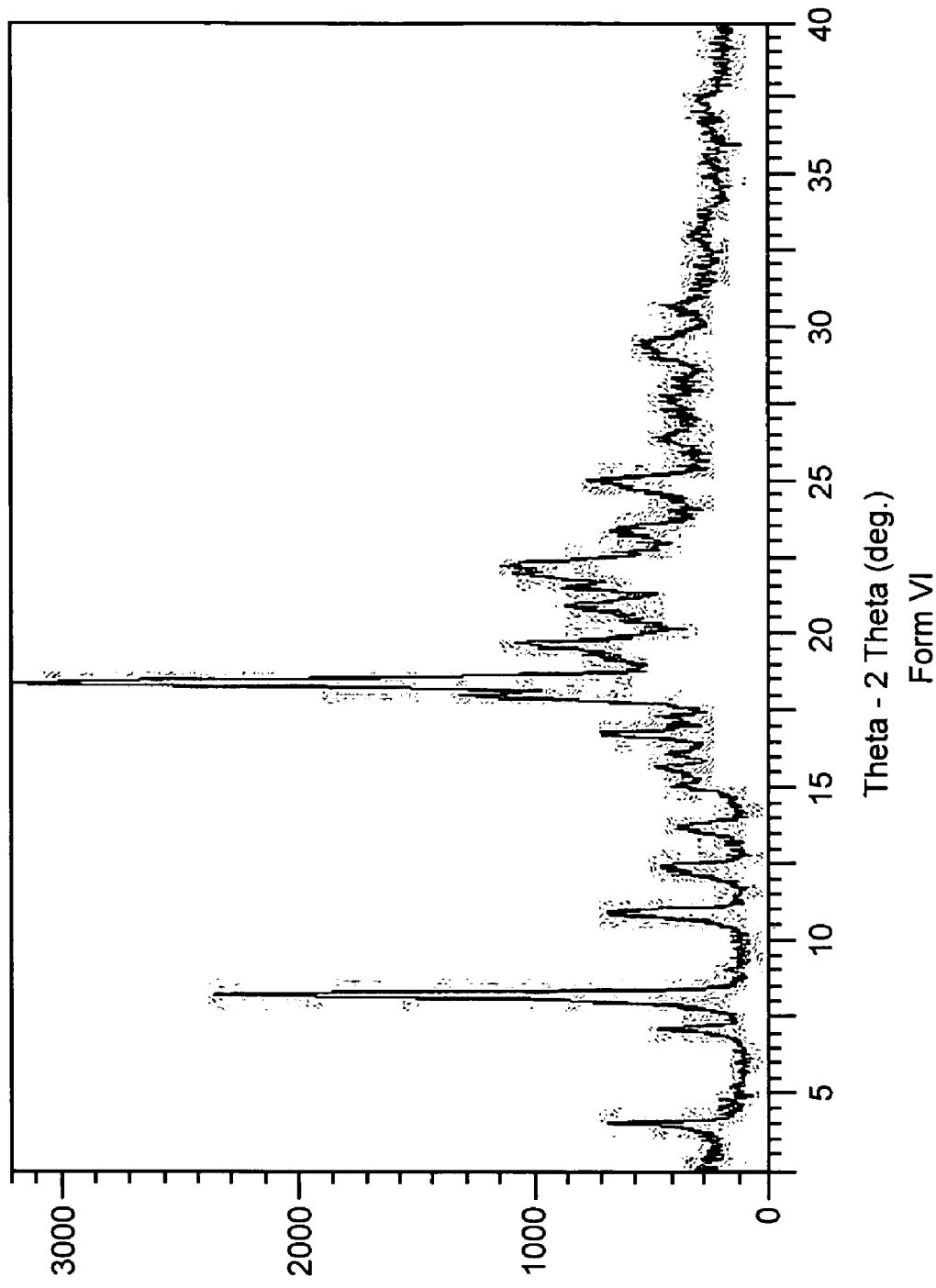
FIG. 2
Diffractogram of Form VI atorvastatin carried out on Shimadzu XRD-6000 diffractometer.
Figure 3:
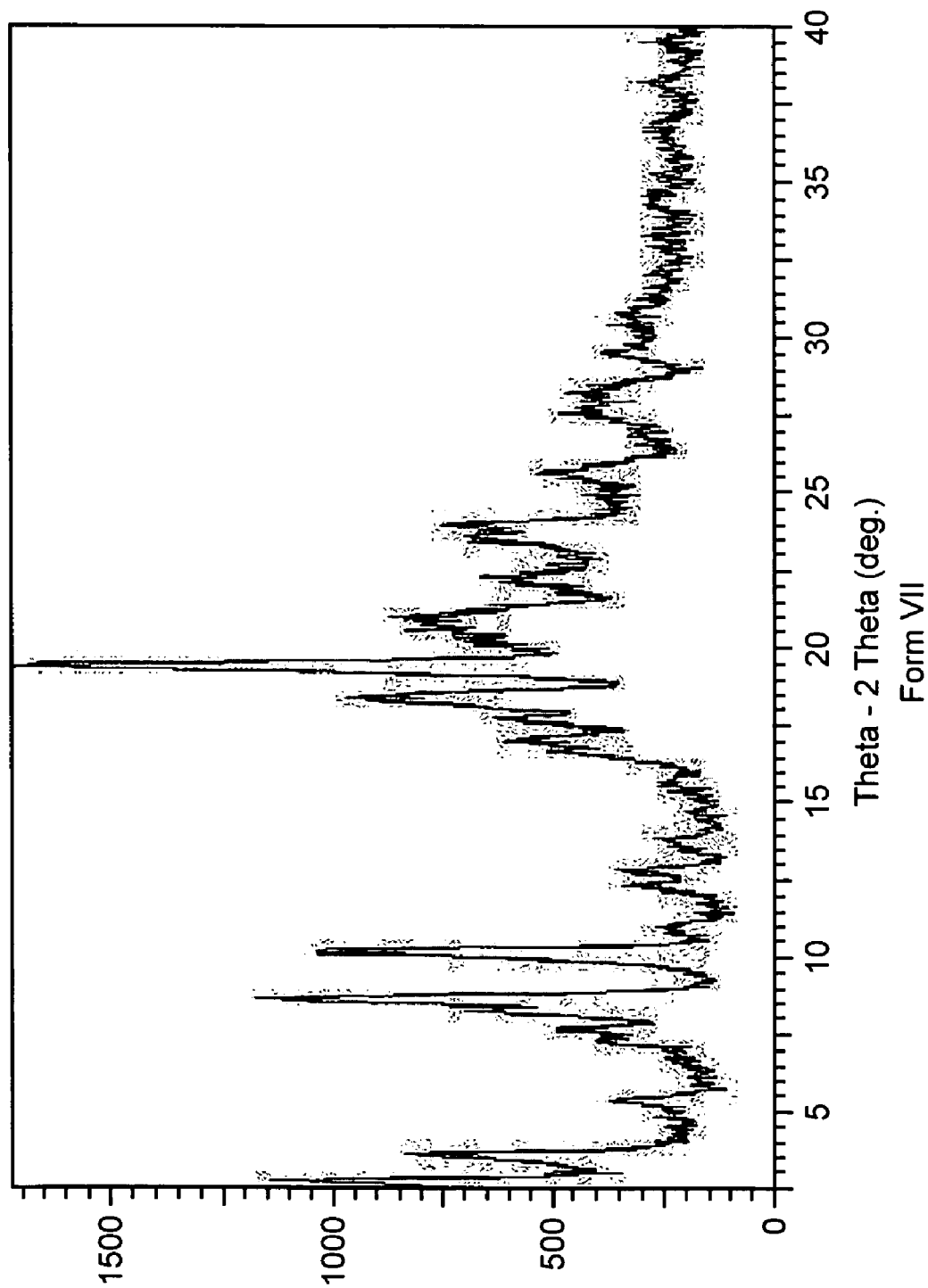
FIG. 3
Diffractogram of Form VII atorvastatin carried out on Shimadzu XRD-6000 diffractometer.
Figure 4:
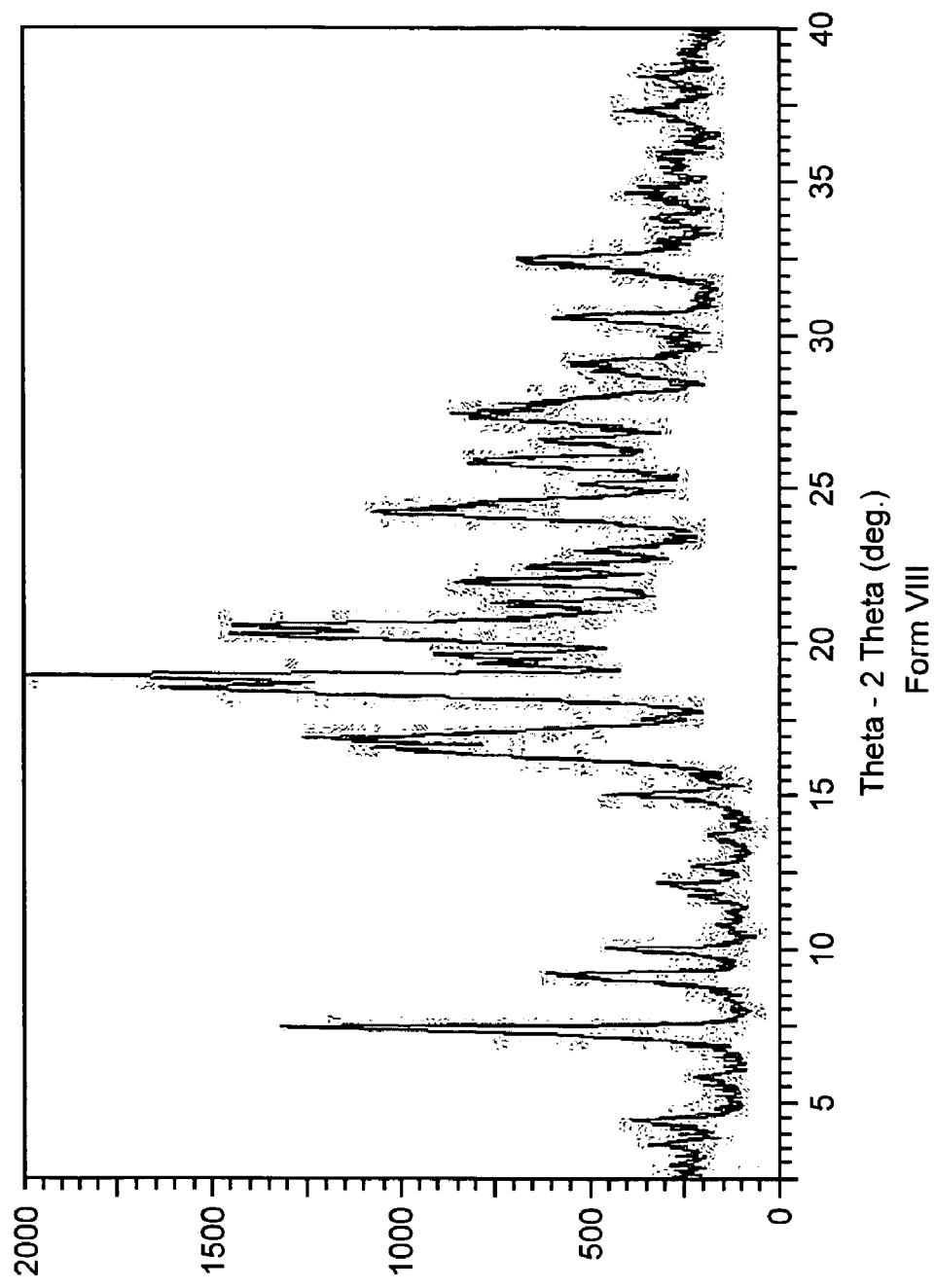
FIG. 4
Diffractogram of Form VIII atorvastatin carried out on Shimadzu XRD-6000 diffractometer.
Figure 5:
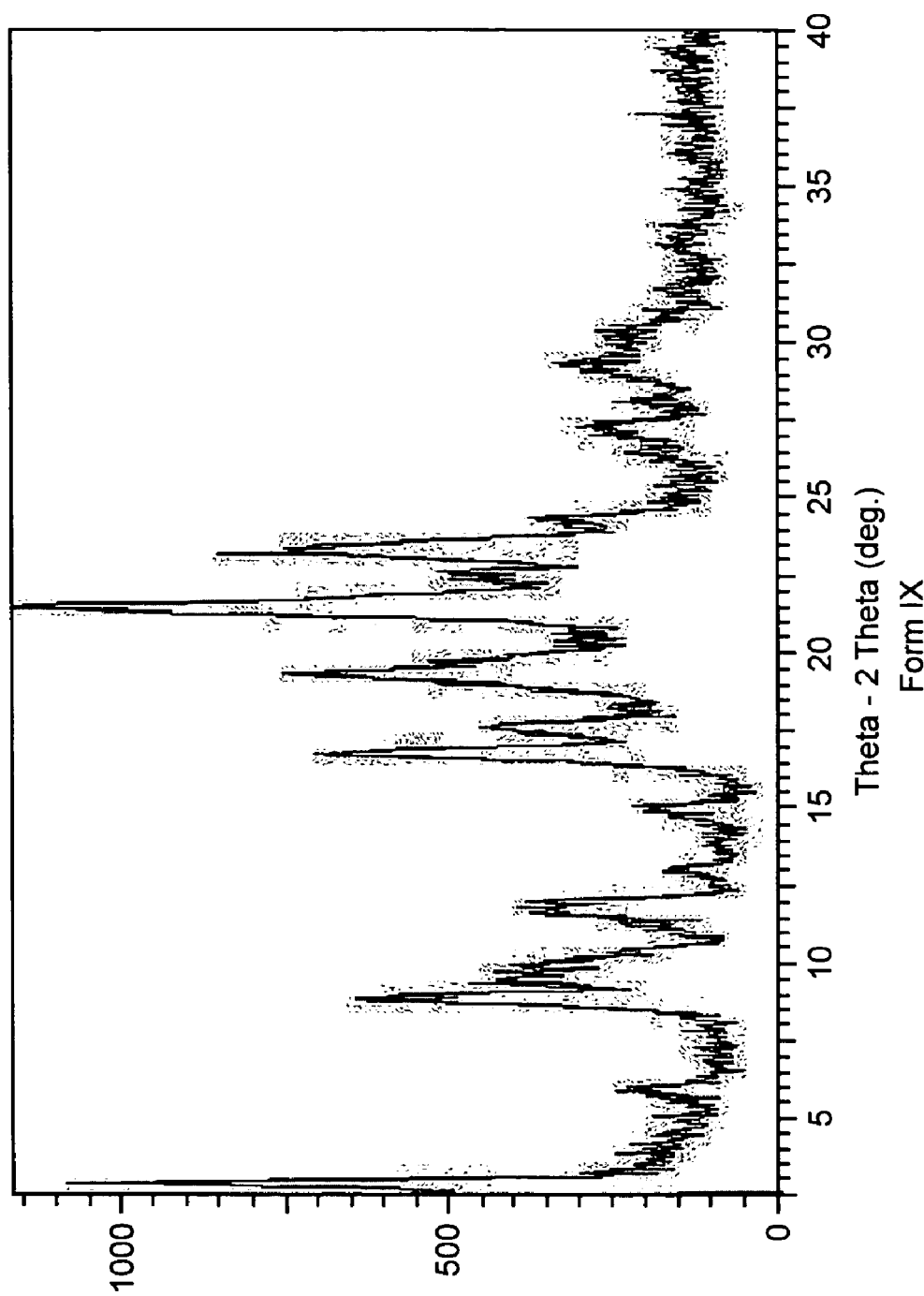
FIG. 5
Diffractogram of Form IX atorvastatin carried out on Shimadzu XRD-6000 diffractometer.
Figure 6:
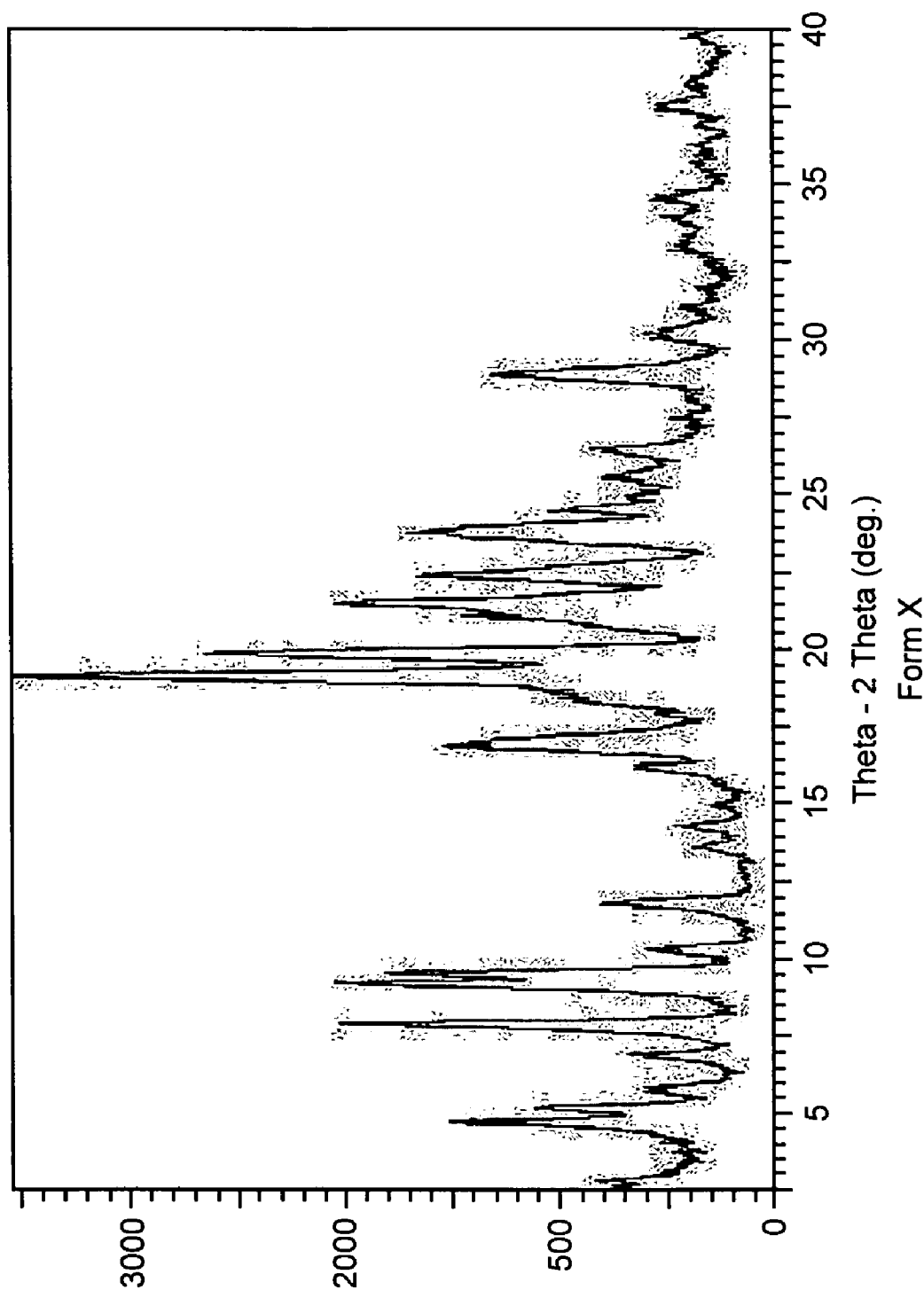
FIG. 6
Diffractogram of Form X atorvastatin carried out on Shimadzu XRD-6000 diffractometer.
Figure 7:
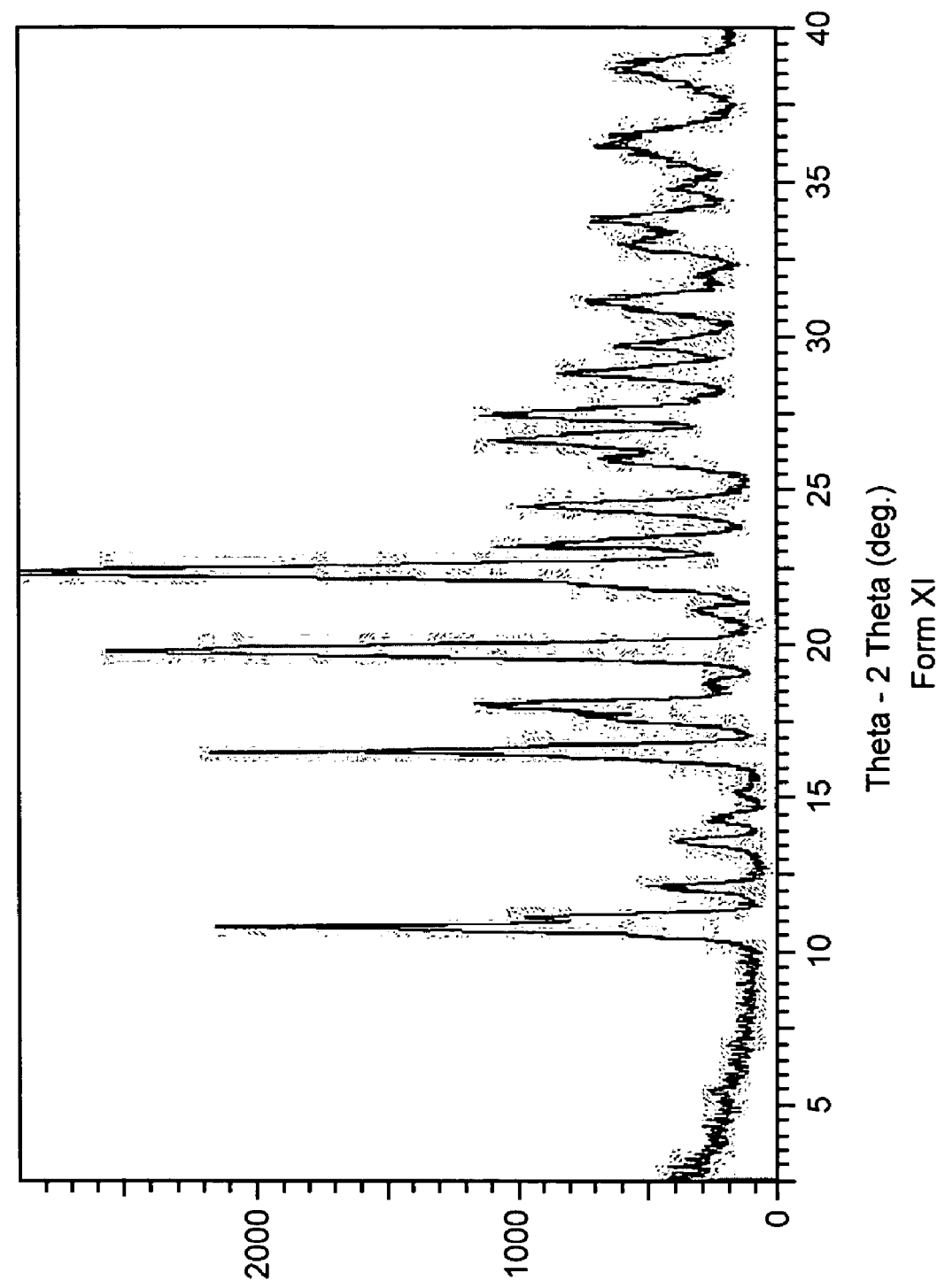
FIG. 7
Diffractogram of Form XI atorvastatin carried out on Shimadzu XRD-6000 diffractometer.
Figure 8:
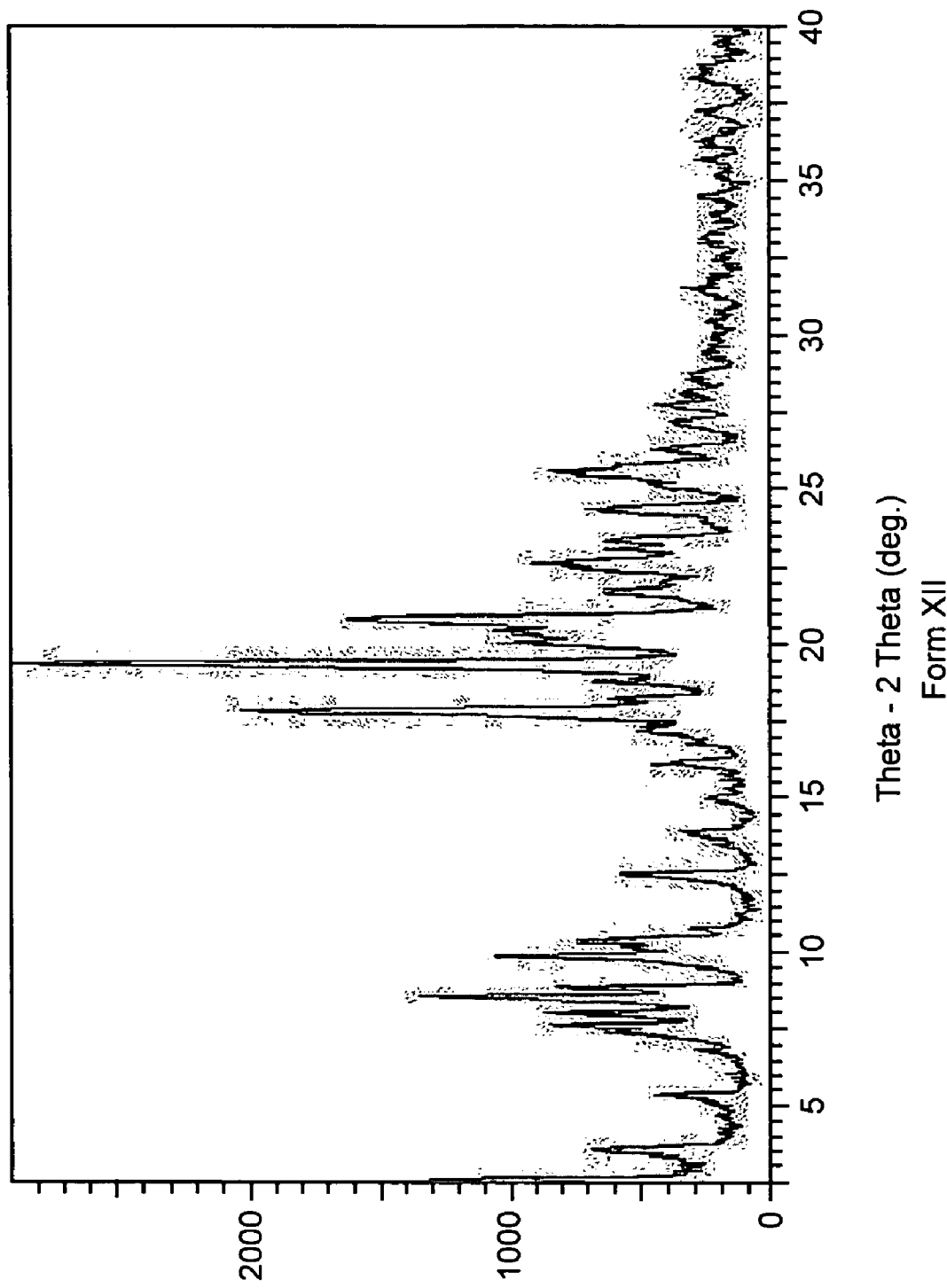
FIG. 8
Diffractogram of Form XII atorvastatin carried out on Shimadzu XRD-6000 diffractometer.
Figure 9:
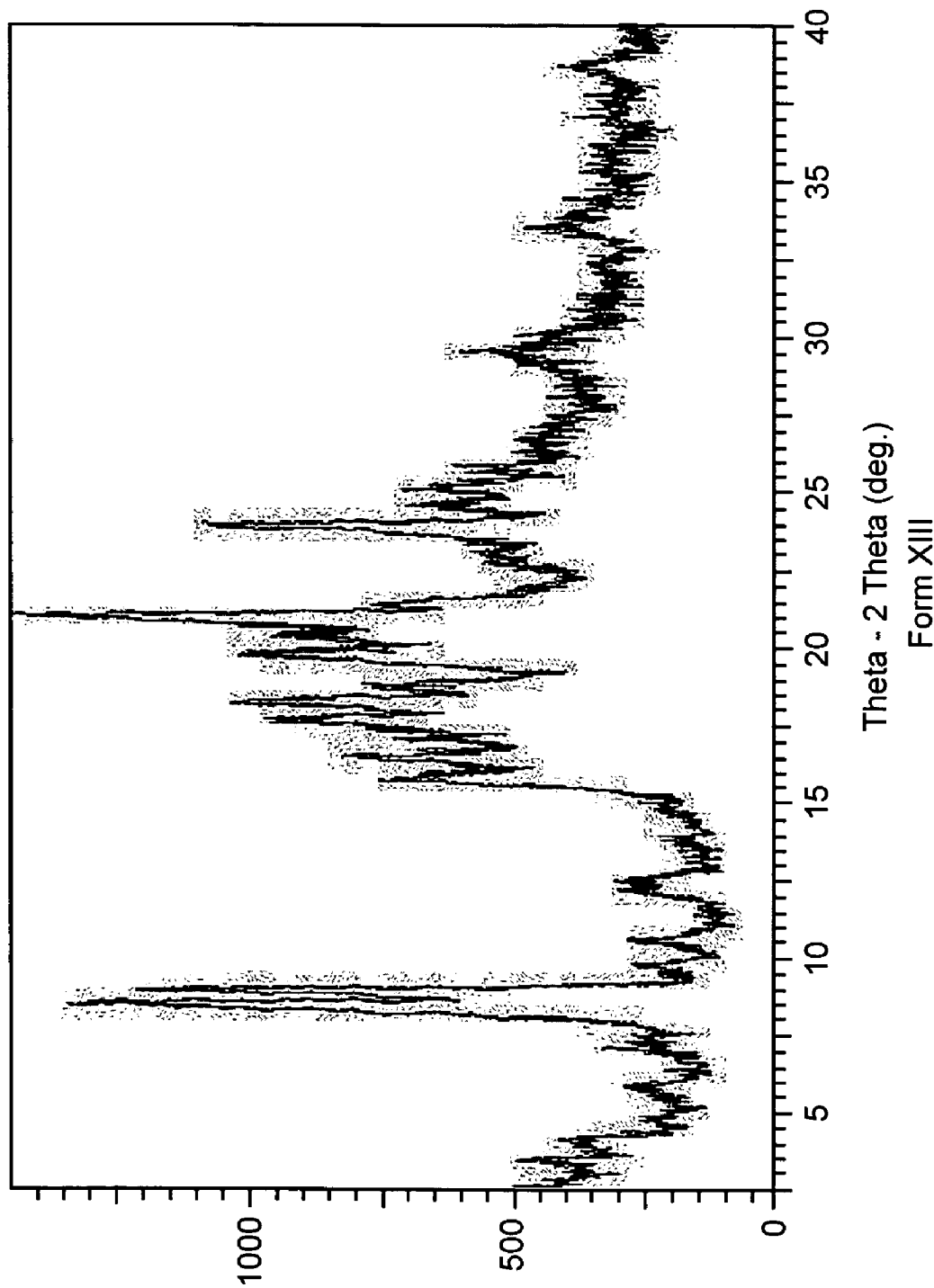
FIG. 9
Diffractogram of Form XIII atorvastatin carried out on Shimadzu XRD-6000 diffractometer.
Figure 10:
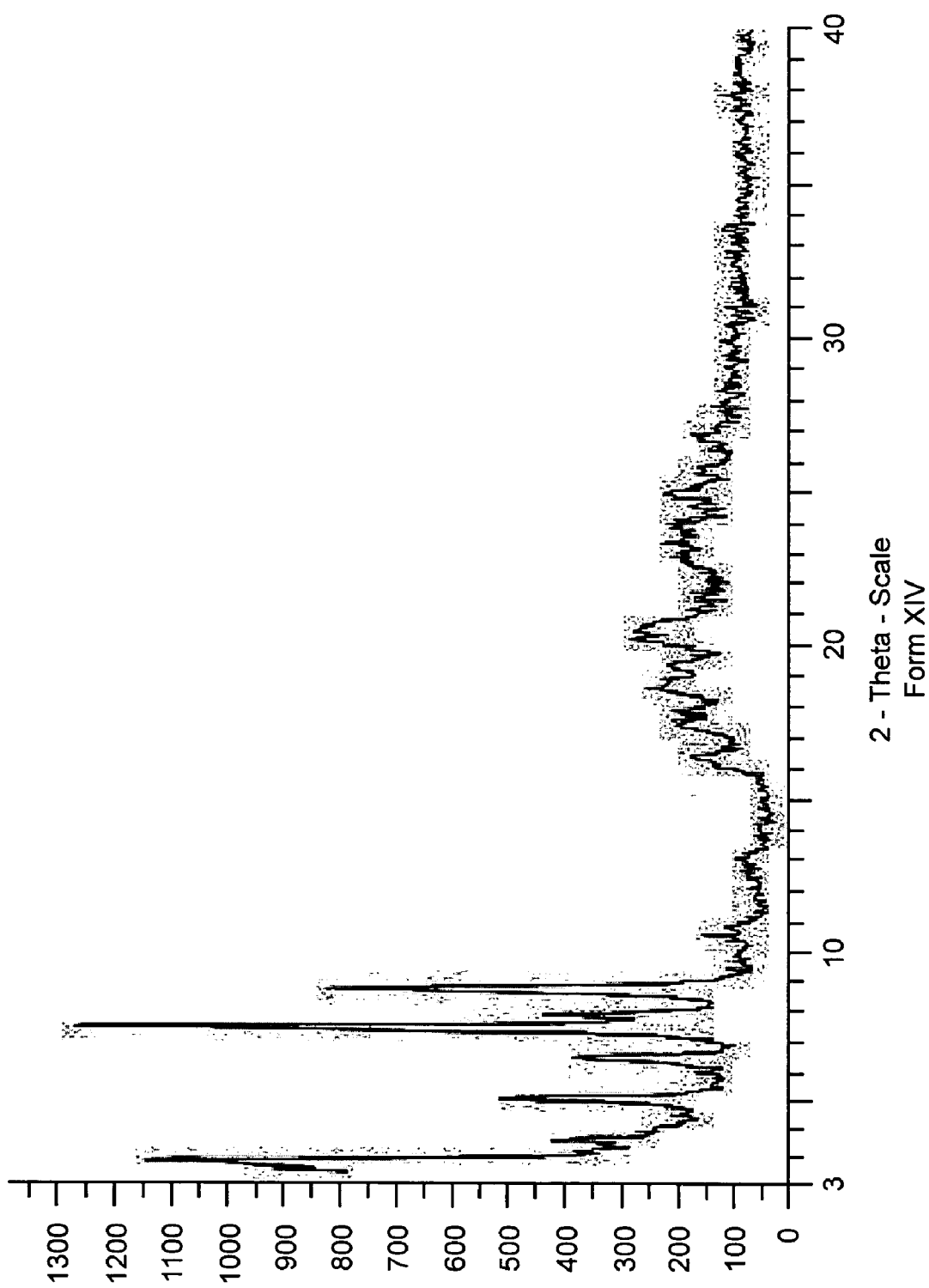
FIG. 10
Diffractogram of Form XIV atorvastatin carried out on Bruker D 5000 diffractometer.
Figure 11:
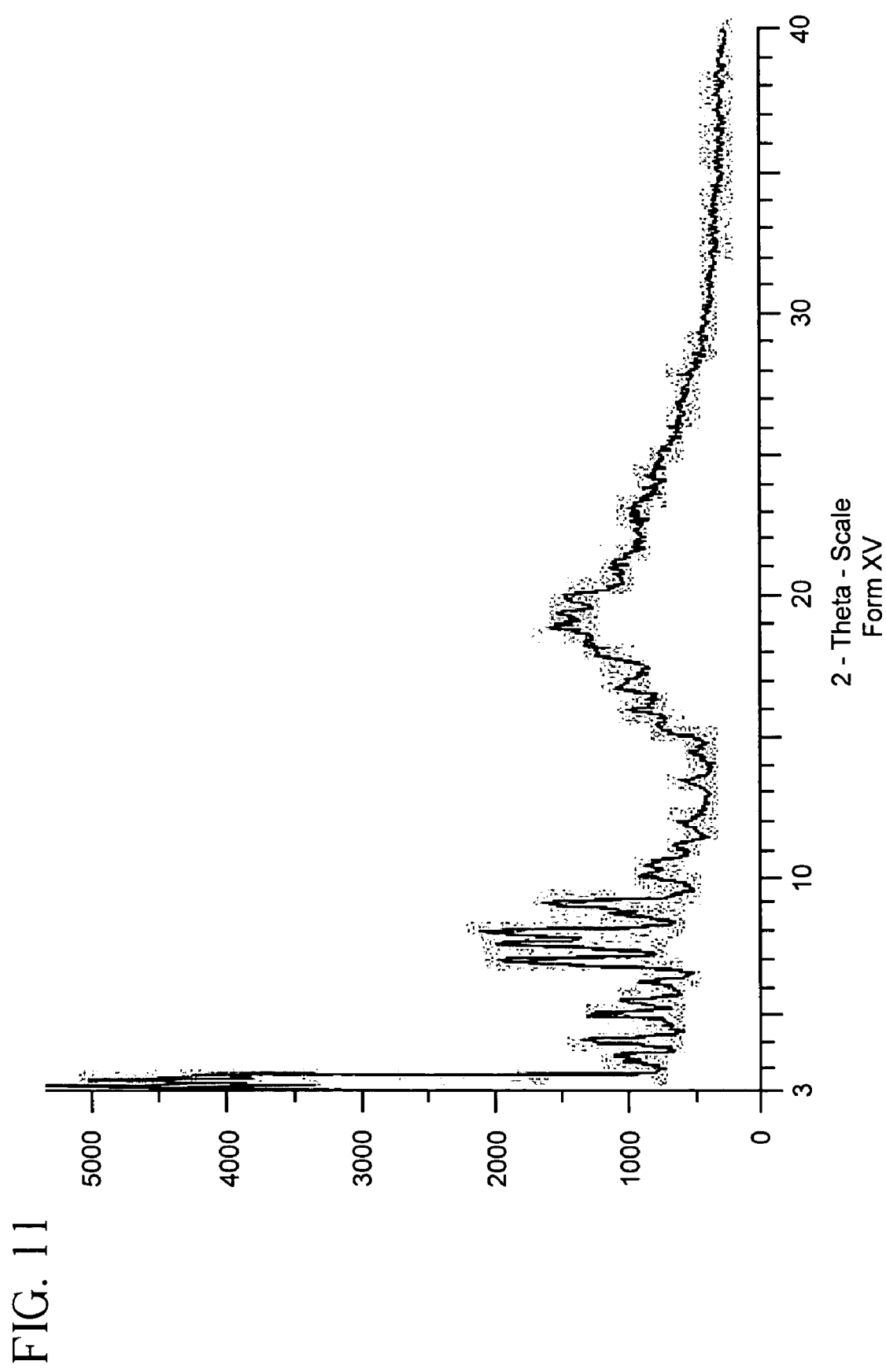
FIG. 11
Diffractogram of Form XV atorvastatin carried out on Bruker D 5000 diffractometer.
Figure 12:
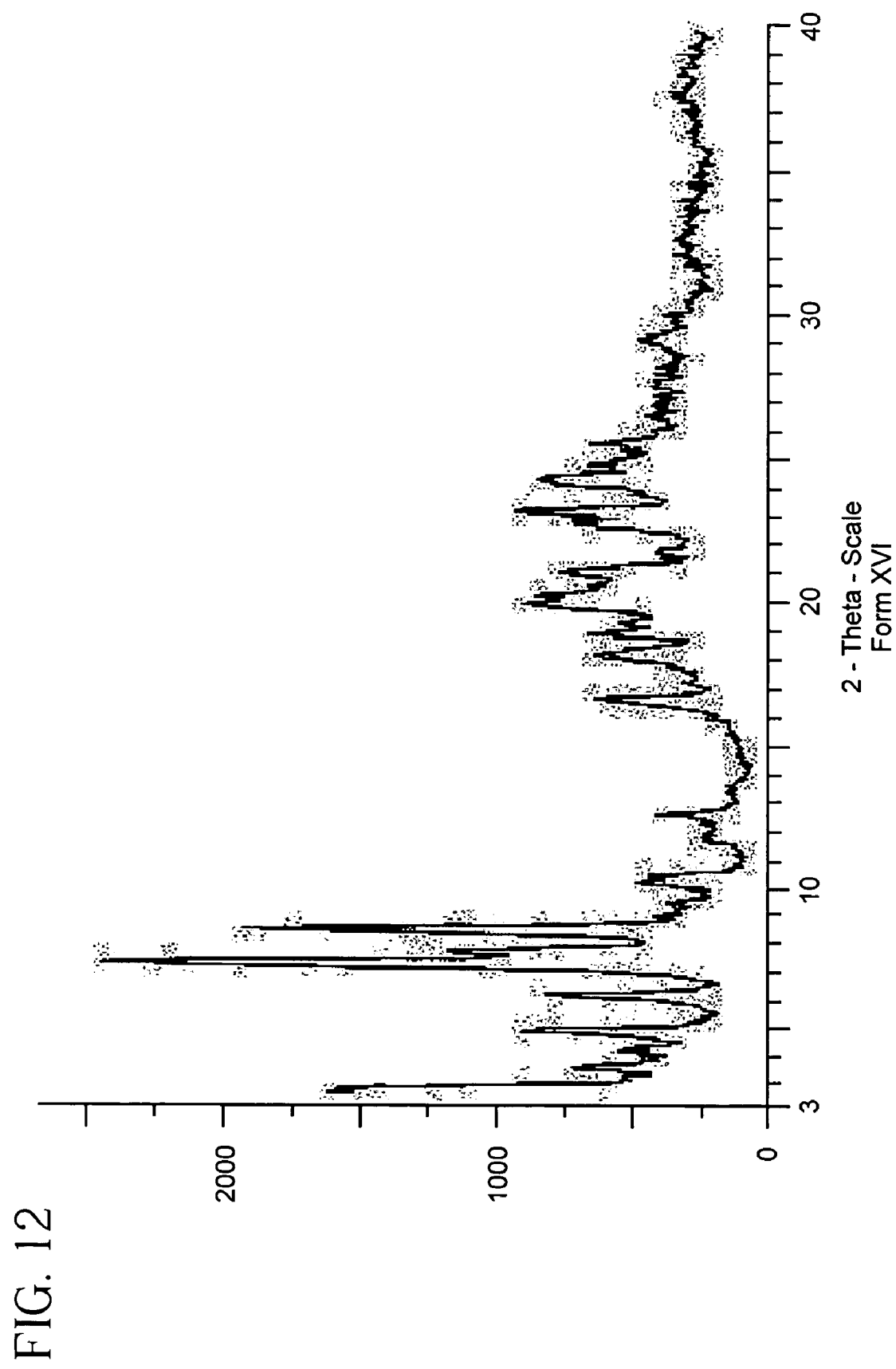
FIG. 12
Diffractogram of Form XVI atorvastatin carried out on Bruker D 5000 diffractometer.
Figure 13:
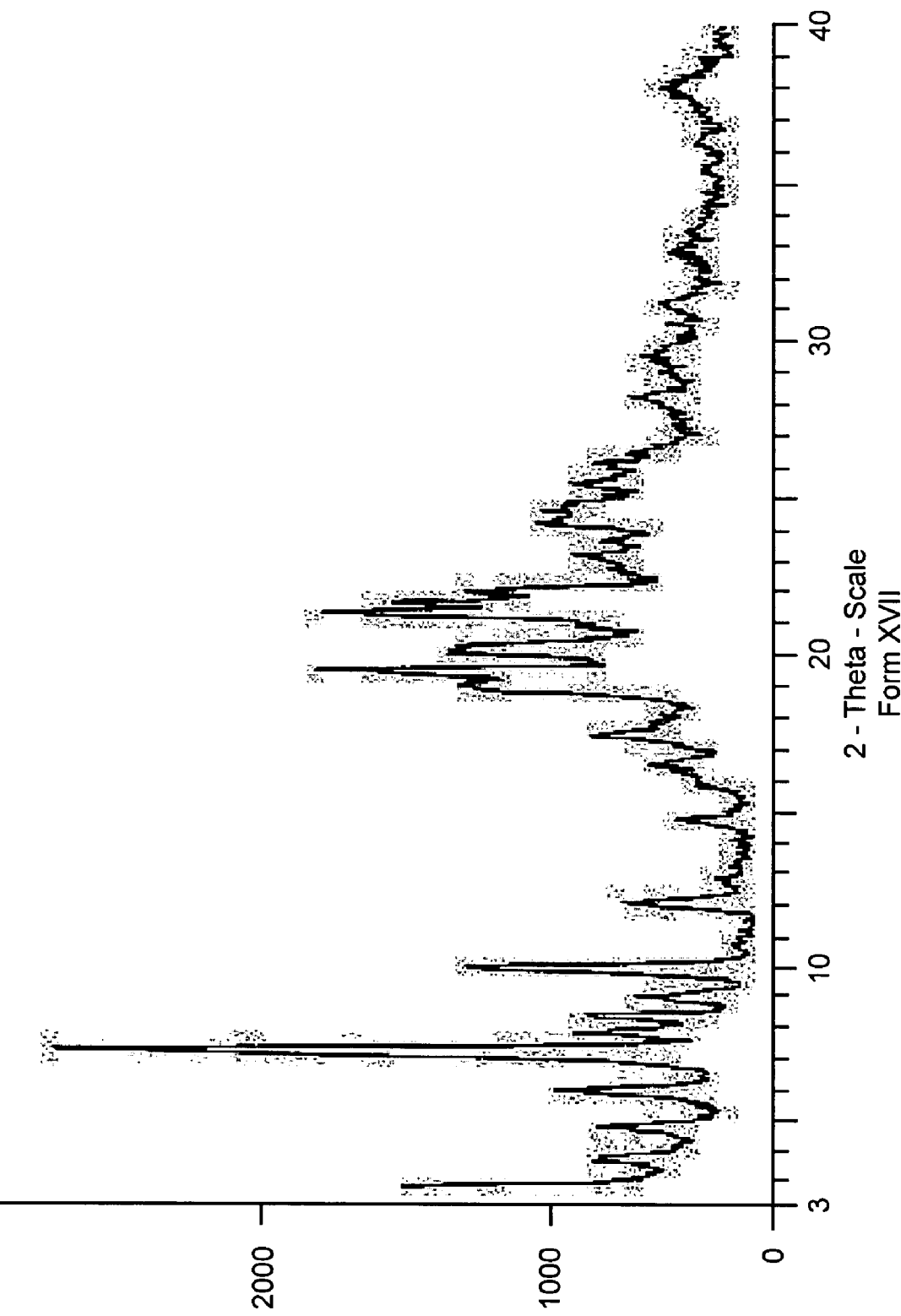
FIG. 13
Diffractogram of Form XVII atorvastatin carried out on Bruker D 5000 diffractometer.
Figure 14:
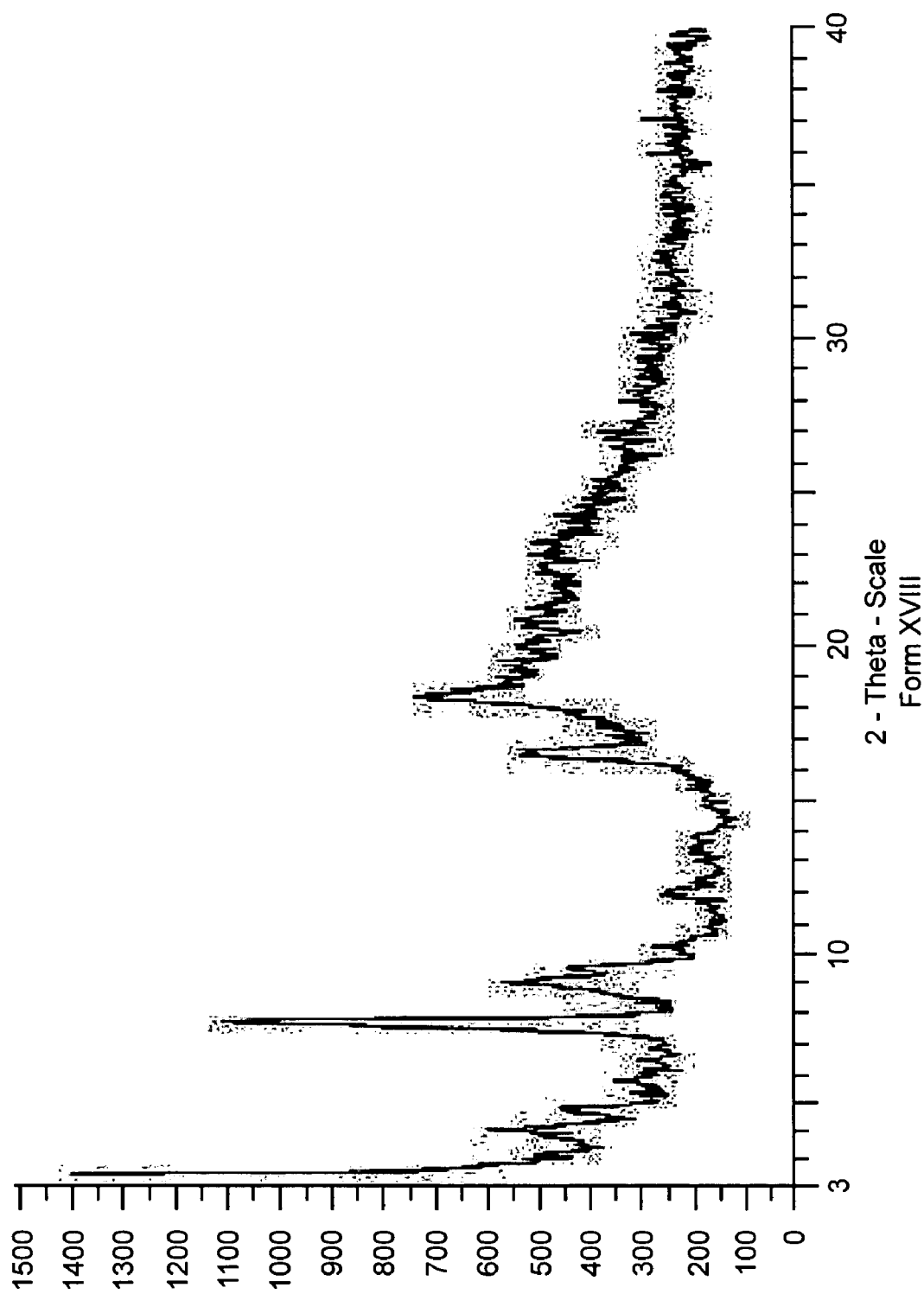
FIG. 14
Diffractogram of Form XVIII atorvastatin carried out on Bruker D 5000 diffractometer.
Figure 15:
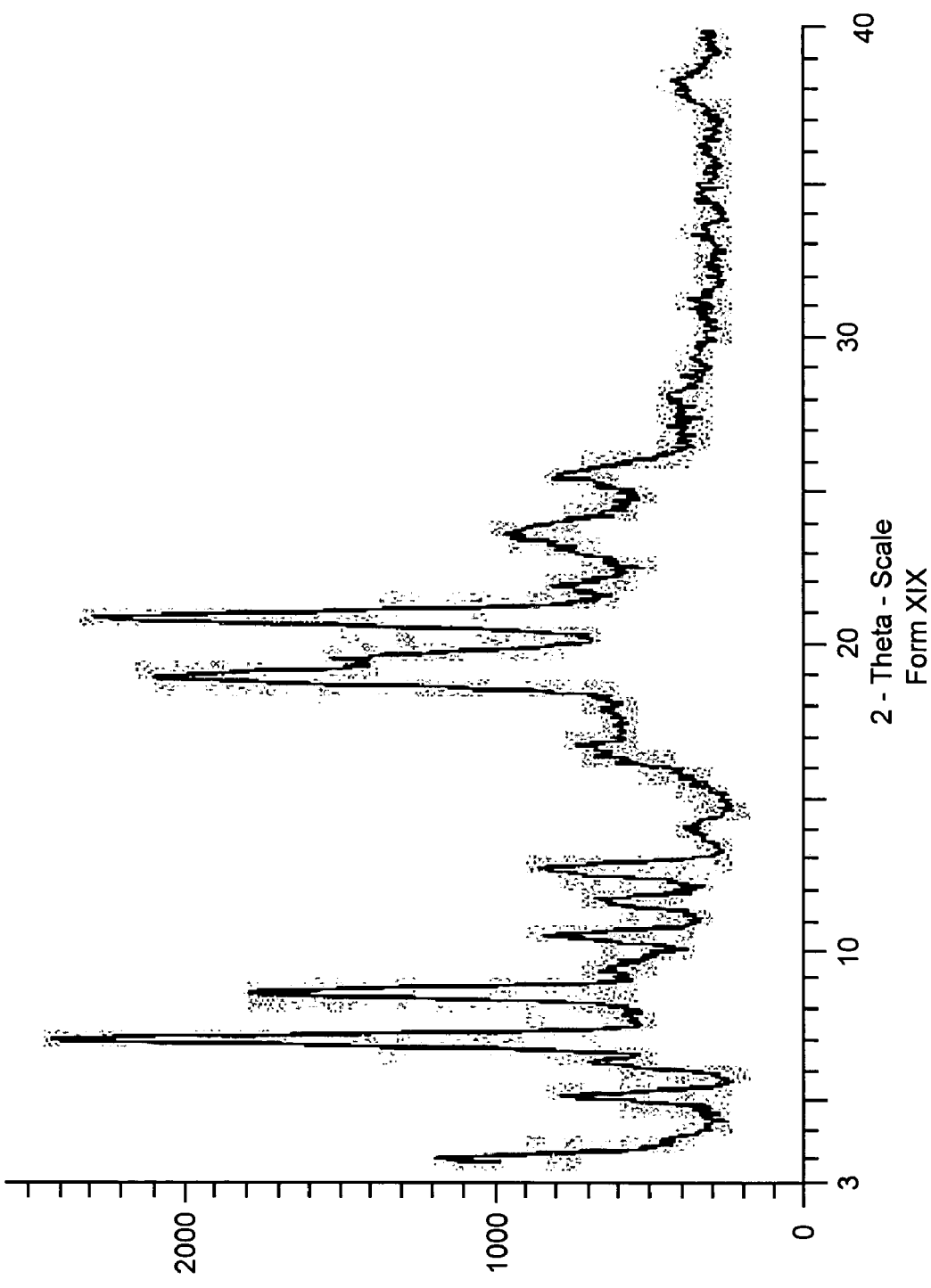
FIG. 15
Diffractogram of Form XIX atorvastatin carried out on Bruker D 5000 diffractometer.
Figure 16:
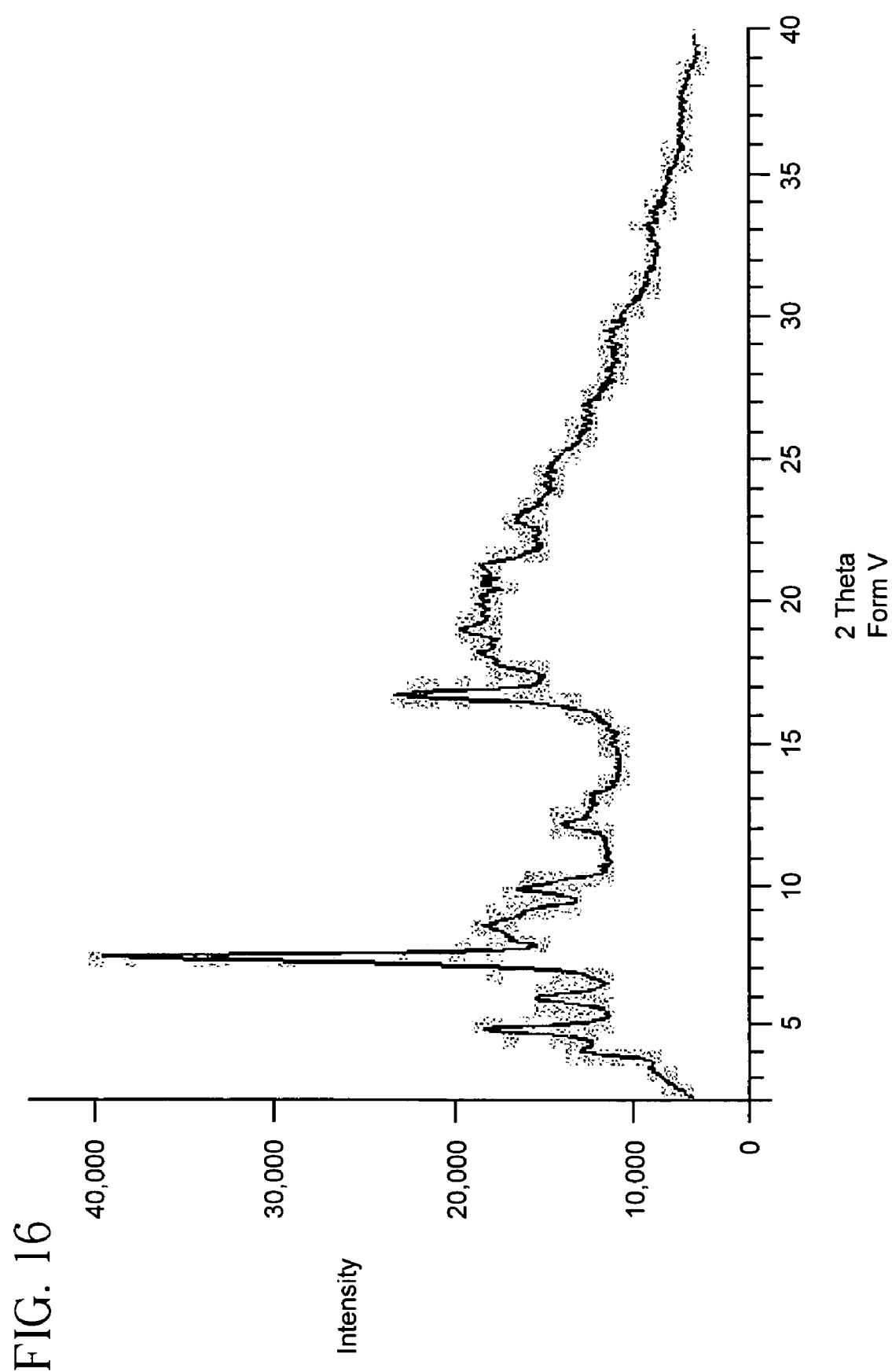
FIG. 16
Diffractogram of Form V atorvastatin carried out on Inel XRG-3000 diffractometer.
Figure 17:
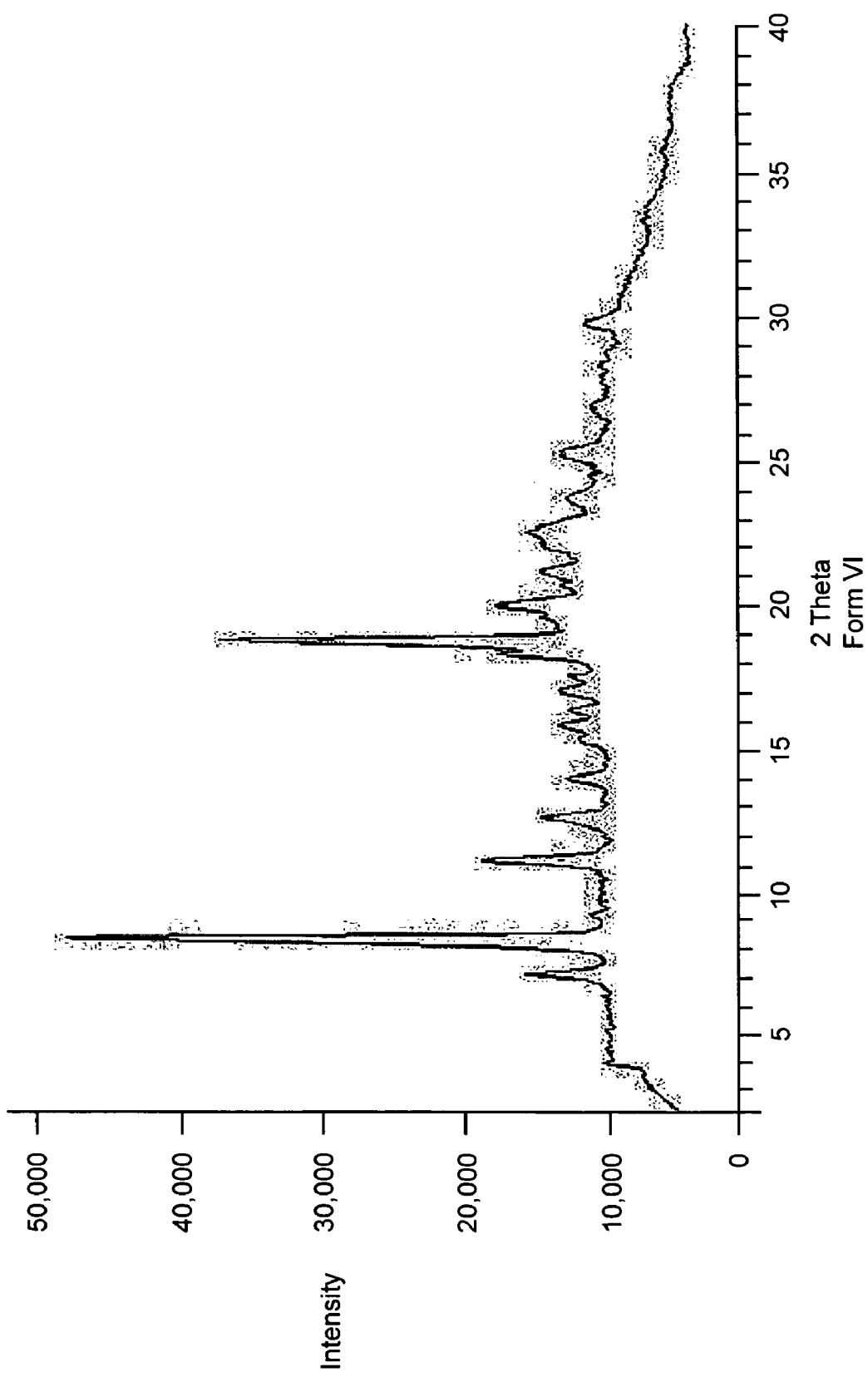
FIG. 17
Diffractogram of Form VI atorvastatin carried out on Inel XRG-3000 diffractometer.
Figure 18:
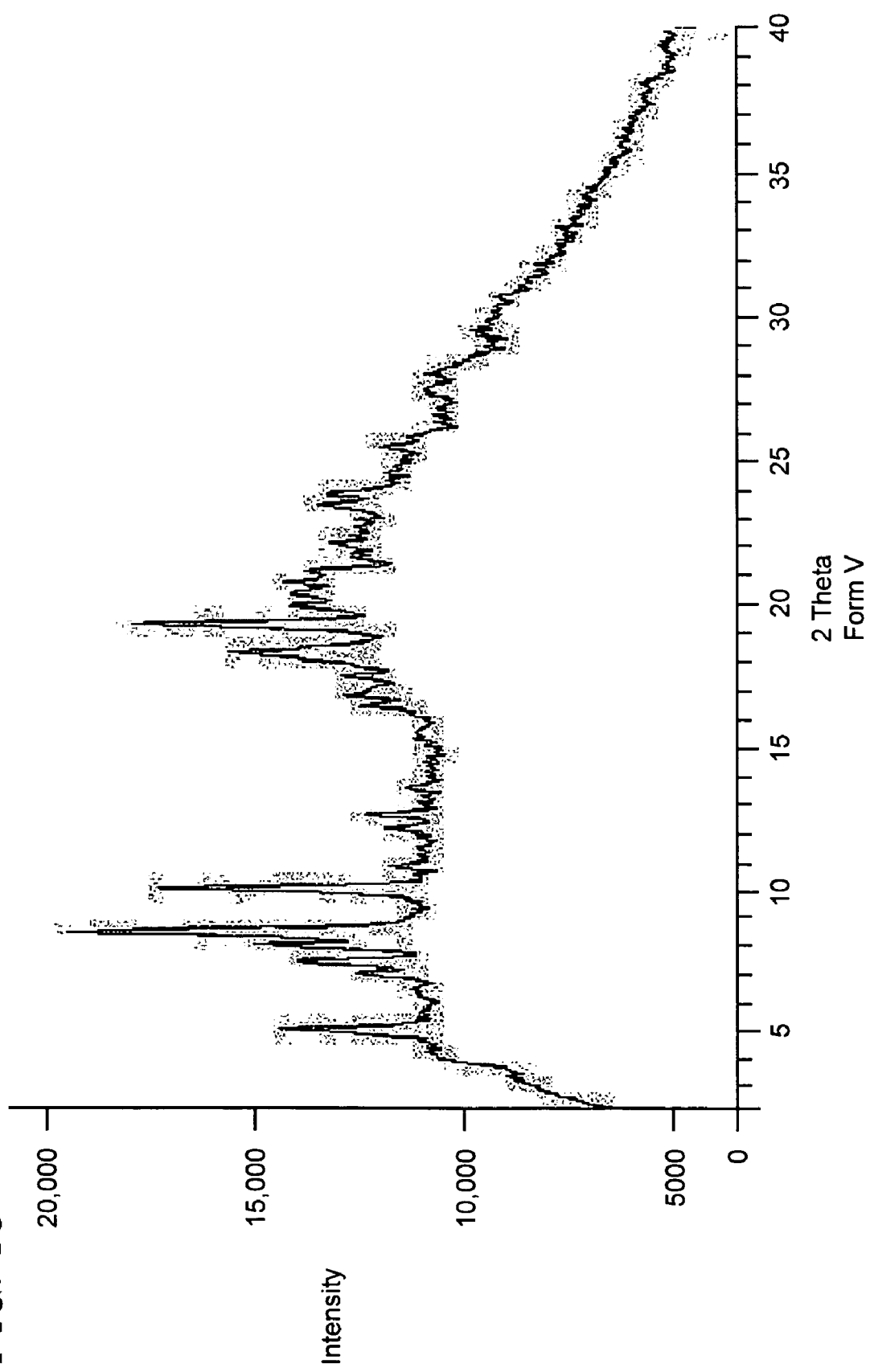
FIG. 18
Diffractogram of Form VII atorvastatin carried out on Inel XRG-3000 diffractometer.
Figure 19:
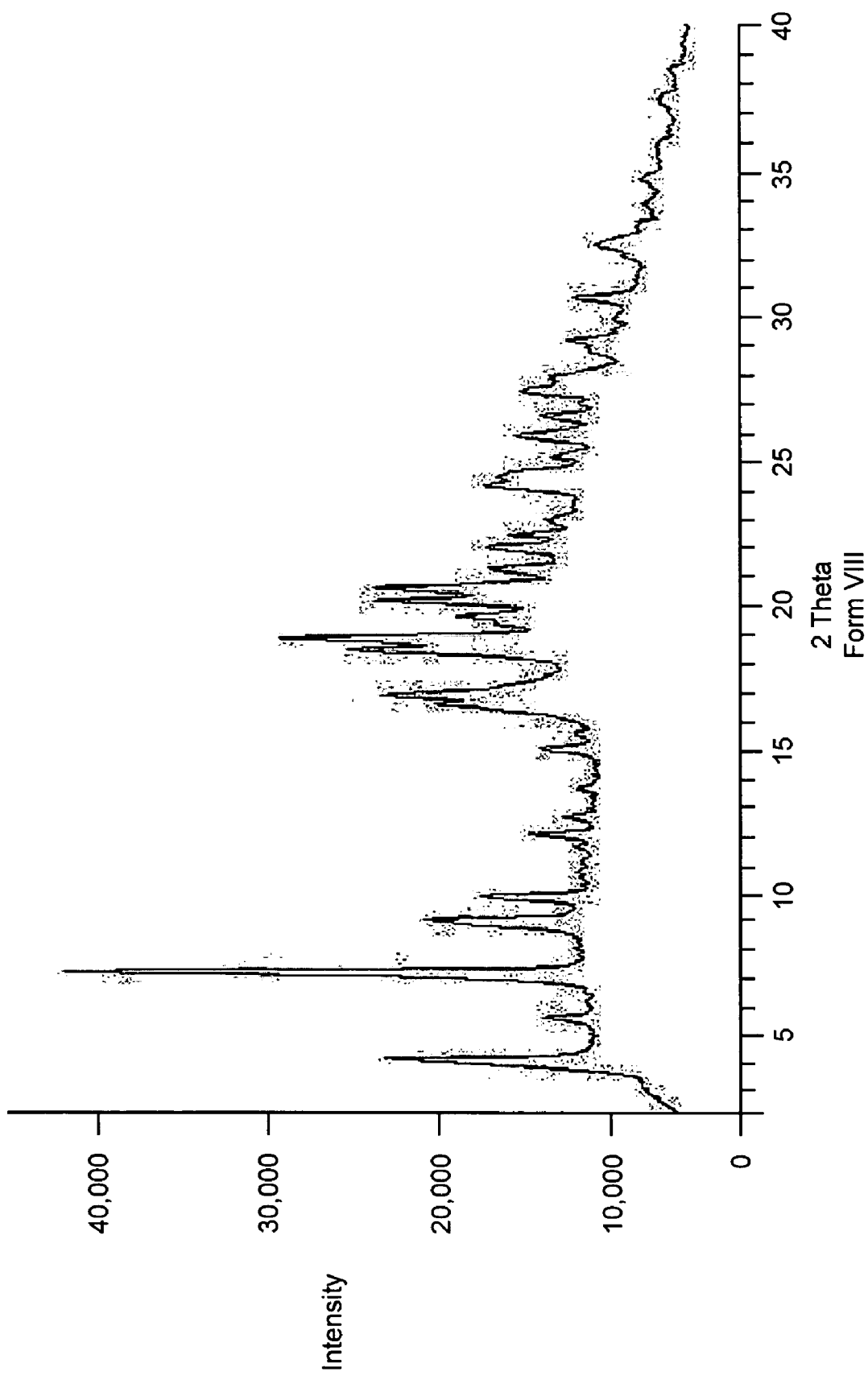
FIG. 19
Diffractogram of Form VIII atorvastatin carried out on Inel XRG-3000 diffractometer.
Figure 20:
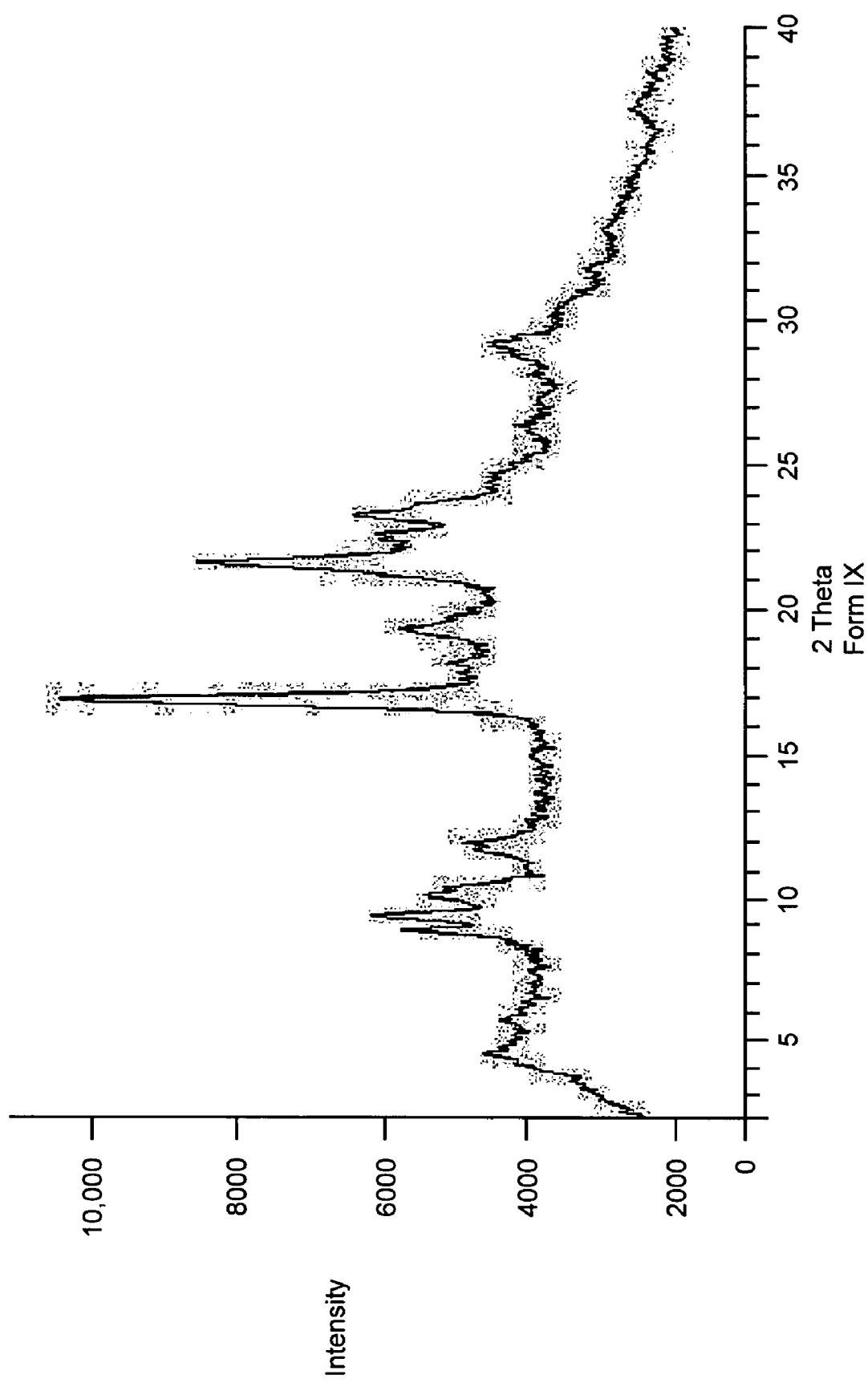
FIG. 20
Diffractogram of Form IX atorvastatin carried out on Inel XRG-3000 diffractometer.
Figure 21:
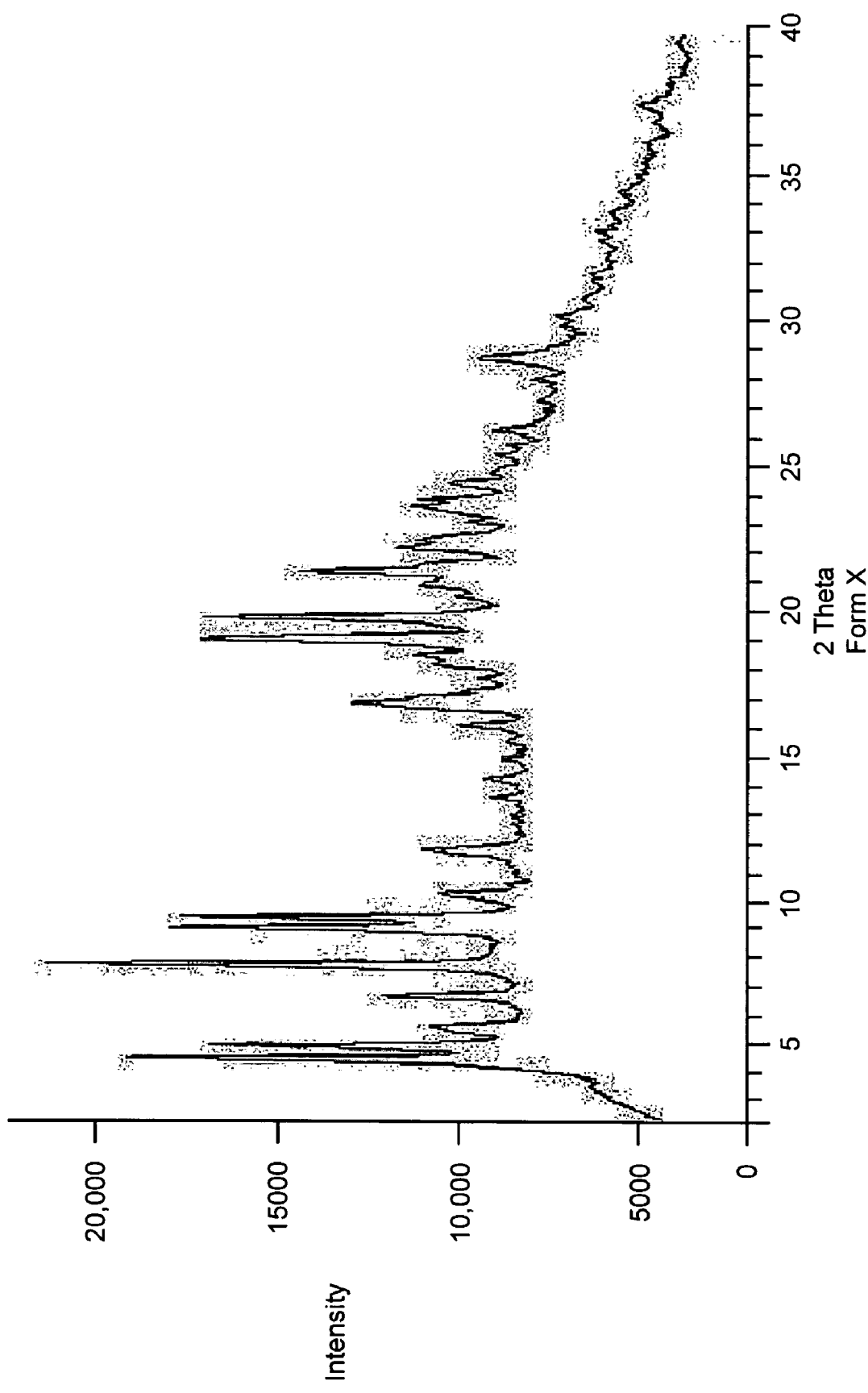
FIG. 21
Diffractogram of Form X atorvastatin carried out on Inel XRG-3000 diffractometer.
Figure 22:
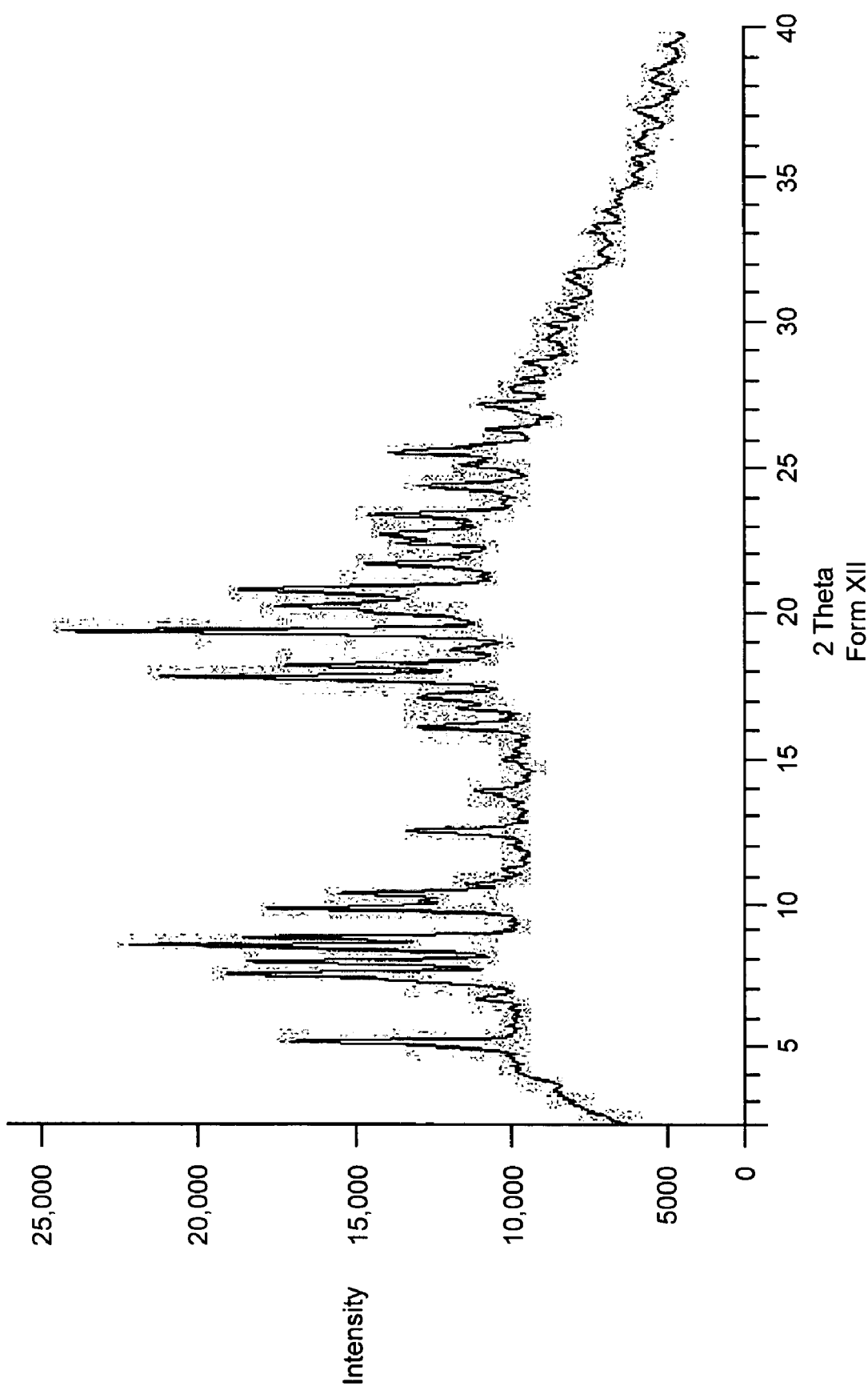
FIG. 22
Diffractogram of Form XII atorvastatin carried out on Inel XRG-3000 diffractometer.
Figure 23:
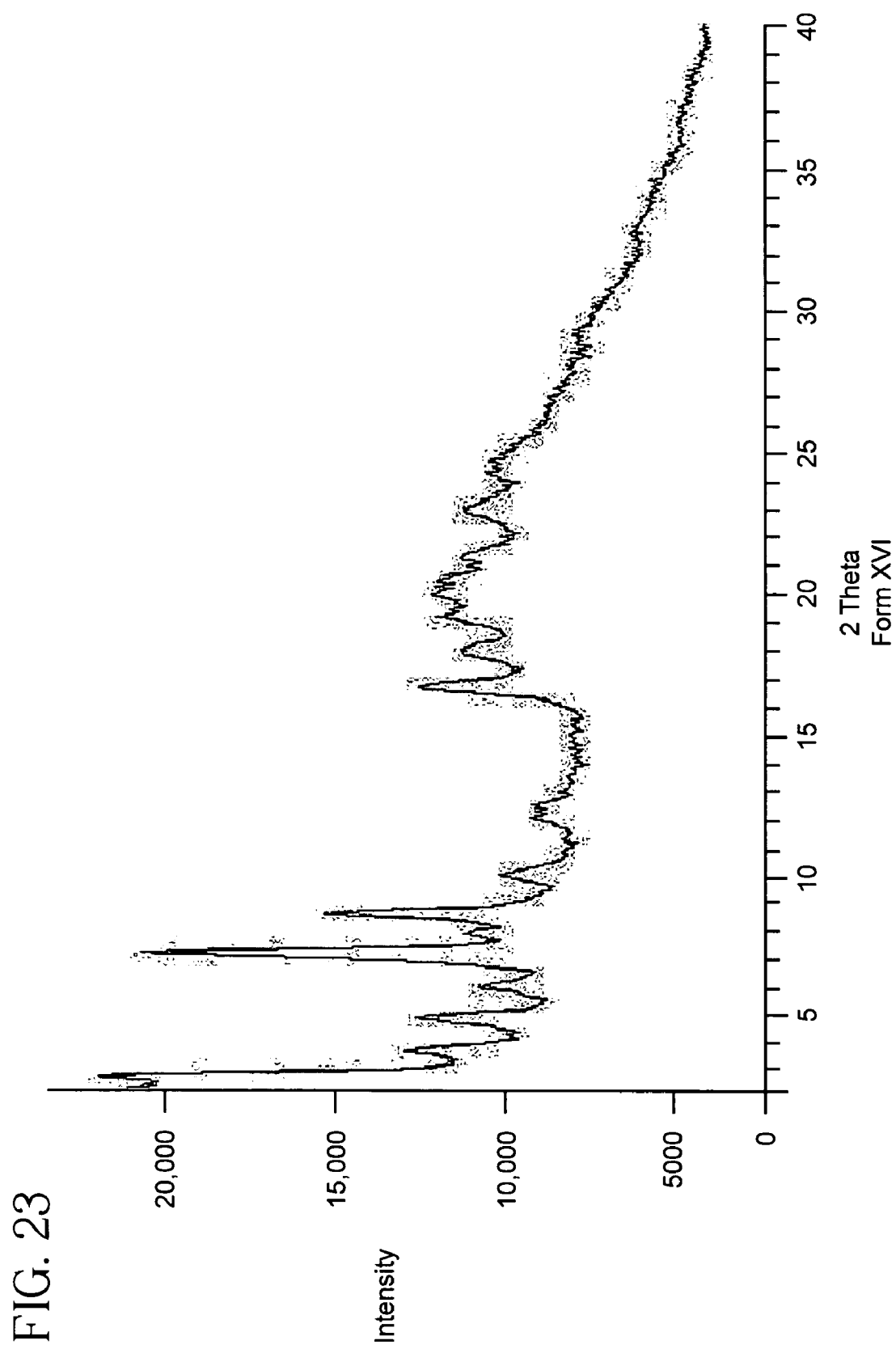
FIG. 23
Diffractogram of Form XVI atorvastatin carried out on Inel XRG-3000 diffractometer.
Figure 24:
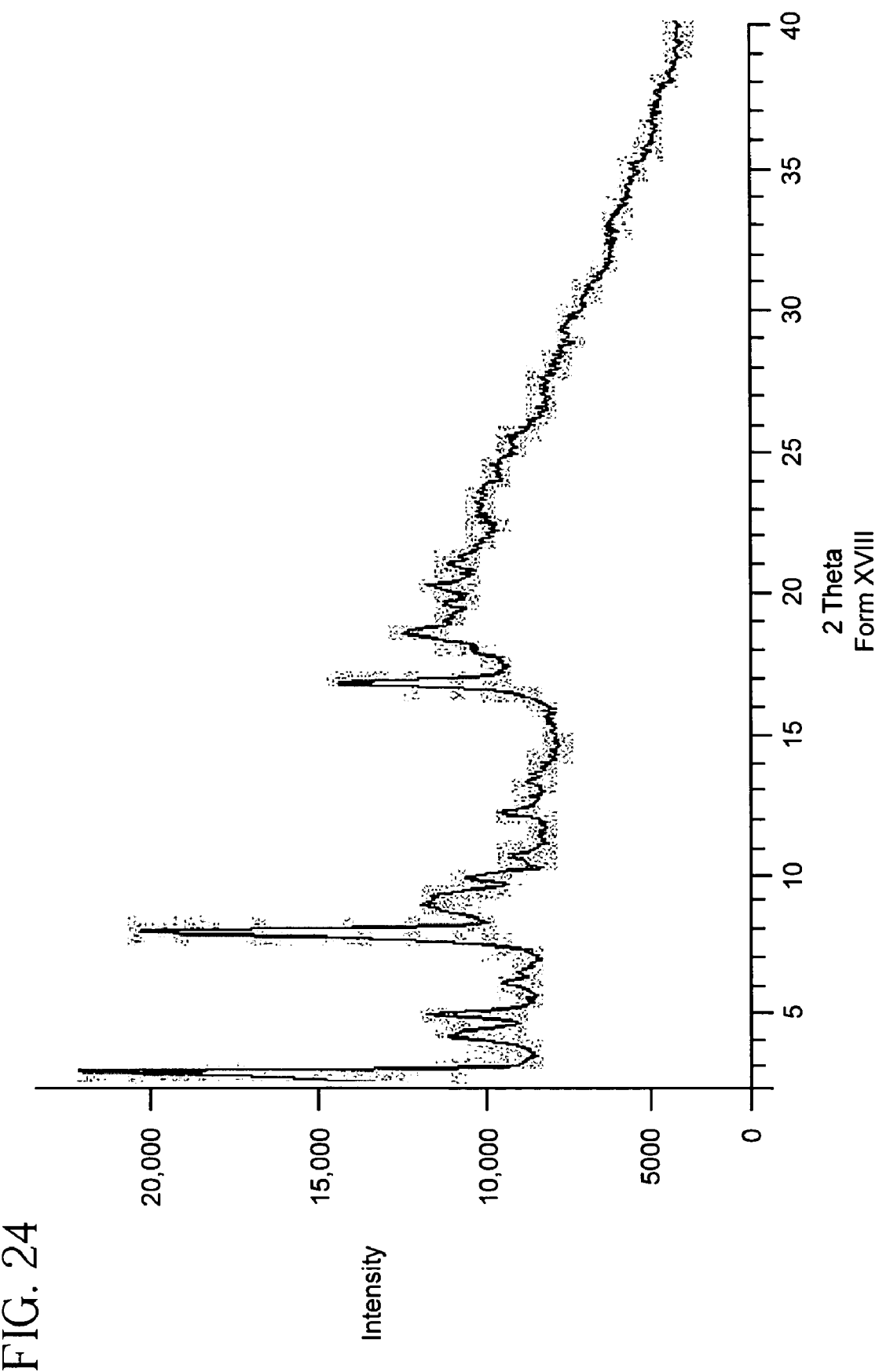
FIG. 24
Diffractogram of Form XVIII atorvastatin carried out on Inel XRG-3000 diffractometer.
Figure 25:
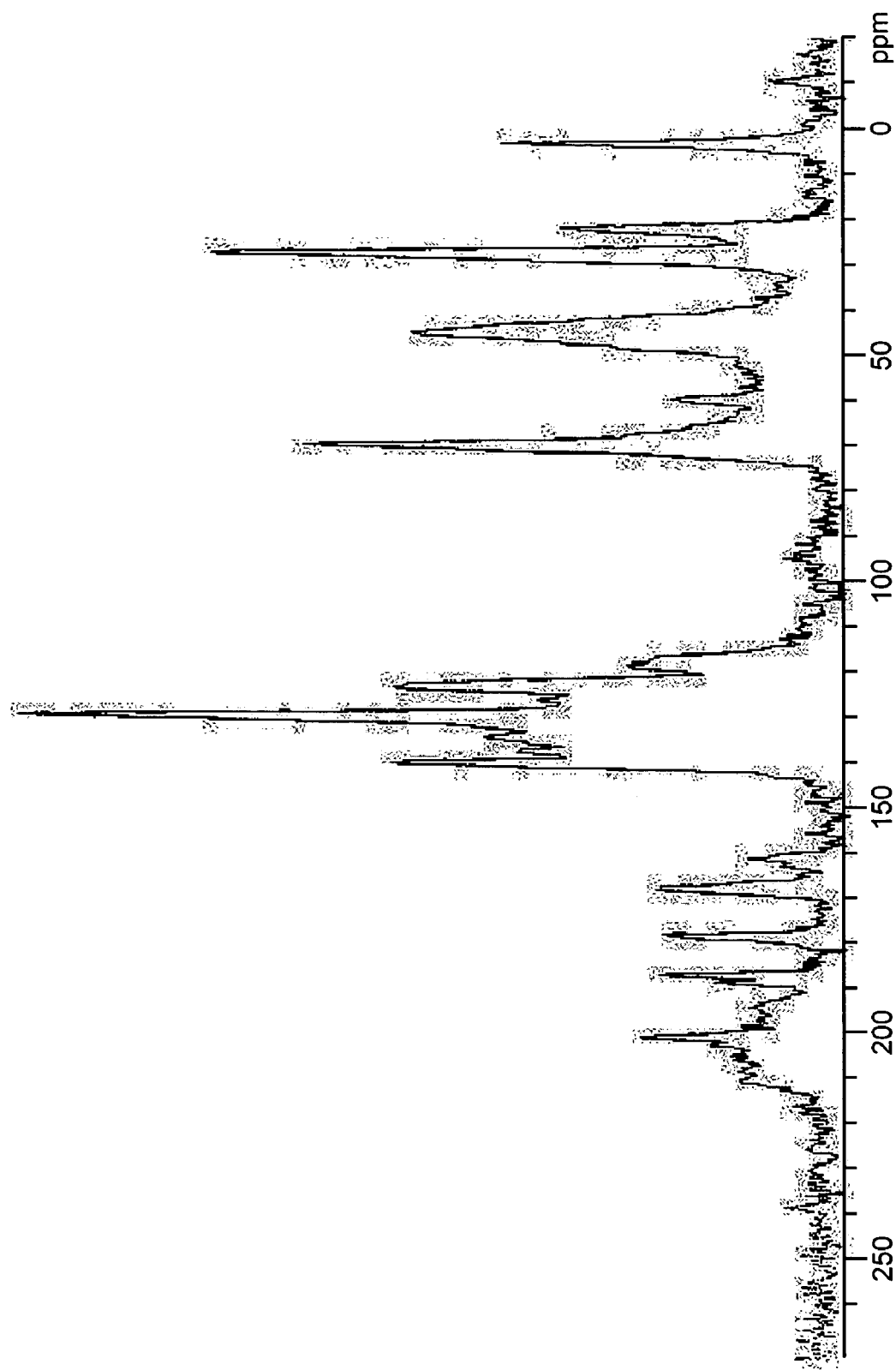
FIG. 25
Figure 26:
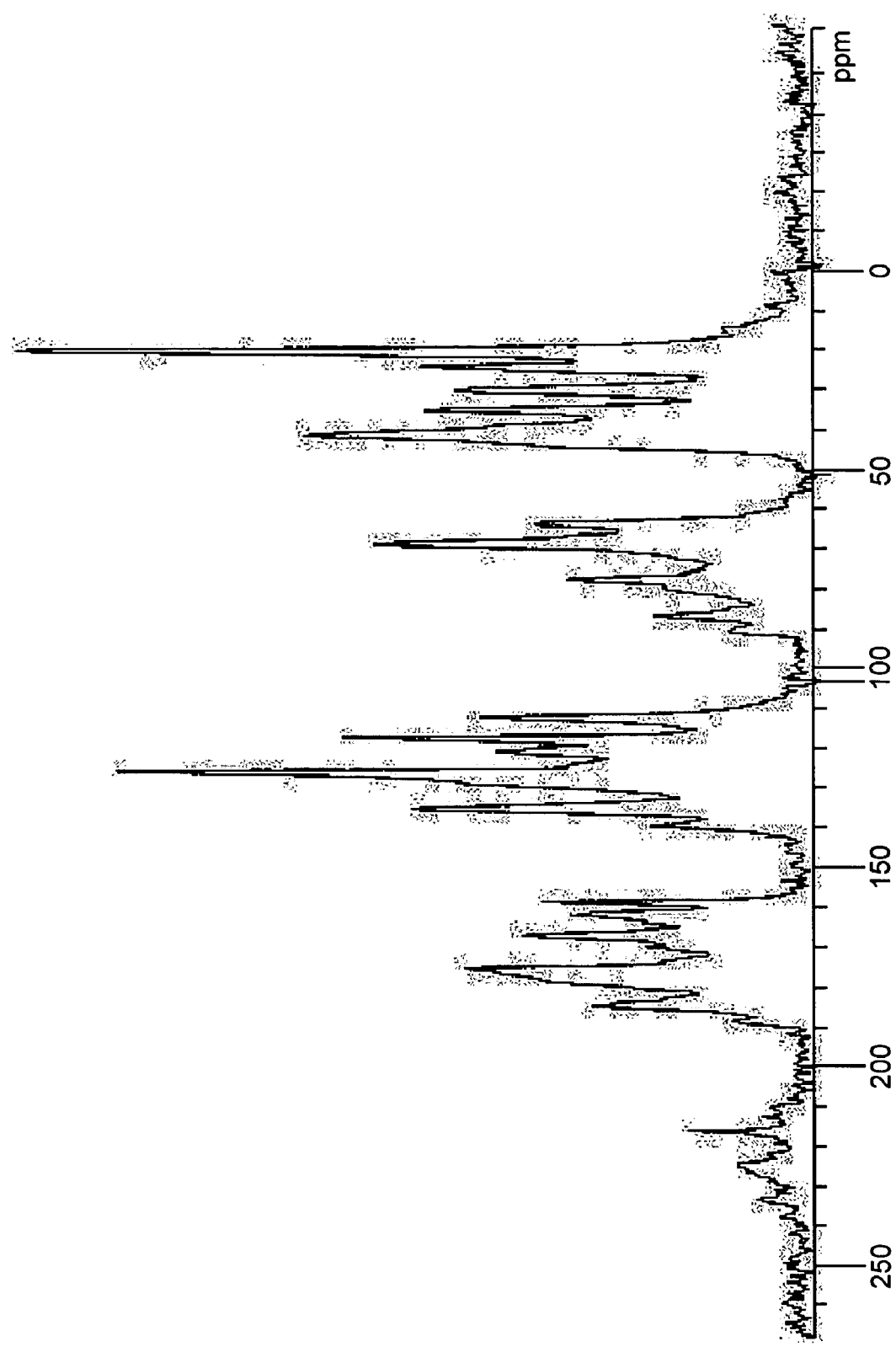
Figure 27:
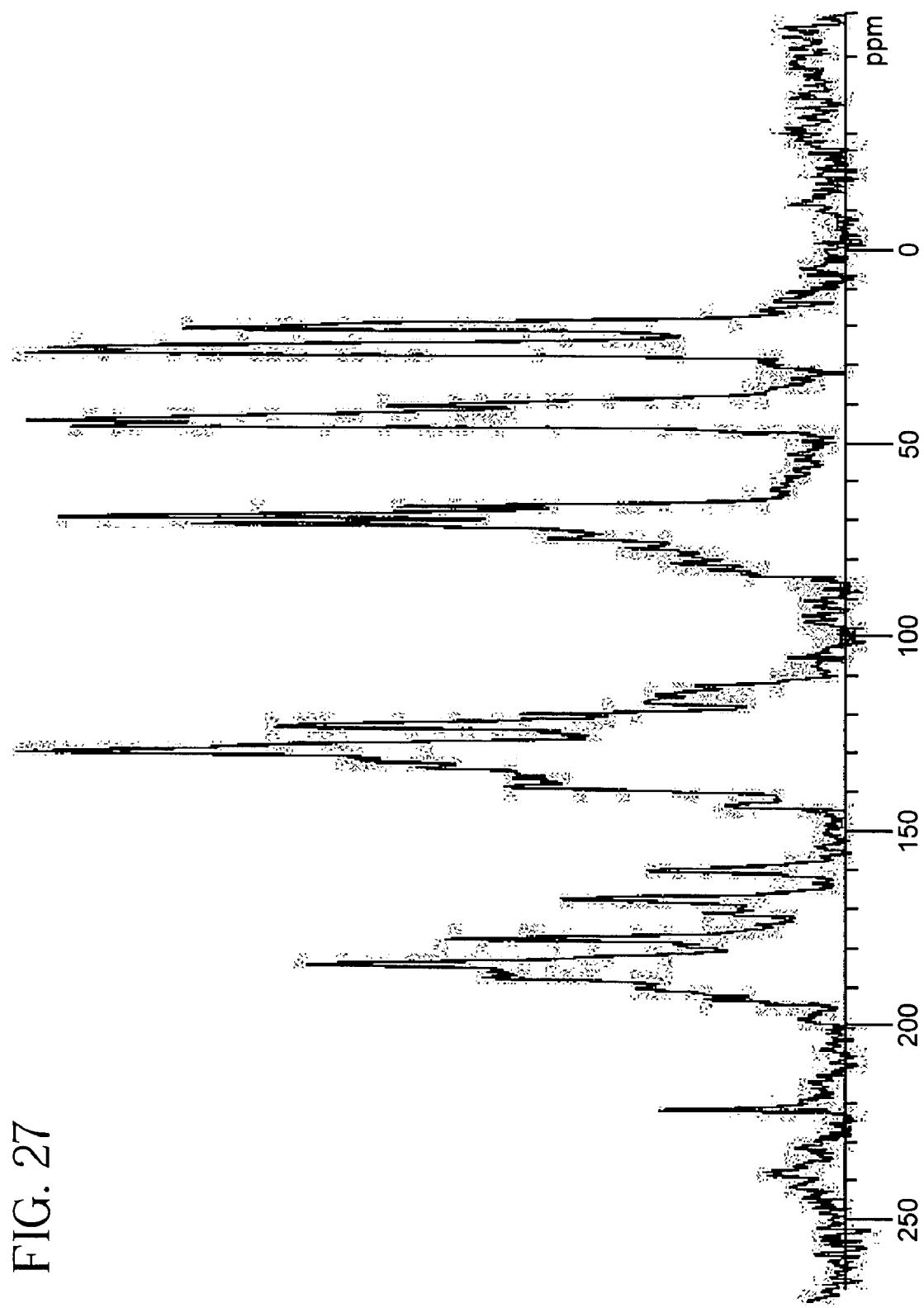
Figure 28:
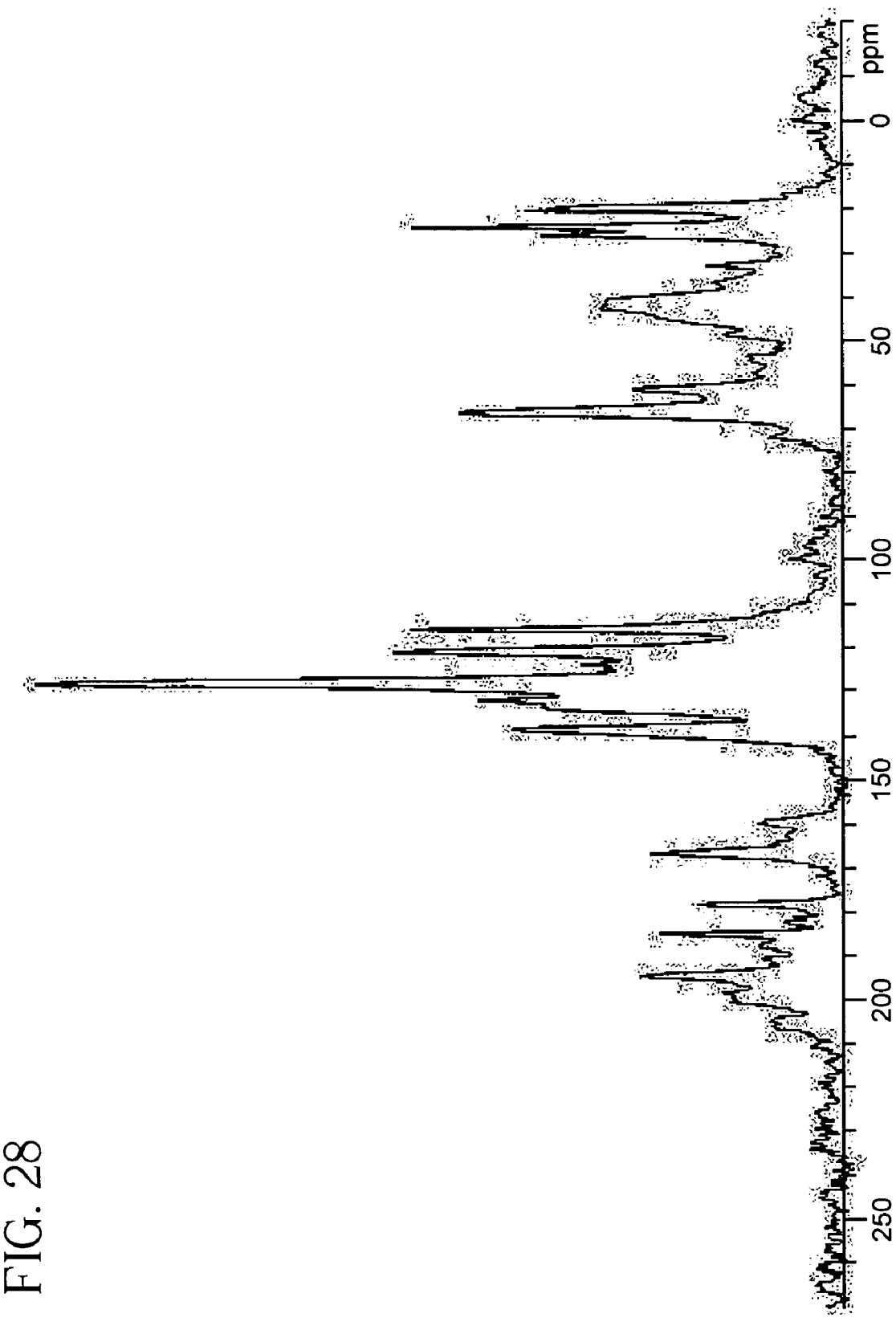
Figure 29:
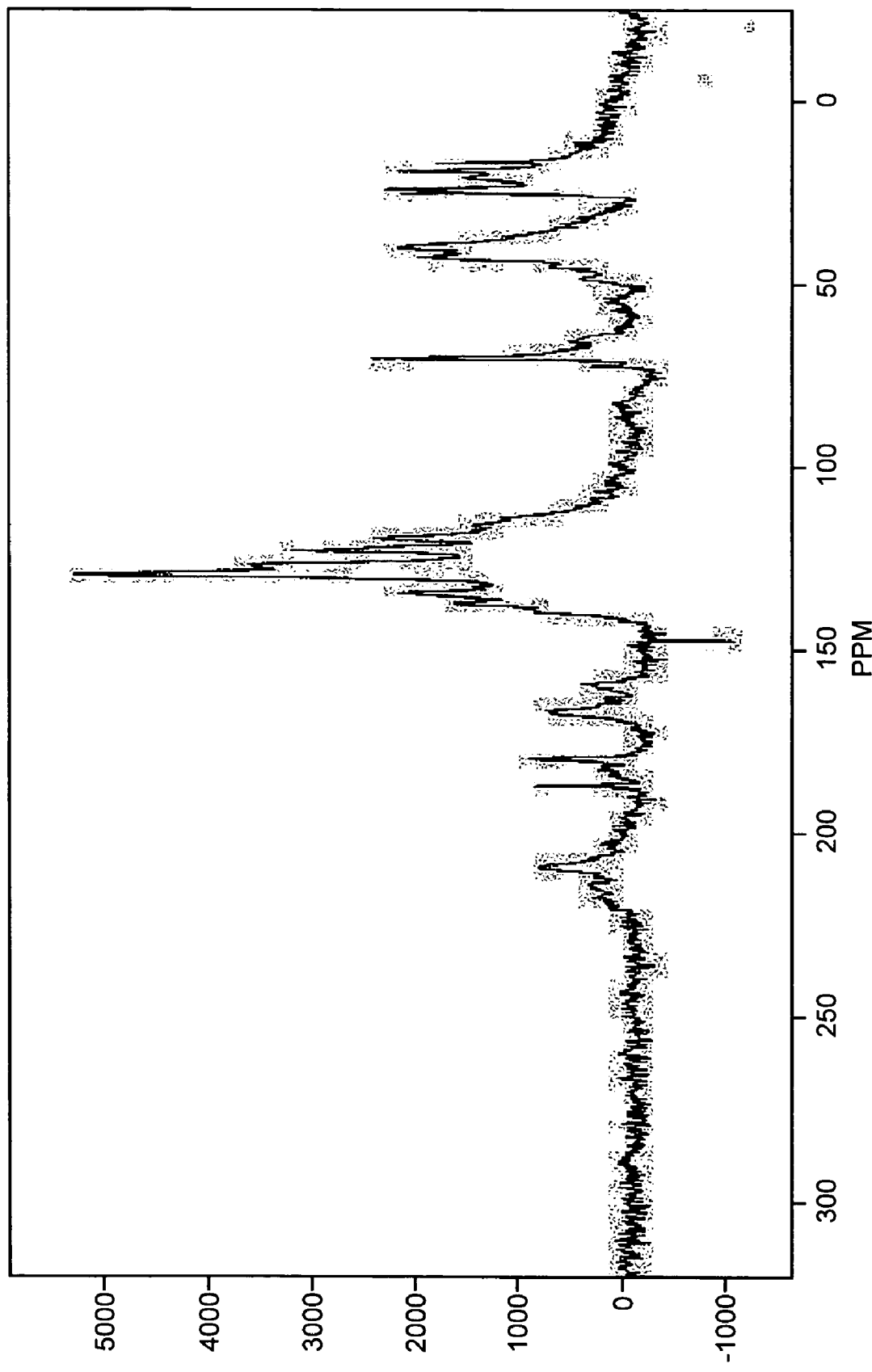
Figure 30:
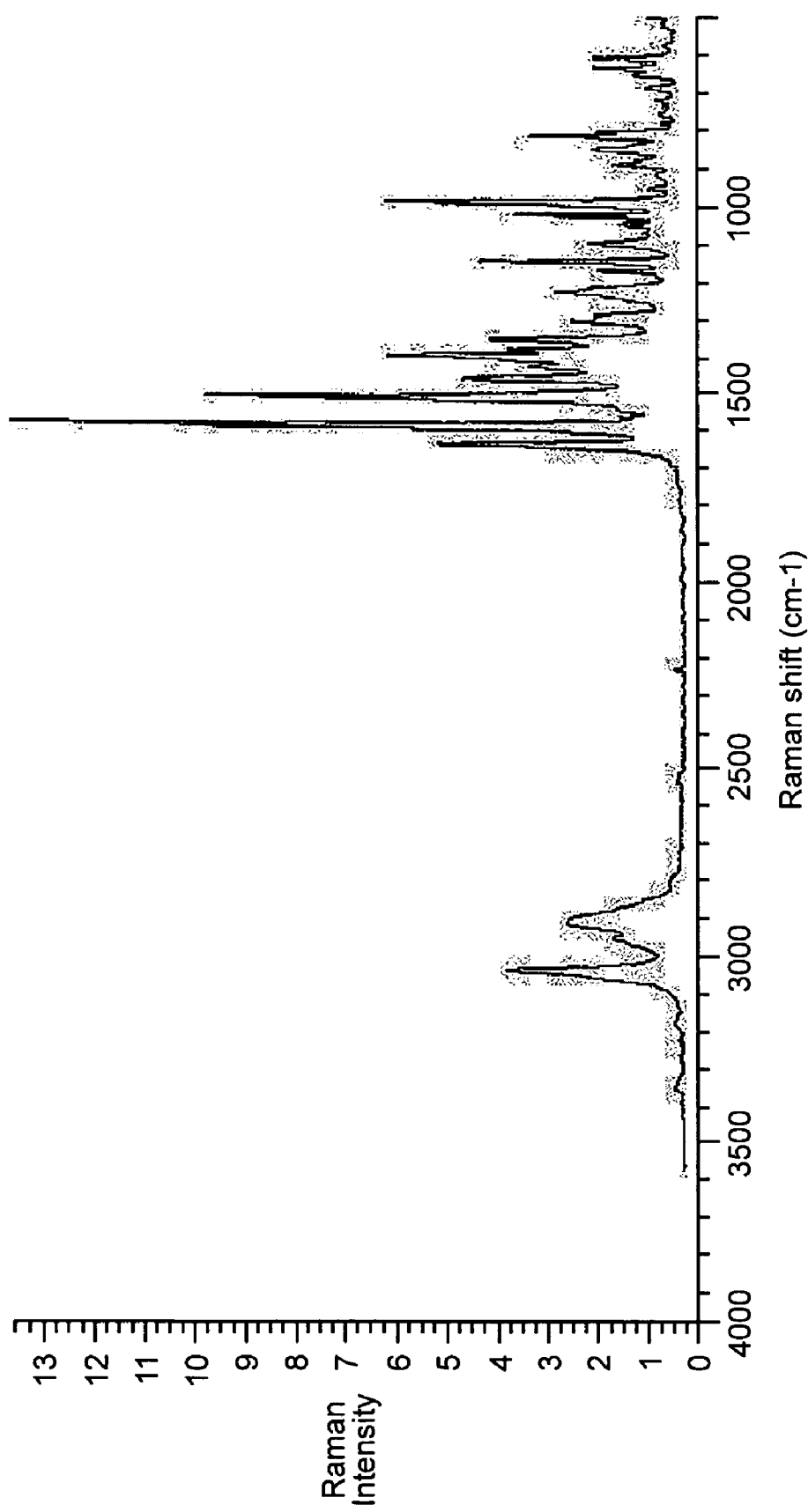
Figure 31:
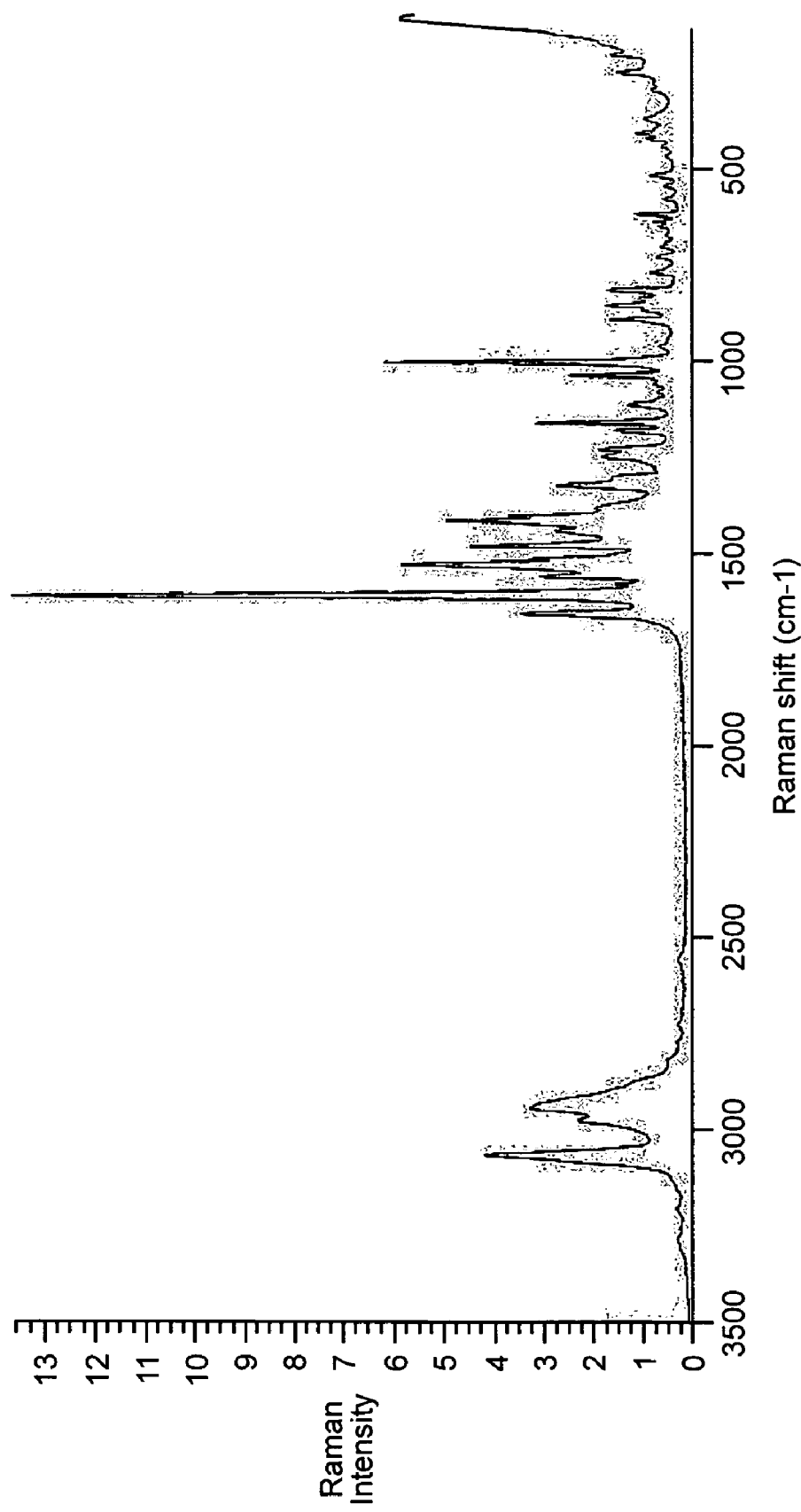
Figure 32:
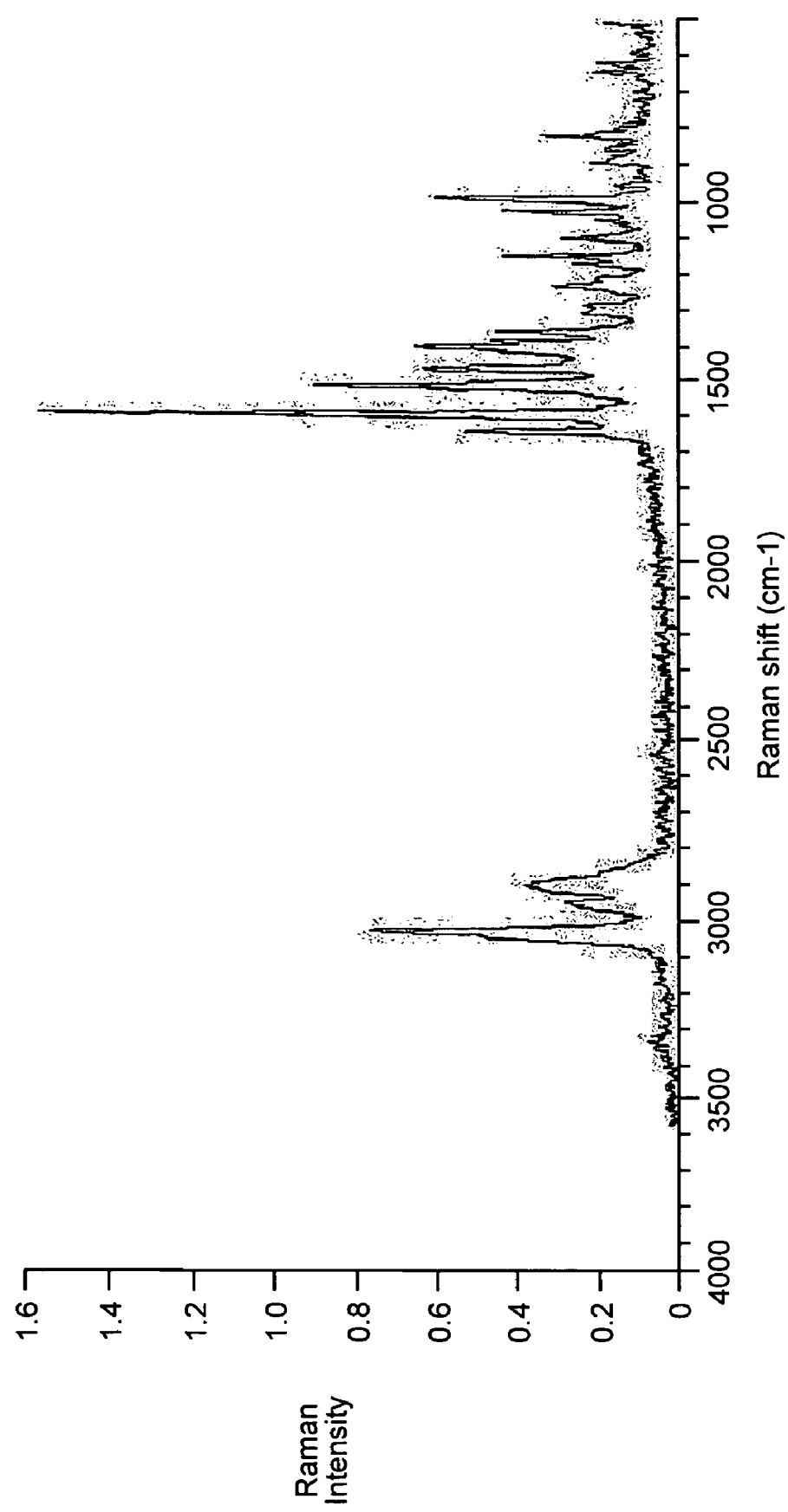
Figure 33:
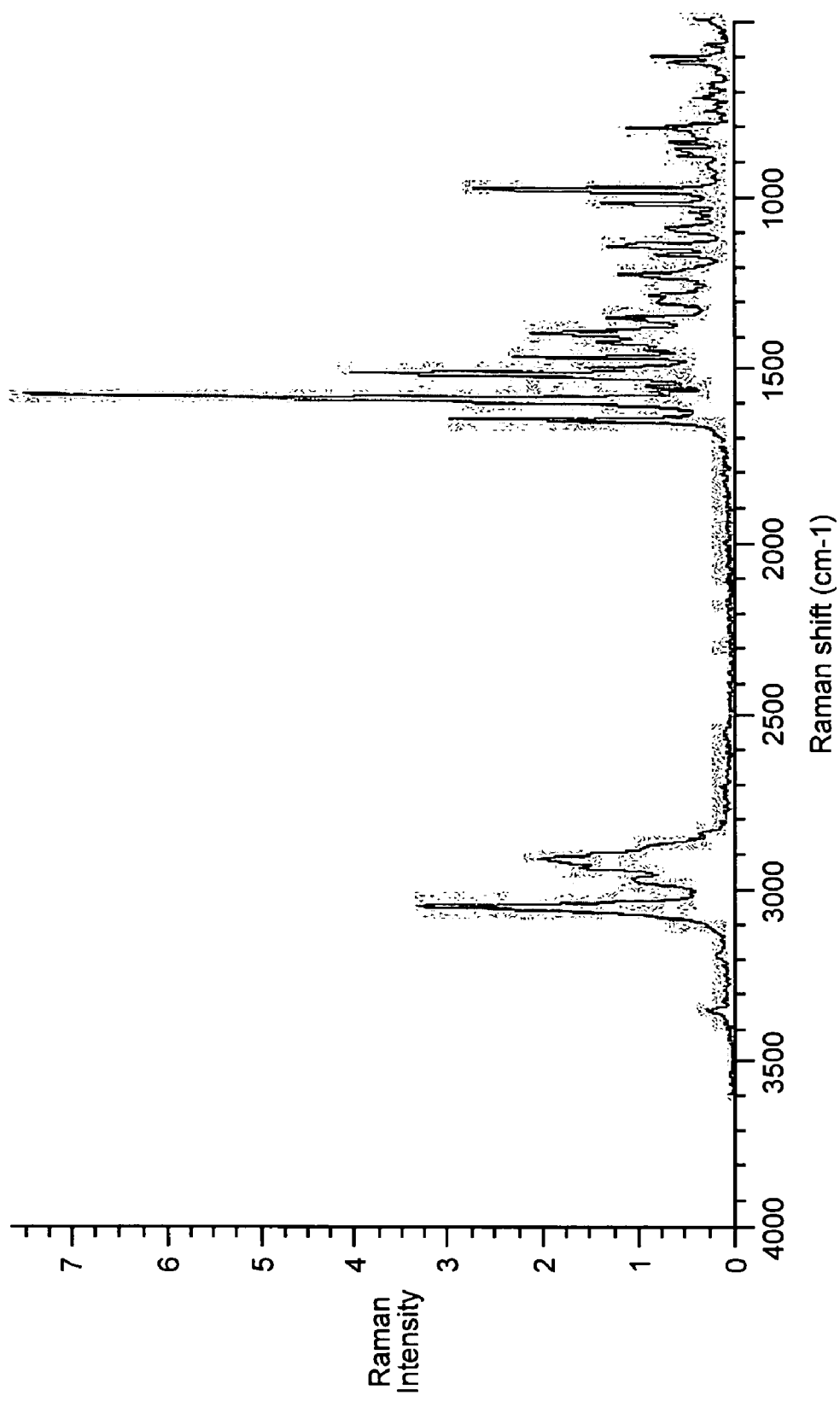
Figure 34:
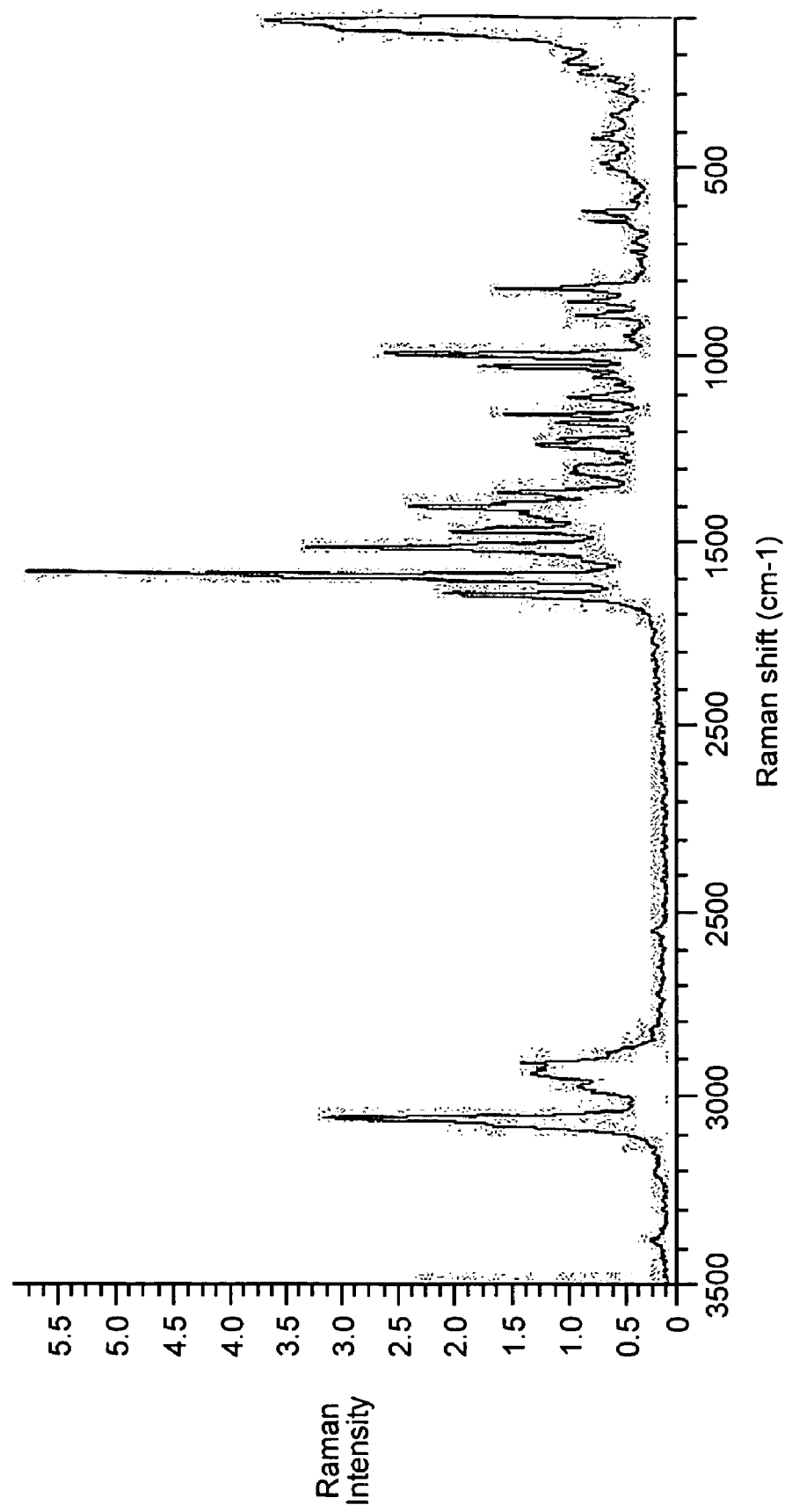
Figure 35:
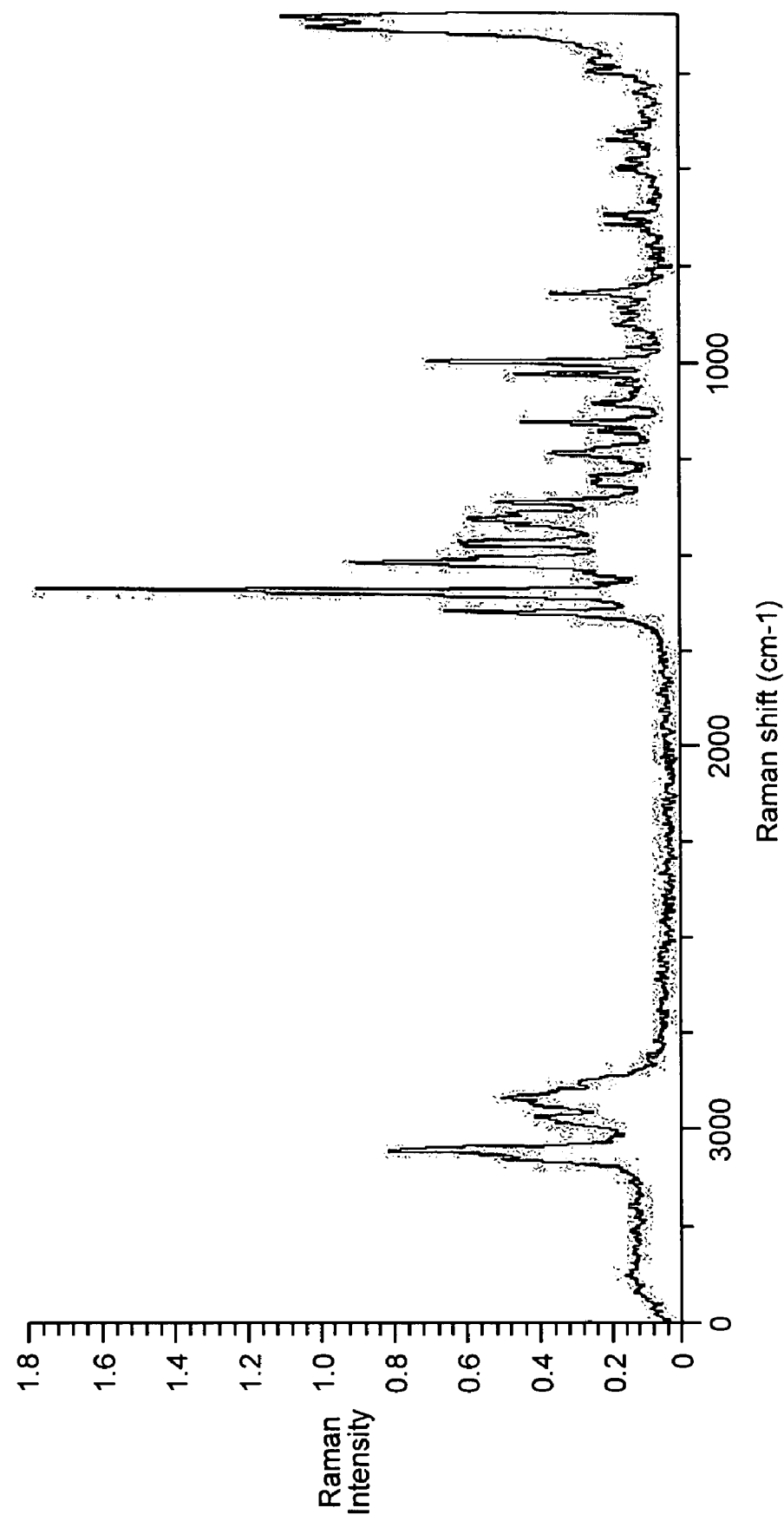

Solid-state $^{13}$C nuclear magnetic resonance spectrum with spinning side bands identified by an asterisk of Form V atorvastatin.

FIG. 26

Solid-state $^{13}$C nuclear magnetic resonance spectrum with spinning side bands identified by an asterisk of Form VI atorvastatin.

FIG. 27

Solid-state $^{13}$C nuclear magnetic resonance spectrum with spinning side bands identified by an asterisk of Form VII atorvastatin.

FIG. 28

Solid-state $^{13}$C nuclear magnetic resonance spectrum with spinning side bands identified by an asterisk of Form VIII atorvastatin.

FIG. 29

Solid-state $^{13}$C nuclear magnetic resonance spectrum of Form X atorvastatin.

FIG. 30

Raman spectrum of Form V.

FIG. 31

Raman spectrum of Form VI.

FIG. 32

Raman spectrum of Form VII.

FIG. 33

Raman spectrum of Form VIII.

FIG. 34

Raman spectrum of Form X.

FIG. 35

Raman spectrum of Form XII.

DETAILED DESCRIPTION OF THE INVENTION

Crystalline Form V, Form VI, Form VII, Form VIII, Form IX, Form X, Form XI, Form XII, Form XIII, Form XIV, Form XV, Form XVI, Form XVII, Form XVIII, and Form XIX atorvastatin may be characterized by their X-ray powder diffraction patterns, by their solid state nuclear magnetic resonance spectra (NMR), and/or their Raman spectra.

X-Ray Powder Diffraction

Forms V, VI, VII, VIII, IX, X, XI, XII, XIII, XIV, XV, XVI, XVII, XVIII, and XIX Forms V, VI, VII, VIII, IX, X, XI, XII, XIII, XIV, XV, XVI, XVII, XVIII, or XIX atorvastatin were characterized by their X-ray powder diffraction pattern. Thus, the X-ray diffraction patterns of Forms V, VI, VII, VIII, IX, X, XI, XII, or Form XIII atorvastatin were carried out on a Shimadzu XRD-6000 X-ray powder diffractometer using CuK$_\alpha$ radiation. The instrument is equipped with a fine-focus X-ray tube. The tube voltage and amperage were set at 40 kV and 40 mA, respectively. The divergence and scattering slits were set at 1°, and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed each day to check the instrument alignment. The X-ray diffraction patterns of Forms XIV, XV, XVI, XVII, XVIII, and XIX were carried out on a Bruker D5000 diffractometer using copper radiation, fixed slits (1.0, 1.0, 0.6 mm), and a Kevex solid state detector. Data was collected from 3.0 to 40.0 degrees in 2θ using a step size of 0.04 degrees and a step time of 1.0 seconds. It should be noted that Bruker Instruments purchased Siemans; thus, a Bruker D 5000 instrument is essentially the same as a Siemans D 5000.

The X-ray diffraction patterns of Forms V, VI, VII, VIII, IX, X, XII, XVI, and XVIII were also carried out on an Inel diffractometer. X-ray diffraction analyses were carried out on an Inel XRG-3000 diffractometer, equipped with a Curved Position Sensitive (CPS) detector with a 2θ range of 120 degrees. Real time data were collected using CuK$_\alpha$ radiation starting at approximately 4°2θ at a resolution of 0.03°2θ. The tube voltage and amperage were set to 40 kV and 30 mA, respectively. Samples were prepared for analysis by packing them into thin-walled glass capillaries. Each capillary was mounted onto a goniometer head that is motorized to permit spinning of the capillary during data acquisition. Instrument calibration was performed daily using a silicon reference standard. The Inel diffractograms for the available forms are shown in the figures without baseline subtraction. Calculating the intensities from these diffractograms is within the skill of the art and involves using baseline subtraction to account for background scattering (e.g., scattering from the capillary).

To perform an X-ray powder diffraction measurement on a Shimadzu or Bruker instrument like the ones used for measurements reported herein, the sample is typically placed into a holder which has a cavity. The sample powder is pressed by a glass slide or equivalent to ensure a random surface and proper sample height. The sample holder is then placed into the instrument (Shimadzu or Bruker). The source of the X-ray beam is positioned over the sample, initially at a small angle relative to the plane of the holder, and moved through an arc that continuously increases the angle between the incident beam and the plane of the holder. Measurement differences associated with such X-ray powder analyses result from a variety of factors including: (a) errors in sample preparation (e.g., sample height), (b) instrument errors (e.g., flat sample errors), (c) calibration errors, (d) operator errors (including those errors present when determining the peak locations), and (e) preferred orientation. Calibration errors and sample height errors often result in a shift of all the peaks in the same direction and by the same amount. Small differences in sample height on a flat holder lead to large displacements in XRPD peak positions. A systematic study showed that, using a Shimadzu XRD-6000 in the typical Bragg-Brentano configuration, sample height differences of 1 mm led to peak shifts as high as 1°2θ (Chen, et al., *J. Pharmaceutical and Biomedical Analysis*, 2001;26: 63). These shifts can be identified from the X-ray diffractogram and can be eliminated by compensating for the shift (applying a systematic correction factor to all peak position values) or recalibrating the instrument. In contrast, the Inel instrument used herein places the sample in a capillary which is positioned at the center of the instrument. This minimizes sample height errors (a) and preferred orientation (e). Since, when using capillaries, the sample height is not established manually, the peak locations from the Inel measurements are typically more accurate than those from the Shimadzu or the Bruker instrument. As mentioned above, it is possible to rectify measurements from the various machines by applying a systematic correction factor to bring the peak positions into agreement. In general, this correction factor will bring the peak positions from the Shimadzu and Bruker into agreement with the Inel and will be in the range of 0 to 0.2°2θ.

Table 1 lists the 2θ and relative intensities of all lines in the sample with a relative intensity of >10% for crystalline Forms V–XIX atorvastatin. The numbers listed in this table are rounded numbers.

TABLE 1

Intensities and Peak Locations of All Diffraction Lines With Relative Intensity Greater Than 10%[a]
for Forms V to XIX (Measured on Shimadzu Diffractometer)

| 2θ | Relative Intensity (>10%) | 2θ | Relative Intensity (>10%) | 2θ | Relative Intensity (>10%) | 2θ | Relative Intensity (>10%) | 2θ | Relative Intensity (>10%) |
|---|---|---|---|---|---|---|---|---|---|
| Form V | | Form VI | | Form VII | | Form VIII | | Form IX | |
| 4.9* | 9 | 7.2 | 11 | 8.6 | 76 | 7.5 | 61 | 8.8 | 50 |
| 6.0 | 15 | 8.3 | 77 | 10.2 | 70 | 9.2 | 29 | 9.4* | 32 |
| 7.0 | 100 | 11.0 | 20 | 12.4* | 12 | 10.0 | 16 | 11.2–11.7* | 26 |
| 8.0* | 20 | 12.4 | 11 | 12.8* | 15 | 12.1 | 10 | 16.7 | 59 |
| 8.6 | 57 | 13.8 | 9 | 17.6 | 20 | 12.8 | 6 | 17.5* | 33 |
| 9.9 | 22 | 16.8 | 14 | 18.3* | 43 | 13.8 | 4 | 19.3* | 55 |
| 16.6 | 42 | 18.5 | 100 | 19.3 | 100 | 15.1 | 13 | 21.4* | 100 |
| 19.0 | 27 | 19.7* | 22 | 22.2* | 14 | 16.7* | 64 | 22.4* | 33 |
| 21.1 | 35 | 20.9 | 14 | 23.4* | 23 | 18.6* | 100 | 23.2* | 63 |
|  |  | 25.0* | 15 | 23.8* | 26 | 20.3* | 79 | 29.0* | 15 |
|  |  |  |  | 25.5* | 16 | 21.2 | 24 |  |  |
|  |  |  |  |  |  | 21.9 | 30 |  |  |
|  |  |  |  |  |  | 22.4 | 19 |  |  |
|  |  |  |  |  |  | 25.8 | 33 |  |  |
|  |  |  |  |  |  | 26.5 | 20 |  |  |
|  |  |  |  |  |  | 27.4* | 38 |  |  |
|  |  |  |  |  |  | 30.5 | 20 |  |  |
| Form X | | Form XI | | Form XII | | Form XIII | | Form XIV | |
| 4.7 | 35 | 10.8* | 58 | 5.4 | 11 | 8.4 | 100 | 5.4 | 41 |
| 5.2 | 24 | 12.0 | 12 | 7.7 | 24 | 8.9 | 82 | 6.7 | 31 |
| 5.8 | 11 | 13.5 | 11 | 8.0 | 25 | 15.7* | 45 | 7.7 | 100 |
| 6.9 | 13 | 16.5 | 52 | 8.6 | 42 | 16.4* | 46 | 8.1 | 35 |
| 7.9 | 53 | 17.6–18.0* | 35 | 8.9 | 25 | 17.6* | 57 | 9.0 | 65 |
| 9.2 | 56 | 19.7 | 82 | 9.9 | 36 | 18.1* | 62 | 16.5* | 15 |
| 9.5 | 50 | 22.3 | 100 | 10.4* | 24 | 19.7* | 58 | 17.6* | 17 |
| 10.3* | 13 | 23.2 | 26 | 12.5 | 18 | 20.8* | 91 | 18.0–18.7* | 21 |
| 11.8 | 20 | 24.4 | 28 | 13.9* | 9 | 23.8* | 57 | 19.5* | 18 |
| 16.1 | 13 | 25.8 | 17 | 16.2 | 10 |  |  |  |  |
| 16.9 | 39 | 26.5 | 30 | 17.8 | 70 |  |  |  |  |
| 19.1 | 100 | 27.3 | 31 |  |  |  |  |  |  |
| 19.8 | 71 | 28.7 | 19 | 19.4 | 100 |  |  |  |  |
| 21.4 | 49 | 29.5 | 12 | 20.8 | 51 |  |  |  |  |
| 22.3* | 36 | 30.9* | 17 | 21.7 | 13 |  |  |  |  |
| 23.7* | 37 | 32.8* | 11 | 22.4–22.6* | 18 |  |  |  |  |
| 24.4 | 15 | 33.6* | 15 | 24.3 | 19 |  |  |  |  |
| 28.7 | 31 | 36.0* | 15 | 25.5 | 24 |  |  |  |  |
|  |  | 38.5* | 14 | 26.2 | 11 |  |  |  |  |
|  |  |  |  | 27.1 | 8 |  |  |  |  |
| Form XV | | Form XVI | | Form XVII | | Form XVIII | | Form XIX | |
| 5.7 | 26 | 5.2 | 37 | 5.0 | 27 | 8.0 | 100 | 5.2 | 32 |
| 6.1 | 21 | 6.4 | 34 | 6.1 | 33 | 9.2* | 52 | 6.3 | 28 |
| 6.8 | 18 | 7.5 | 100 | 7.3 | 100 | 9.7* | 40 | 7.0 | 100 |
| 7.5 | 39 | 8.7 | 79 | 7.9 | 30 | 12.1 | 24 | 8.6 | 74 |
| 8.1 | 39 | 10.5* | 19 | 8.5 | 29 | 16.6* | 48 | 10.5 | 34 |
| 8.5 | 42 | 12.0* | 10 | 9.1 | 22 | 18.5 | 67 | 11.6* | 26 |
| 9.5 | 33 | 12.7* | 17 | 10.0 | 45 |  |  | 12.7* | 35 |
| 10.5* | 18 | 16.7 | 26 | 12.1* | 24 |  |  | 14.0 | 15 |
| 19.1–19.6* | 32 | 18.3* | 27 | 14.8 | 17 |  |  | 16.7* | 30 |
|  |  | 19.5 | 23 | 16.0–16.5* | 20 |  |  | 18.9 | 86 |
|  |  | 20.1–20.4* | 37 | 17.5* | 28 |  |  | 20.8 | 94 |
|  |  | 21.2–21.9* | 32 | 19.0* | 46 |  |  | 23.6* | 38 |
|  |  | 22.9–23.3* | 38 | 19.5 | 65 |  |  | 25.5* | 32 |
|  |  | 24.4–25.0* | 35 | 20.2* | 47 |  |  |  |  |
|  |  |  |  | 21.3 | 64 |  |  |  |  |
|  |  |  |  | 21.6 | 55 |  |  |  |  |
|  |  |  |  | 22.0 | 45 |  |  |  |  |

* Broad
Forms XIV, XV, XVI, XVII, XVIII, and XIX were measured on Brucker D-5000 Diffractometer.
[a]Relative intensity for Form V 4.9 (broad) 2θ is 9; Form VI 13.8 2θ is 9; Form VIII 12.8 2θ is 6 and 13.8 2θ is 4; and Form XII 13.9 (broad) 2θ is 9 and 27.1 2θ is 8.

Because only 19 crystalline forms of atorvastatin are known, each form can be identified and distinguished from the other crystalline forms by either a combination of lines or a pattern that is different from the X-ray powder diffraction of the other forms.

For example, Table 2 lists combination of 2θ peaks for Forms V to XIX atorvastatin, i.e., a set of X-ray diffraction lines that are unique to each form. Forms I to IV atorvastatin disclosed in U.S. Pat. Nos. 5,969,156 and 6,121,461 are included for comparison.

TABLE 2

Forms I to XIX Unique Combination of 2θ Peaks

| Form I | Form II | Form III | Form IV | Form V | Form VI | Form VII | Form VIII | Form IX | Form X |
|---|---|---|---|---|---|---|---|---|---|
| 9.0 | 8.5 | 8.3 | 4.7 | 6.0 | 7.2 | 8.6 | 7.5 | 8.8 | 4.7 |
| 9.3 | 9.0 | 16.4 | 5.2 | 7.0 | 8.3 | 10.2 | 9.2 | 9.4* | 6.9 |
| 10.1 | 17.1–17.4 | 19.9 | 7.7 | 8.0* | 11.0 | 12.8* | 10.0 | 16.7 | 7.9 |
| 10.4 | 20.5 | 24.2 | 9.4 | 9.9 | 18.5 | 17.6 | 16.7* | 17.5* | 9.2 |
| 11.7 | | | 10.1 | 16.6 | | 18.3* | 18.6* | 19.3* | 9.5 |
| 12.0 | | | | | | 19.3 | 20.3* | 21.4* | 19.1 |
| 16.8 | | | | | | | | 29.0* | 19.8 |
| | | | | | | | | 30.0 | |

| Form XI | Form XII | Form XIII | Form XIV | Form XV | Form XVI | Form XVII | Form XVIII | Form XIX |
|---|---|---|---|---|---|---|---|---|
| 10.8* | 7.7 | 8.4 | 5.4 | 5.7 | 5.2 | 6.1 | 8.0 | 5.5 |
| 16.5 | 8.0 | 8.9 | 6.7 | 6.1 | 6.4 | 7.3 | 9.2* | 7.0 |
| 19.7 | 8.6 | 20.8* | 7.7 | 7.5 | 7.5 | 7.9 | 16.6* | 8.6 |
| 22.3 | 8.9 | 23.8* | 8.1 | 8.1 | 8.7 | 10.0 | 18.5 | 10.5 |
| | 9.9 | | 9.0 | 8.5 | 16.7 | 19.0* | | 12.7* |
| | 17.8 | | | 9.5 | 20.1–20.4* | 19.5 | | 18.9 |
| | 19.4 | | | 19.1–19.6* | 22.9–23.3* | 21.3 | | 20.8 |
| | | | | | | 21.6 | | |

*Broad
Forms I to XIII were measured on Shimadzu XRD-6000 diffractometer. Forms XIV to XIX were measured on Bruker D 50001 diffractometer. Form II 2θ peaks from U.S. Pat. No. 5,969,156.

Solid State Nuclear Magnetic Resonance (NMR)

Methodology

Solid-state $^{13}C$ NMR spectra were obtained at 270 or 360 MHz Tecmag instruments. High-power proton decoupling and cross-polarization with magic-angle spinning at approximately 4.7 and 4.2 kHz or 4.6 and 4.0 kHz were used for 68 MHz ($^{13}C$ frequency) data acquisition, 4.9 and 4.4 kHz were used for 91 MHz ($^{13}C$ frequency) data acquisition. The magic angle was adjusted using the Br signal of KBr by detecting the side bands. A sample was packed into a 7 mm Doty rotor and used for each experiment. The chemical shifts were referenced externally to adamantine except for Form X where the chemical shifts are arbitrary.

Table 3 shows the solid-state NMR spectrum for crystalline Forms V, VI, VII, VIII, and X atorvastatin.

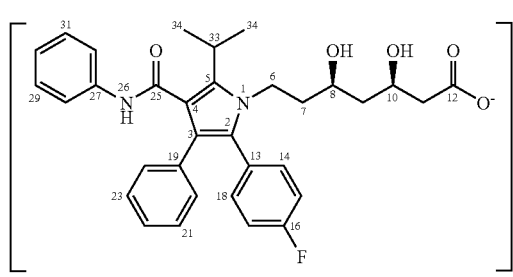

TABLE 3

Chemical Shifts for Forms V, VI, VII, VIII, and X Atorvastatin

| Chemical Shift | | | | |
|---|---|---|---|---|
| V | VI | VII | VIII | X |
| 185.7 | | 186.5 | 186.1 | 187.0 |
| | | 183.3 | 179.5 | |
| 176.8 | 176.5 | 176.8 | | 179.5 |
| 166.9 | 168.2 | 166.5 | 167.9 | 165.5 |
| | 163.1 | | 161.0 | |
| | 159.8 | 159.2 | | 159.4 |
| 138.7 | 136.8 | 137.6 | 139.4 | 137.9 |
| 136.3 | | | 132.9 | 134.8 |
| 133.0 | | | | |
| | | | | 129.4 |
| 128.4 | 127.8 | 128.3 | 128.7 | 127.9 |
| | | | 124.7 | 123.2 |
| 122.0 | 122.3 | 122.3 | | |
| | | | 121.8 | |
| | 118.8 | 119.2 | | 119.9 |
| 117.0 | | | | |
| 116.3 | | | 116.6 | |
| | 113.7 | | | |
| | 88.2 | 74.5 | | |
| | 79.3 | | | |
| | 70.5 | 70.3 | | 71.1 |
| 68.0 | | 68.3 | 67.0 | |
| | | 66.2 | | |
| 43.1 | 43.3 | 43.5 | 43.3 | 43.7 |
| | | 40.3 | | |
| | 36.9 | | | 40.9 |
| | 31.9 | | | |

TABLE 3-continued

Chemical Shifts for Forms V, VI, VII, VIII, and X Atorvastatin

Chemical Shift

| V | VI | VII | VIII | X |
|---|---|---|---|---|
| 25.6 | 25.9 | 26.3 | 26.7 | 26.4 |
|  | 24.9 | 24.7 |  | 25.3 |
|  | 22.5 | 20.2 | 20.9 | 20.3 |
| 19.9 |  |  | 20.1 |  |
|  |  |  |  | 18.3 |

Forms V, VI, VII, VIII, and X: Relative peak intensity over 20 are shown here (4.5, 4.6, 4.7, or 4.9 kHz CPMAS). Spectra were obtained using two different magic-angle spinning rates to determine spinning sidebands.
Form X: Relative peak intensity over 20 are shown here (5.0 kHz CPMAS).

Table 4 shows unique solid-state NMR peaks for Forms V, VI, VII, VIII and X atorvastatin, ie, peaks within ±1.0 ppm. Forms I to IV atorvastatin are included for comparison.

TABLE 4

Forms I to VIII and X Unique Solid-State NMR Peaks

| Form I | Form II | Form III | Form IV | Form V | Form VI | Form VII | Form VIII | Form X |
|---|---|---|---|---|---|---|---|---|
| 182.8 | 181.0 | 161.0 | 181.4 | 176.8 | 163.1 | 183.3 | 132.9 | 18.3 |
| 131.1 | 163.0 | 140.1 | 63.5 |  | 36.9 | 176.8 |  |  |
| 73.1 | 161.0 | 131.8 | 17.9 |  | 31.9 | 74.5 |  |  |
| 64.9 | 140.5 | 69.8 |  |  |  |  |  |  |
|  |  | 35.4 |  |  |  |  |  |  |

Raman Spectroscopy

Methodology

The Raman spectrum was obtained on a Raman accessory interfaced to a Nicolet Magna 860 Fourier transform infrared spectrometer. The accessory utilizes an excitation wavelength of 1064 nm and approximately 0.45 W of neodymium-doped yttrium aluminum garnet (Nd:YAG) laser power. The spectrum represents 64 or 128 co-added scans acquired at 4 cm$^{-1}$ resolution. The sample was prepared for analysis by placing a portion into a 5-mm diameter glass tube and positioning this tube in the spectrometer. The spectrometer was calibrated (wavelength) with sulfur and cyclohexane at the time of use.

Table 5 shows the Raman spectra for Forms V, VI, VII, VIII, X, and XII atorvastatin.

TABLE 5

Raman Peak Listing for Forms V, VI, VII, VIII, X and XII Atorvastatin

| Form V | Form VI | Form VII | Form VIII | Form X | Form XII |
|---|---|---|---|---|---|
| 3062 | 3058 | 3060 | 3065 | 3062 | 3064 |
|  |  |  |  |  | 2973 |
|  | 2935 | 2927 | 2923 | 2911 | 2926 |
| 1652 | 1651 | 1649 | 1658 | 1650 | 1652 |
| 1604 | 1603 | 1603 | 1603 | 1603 | 1603 |
| 1528 | 1556 | 1524 | 1531 | 1525 | 1527 |
|  | 1525 |  | 1510 |  |  |
|  |  |  | 1481 |  |  |
| 1478 | 1478 | 1476 |  | 1478 | 1470 |
| 1440 |  |  |  |  |  |
| 1413 | 1412 | 1412 | 1413 | 1411 | 1410 |
| 1397 |  | 1397 |  |  |  |
| 1368 |  | 1368 |  | 1369 | 1367 |
|  |  |  |  | 1240 | 1240 |
| 1158 | 1157 | 1159 |  | 1158 | 1159 |

TABLE 5-continued

Raman Peak Listing for Forms V, VI, VII, VIII, X and XII Atorvastatin

| Form V | Form VI | Form VII | Form VIII | Form X | Form XII |
|---|---|---|---|---|---|
| 1034 | | 1034 | | 1034 | 1034 |
| 1001 | 997 | 998 | 997 | 999 | 1002 |
| 825 | | 824 | | 824 | 823 |
| 245 | | | | | |
| 224 | | | | | |
| 130 | | | | | |
| | | 114 | 121 | 116 | |

Relative peak intensity over 20 are shown.

Table 6 lists unique Raman peaks for Forms V, VI, VII, VIII, X, and XII atorvastatin, ie, only one other form has a peak with ±4 cm$^{-1}$. In the case of Forms VI and X, it is a unique combination of peaks. Forms I to IV atorvastatin are included for comparison.

TABLE 6

Forms I to VIII, X and XII Unique Raman Peaks

| Form I | Form II | Form III | Form IV | Form V | Form VI* | Form VII | Form VIII | Form X* | Form XII |
|---|---|---|---|---|---|---|---|---|---|
| 3080 | 1663 | 2938 | 423 | 1440 | 3058 | 1397 | 1510 | 3062 | 2973 |
| 1512 | 359 | 1660 | 215 | 1397 | 2935 | | 1481 | 2911 | |
| 1439 | | 1510 | 132 | 130 | 1556 | | 1413 | 1525 | |
| 142 | | 1481 | | | 1525 | | 121 | 1240 | |
| | | 1427 | | | | | | | |
| | | 1182 | | | | | | | |
| | | 859 | | | | | | | |

*Unique combination of Raman peaks

Crystalline Forms V to XIX atorvastatin of the present invention may exist in anhydrous forms as well as hydrated and solvated forms. In general, the hydrated forms are equivalent to unhydrated forms and are intended to be encompassed within the scope of the present invention. Crystalline Form XIV contains about 6 mol of water. Preferably, Form XIV contains 6 mol of water. Crystalline Forms V, X, and XV atorvastatin contain about 3 mol of water. Preferably, Forms V, X, and XV atorvastatin contain 3 mol of water.

Crystalline Form VII contains about 1.5 mol of water. Preferably, Form VII atorvastatin contains 1.5 mol of water. Crystalline Form VIII contains about 2 mol of water. Preferably, Form VIII atorvastatin contains 2 mol of water.

Crystalline Forms XVI-XIX may exist as a solvate.

Crystalline forms of atorvastatin of the present invention, regardless of the extent of hydration and/or solvation having equivalent x-ray powder diffractograms, ssNMR, or Raman spectra are within the scope of the present invention.

Crystalline forms, in general, can have advantageous properties. A polymorph, solvate, or hydrate is defined by its crystal structure and properties. The crystal structure can be obtained from X-ray data or approximated from other data. The properties are determined by testing. The chemical formula and chemical structure does not describe or suggest the crystal structure of any particular polymorphic or crystalline hydrate form. One cannot ascertain any particular crystalline form from the chemical formula, nor does the chemical formula tell one how to identify any particular crystalline solid form or describe its properties. Whereas a chemical compound can exist in three states—solid, solution, and gas-crystalline solid forms exist only in the solid state. Once a chemical compound is dissolved or melted, the crystalline solid form is destroyed and no longer exists (Wells J. I., Aulton M. E. *Pharmaceutics. The 'Science of Dosage Form Design. Reformulation*, Aulton M. E. ed., Churchill Livingstone, 1988;13:237).

The new crystalline forms of atorvastatin described herein have advantageous properties. Form VII has good chemical stability, which is comparable to Form I (disclosed in U.S. Pat. No. 5,969,156). Since noncrystalline forms of atorvastatin are not chemically stable, this is a significant advantage, which would translate into enhanced shelf life and longer expiration dating. Form VII can be prepared from acetone/water, whereas Form I is prepared from the more toxic methanol/water system. Form VII is the sesquihydrate and contains less water, meaning that a unit weight of Form VII contains more atorvastatin molecules, meaning it is of higher potency.

The ability of a material to form good tablets at commercial scale depends upon a variety of drug physical properties, such as the Tableting Indices described in Hiestand H. and Smith D., Indices of Tableting Performance, *Powder Technology,* 1984;38:145–159. These indices may be used to identify forms of atorvastatin calcium which have superior tableting performance. One such index is the Brittle Fracture Index (BFI), which reflects brittleness, and ranges from 0 (good—low brittleness) to 1 (poor—high brittleness). For example, Form VII has a BFI value 0.09, while Form I has a BFI value 0.81. Thus, Form VII is less brittle than Form I. This lower brittleness indicates greater ease of manufacture of tablets.+

Form VIII also has less water than Form I (dihydrate vs trihydrate) and thus a gram of Form VIII contains more atorvastatin molecules.

Form X is advantageous in that it can be prepared from the less toxic isopropanol (IPA):water system, thus avoiding the more toxic methanol:water system.

Form XII has the highest melting point (210.6). Since high melting point correlates with stability at high temperature, this means this form is most stable at temperatures near the melting point. High melting forms can be advantageous when process methods involving high temperatures are used. Form XII is also prepared from the less toxic tetrahydrofuran (THF) water system.

Form XIV is prepared using the less toxic THF/water system.

The present invention provides a process for the preparation of crystalline Forms V to XIX atorvastatin which comprises crystallizing atorvastatin from a solution in solvents under conditions which yield crystalline Forms V to XIX atorvastatin.

The precise conditions under which crystalline Forms V to XIX atorvastatin are formed may be empirically determined, and it is only possible to give a number of methods which have been found to be suitable in practice.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either compounds or a corresponding pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from two or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.5 mg to 100 mg, preferably 2.5 mg to 80 mg according to the particular application and the potency of the active component. The composition can, if desired, also contain other compatible therapeutic agents.

In therapeutic use as hypolipidemic and/or hypocholesterolemic agents and agents to treat osteoporosis and Alzheimer's disease, the crystalline Forms V to XIX atorvastatin utilized in the pharmaceutical method of this invention are administered at the initial dosage of about 2.5 mg to about 80 mg daily. A daily dose range of about 2.5 mg to about 20 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

[R-(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid hemi calcium salt (Forms V–XIX atorvastatin)

Form V Atorvastatin

Method A

Amorphous atorvastatin calcium (U.S. Pat. No. 5,273,995) was slurried in a mixture of acetonitrile/water (9:1) to afford crystalline Form V atorvastatin.

Method B

Crystalline Form I atorvastatin calcium (U.S. Pat. No. 5,969,156) was slurried in a mixture of acetonitrile/water (9:1) at 60° C. overnight, filtered, and air dried to afford crystalline Form V atorvastatin.

Method C

Amorphous atorvastatin calcium (U.S. Pat. No. 5,273,995) was stressed under vapors of acetonitrile/water (9:1) to afford crystalline Form V atorvastatin.

Method D

Acetonitrile was added to a solution of amorphous atorvastatin calcium (U.S. Pat. No. 5,273,995) in tetrahydrofuran/water (9:1) and cooled to afford crystalline Form V atorvastatin.

Method E

Acetonitrile was added to a solution of amorphous atorvastatin calcium (U.S. Pat. No. 5,273,995) in dimethylformamide/water and fast evaporation affords crystalline Form V atorvastatin.

Method F

Amorphous atorvastatin calcium (U.S. Pat. No. 5,273,995) diffused in a vapor of acetonitrile/water (9:1) to afford crystalline Form V atorvastatin.

Crystalline Form V atorvastatin, mp 171.4° C., trihydrate Karl Fischer 4.88% (3 mol of water).

Form VI Atorvastatin

Method A

Amorphous atorvastatin calcium (U.S. Pat. No. 5,273,995) was placed into a vapor jar containing dimethylformamide/water (9:1) for 20 days to afford crystalline Form VI atorvastatin.

Method B

Fast evaporation of a dimethylformamide/water solution of amorphous atorvastatin calcium (U.S. Pat. No. 5,273,995) afforded crystalline Form VI atorvastatin.

Method C

Fast evaporation of a dimethylformamide/water (saturated) solution of amorphous atorvastatin calcium (U.S. Pat. No. 5,273,995) seeded with crystalline Form VI afforded crystalline Form VI atorvastatin.

Crystalline Form VI atorvastatin, mp 145.9° C.

Form VII Atorvastatin

Method A

A solution of amorphous atorvastatin calcium (U.S. Pat. No. 5,273,995) in acetone/water (1:1) (5.8 mg/mL) was stirred overnight. A solid formed which was filtered to afford crystalline Form VII atorvastatin.

Method B

A solution of amorphous atorvastatin calcium (U.S. Pat. No. 5,273,995) in acetone/water (1:1) was evaporated at 50° C. to afford crystalline Form VII atorvastatin.

Method C

A saturated solution of amorphous atorvastatin calcium (U.S. Pat. No. 5,273,995) in acetone/water (1:1) was seeded with crystalline Form VII atorvastatin to afford crystalline Form VII atorvastatin.

Method D

Fast evaporation of a saturated solution of amorphous atorvastatin calcium (U.S. Pat. No. 5,273,995) in acetone/water (1:1) was seeded with crystalline Form VII to afford crystalline Form VII atorvastatin.

Crystalline Form VII atorvastatin, mp 195.9° C., 1.5 hydrate Karl Fischer 2.34% (1.5 mol of water).

Form VIII Atorvastatin

Method A

A solution of amorphous atorvastatin calcium (U.S. Pat. No. 5,273,995) in dimethylformamide/water (saturated) (9:1), was seeded with crystalline Form VII and evaporated to afford crystalline Form VIII atorvastatin.

Method B

Fast evaporation of a solution of amorphous atorvastatin calcium (U.S. Pat. No. 5,273,995) in dimethylformamide/water (9:1) affords crystalline Form VIII atorvastatin.

Crystalline Form VIII atorvastatin, mp 151° C., dihydrate Karl Fischer 2.98% (2 mol of water).

Form IX Atorvastatin

Method A

A solution of amorphous atorvastatin calcium (U.S. Pat. No. 5,273,995) in acetone/water (6:4) (3.4 mg/mL) was evaporated on a rotary evaporator to afford crystalline Form IX atorvastatin.

Method B

A solution of amorphous atorvastatin calcium (U.S. Pat. No. 5,273,995) in acetone/water (6:4) was filtered, seeded with crystalline Form IX evaporated on a rotary evaporator to afford crystalline Form IX atorvastatin.

Method C

A solution of amorphous atorvastatin calcium (U.S. Pat. No. 5,273,995) in acetone/water (6:4) was stirred for 0.5 hours, filtered, evaporated on rotary evaporator to concentrate the solution, and dried in a vacuum oven to afford crystalline Form IX atorvastatin.

Form X Atorvastatin

Method A

A slurry of amorphous atorvastatin calcium (U.S. Pat. No. 5,273,995) in isopropanol/water (9:1) was stirred for a few days, filtered, and air dried to afford crystalline Form X atorvastatin.

Method B

A slurry of amorphous atorvastatin calcium (U.S. Pat. No. 5,273,995) in isopropanol/water (9:1) was stirred for 5 days, filtered, and air dried to afford crystalline Form X atorvastatin.

Method C

A saturated solution of amorphous atorvastatin calcium (U.S. Pat. No. 5,273,995) in isopropanol/water (9:1) was stirred for 2 days, filtered, and air dried to afford crystalline Form X atorvastatin.

Crystalline Form X atorvastatin, mp 180.1° C., trihydrate Karl Fischer 5.5% (3.5 mol of water).

Form XI Atorvastatin

A solution of amorphous atorvastatin calcium (U.S. Pat. No. 5,273,995) in acetonitrile/water (9:1) was filtered and allowed to evaporate slowly to afford crystalline Form XI atorvastatin.

Form XII Atorvastatin

Crystalline Form I atorvastatin calcium (U.S. Pat. No. 5,969,156) was slurried in tetrahydrofuran/water (2:8) at 90° C. for 5 days, filtered, and air dried to afford crystalline Form XII atorvastatin.

Crystalline Form XII atorvastatin, mp 210.6° C.

Form XIII Atorvastatin

Crystalline Form I atorvastatin calcium (U.S. Pat. No. 5,969,156) was added to 10 mL 2:8 water:methanol to leave a layer of solid on the bottom of a vial. The slurry was heated to about 70° C. for 5 days. The supernatant was removed, and the solid air dried to afford crystalline Form XIII atorvastatin.

Form XIV Atorvastatin

Amorphous atorvastatin calcium (U.S. Pat. No. 5,273,995), 1 g, was slurried for 3 weeks in 45 mL of isopropyl alcohol/5 mL of water (9:1) at ambient temperature. The mixture was filtered to afford crystalline Form XIV atorvastatin after drying at ambient temperature.

Differential scanning calorimetry (DSC) indicates a low desolvation event at about 60° C. (peak) followed by a melt at about 150° C. Combustion analysis indicates that the compound is a hexahydrate. Thermographic infrared spectroscopy (TG-1R) shows the compound contains water. Karl Fischer shows the compound contains 5.8% water.

Form XV Atorvastatin

Amorphous atorvastatin calcium (U.S. Pat. No. 5,273,995), 1 g, was slurried for 3 weeks in 45 mL acetonitrile/5 mL of water (9:1) at ambient temperature. The mixture was filtered to afford crystalline Form XV atorvastatin after drying at ambient temperature. DSC indicates a low desolvation event at about 78° C. (peak) followed by a melt at about 165° C. Combustion analysis indicates that the compound is a trihydrate. TG-1R shows the compound contains water.

Form XVI Atorvastatin

Amorphous atorvastatin calcium (U.S. Pat. No. 5,273,995), 1 g, was slurried for about 1 day in 9:1 acetonitrile/water at room temperature. The mixture was filtered to afford crystalline Form XVI atorvastatin after drying at ambient temperature. DSC indicates a broad endotherm at peak temperature of 72° C. and an endotherm with onset temperature of 164° C. The weight loss profile by thermographic analysis (TGA) indicates a total weight loss of about 7% at 30° C. to 160° C. Combustion analysis indicates that TGA and Karl Fischer analysis (shows 7.1% water) indicates the compound is a tetrahydrate/acetonitrile solvate.

Form XVII Atorvastatin

Amorphous atorvastatin calcium (U.S. Pat. No. 5,273,995), 0.5 g, was slurried for about 2 days in 5 mL of 9:1 dimethylformamide (DMF)/water containing 25 mL of acetonitrile at room temperature. The mixture was filtered to afford crystalline Form XVII atorvastatin after drying at ambient temperature. DSC showed multiple broad endotherms indicating the compound was a solvate.

Form XVIII Atorvastatin

Crystalline Form XVI atorvastatin, 0.5 g, was dried for about 1 day at room temperature to afford crystalline Form XVIII atorvastatin. DSC showed a broad endotherm at low temperature indicating the compound was a solvate. Karl Fischer analysis showed the compound contained 4.4% water.

Form XIX Atorvastatin

Amorphous atorvastatin calcium (U.S. Pat. No. 5,273,995), 0.4 g, was slurried for about 7 days in 4 mL methyl ethyl ketone at room temperature. The mixture was filtered to afford crystalline Form XIX atorvastatin after drying at ambient temperature. DSC indicated a low desolvation event at about 50° C. (peak) followed by a melt at about 125° C. TGA analysis indicates that the compound is a solvate that desolvates at low temperature.

What is claimed is:

1. A solid pharmaceutical composition comprising crystalline Form V atorvastatin or a hydrate thereof having an X-ray powder diffraction containing the following 2θ values measured using $CuK_\alpha$ radiation: 4.9 (broad). 6.0, 7.0, 8.0 (broad), 8.6, 9.9, 16.6, 19.0, and 21.1, and at least one pharmaceutically acceptable excipient, diluent or carrier.

2. A solid pharmaceutical composition comprising crystalline Form VI atorvastatin or a hydrate thereof having an X-ray powder diffraction containing the following 2θ values measured using $CuK_\alpha$ radiation: 7.2, 8.3, 11.0, 12.4. 13.8, 16.8, 18.5, 19.7 (broad), 20.9, and 25.0 (broad), and at least one pharmaceutically acceptable excipient, diluent or carrier.

3. A solid pharmaceutical composition comprising crystalline Form VII atorvastatin or a hydrate thereof having an X-ray powder diffraction containing the following 2θ values measured using $CuK_\alpha$ radiation: 8.6, 10.2, 12.4 (broad), 12.8 (broad), 17.6, 18.3 (broad), 19.3, 22.2 (broad), 23.4 (broad), 23.8 (broad), and 25.5 (broad), and at least one pharmaceutically acceptable excipient, diluent or carrier.

4. A solid pharmaceutical composition comprising crystalline Form VIII atorvastatin or a hydrate thereof having an X-ray powder diffraction containing the following 2θ values measured using $CuK_\alpha$ radiation: 7.5, 9.2, 10.0, 12.1, 12.8, 13.8, 15.1, 16.7 (broad), 18.6 (broad), 20.3 (broad), 21.2, 21.9, 22.4, 25.8, 26.5, 27.4 (broad) and 30.5, and at least one pharmaceutically acceptable excipient, diluent or carrier.

5. A solid pharmaceutical composition comprising crystalline Form IX atorvastatin or a hydrate thereof having an X-ray powder diffraction containing the following 2θ values measured using $CuK_\alpha$ radiation: 8.8, 9.4 (broad), 11.2–11.7 (broad), 16.7, 17.5 (broad), 19.3, 21.4 (broad), 22.4 (broad), 23.2 (broad), and 29.0 (broad), and at least one pharmaceutically acceptable excipient, diluent or carrier.

6. A solid pharmaceutical composition comprising crystalline Form XI atorvastatin or a hydrate thereof having an X-ray powder diffraction containing the following 2θ values measured using $CuK_\alpha$ radiation: 10.8 (broad), 12.0, 13.5, 16.5, 17.6–18.0 (broad), 19.7, 22.3, 23.2, 24.4, 25.8, 26.5, 27.3, 28.7, 29.5, 30.9 (broad), 32.8 (broad), 33.6 (broad), 36.0 (broad) and 38.5 (broad), and at least one pharmaceutically acceptable excipient, diluent or carrier.

7. A solid pharmaceutical composition comprising crystalline Form XII atorvastatin or a hydrate thereof having an X-ray powder diffraction containing the following 2θ values measured using $CuK_\alpha$ radiation: 5.4, 7.7, 8.0, 8.6, 8.9, 9.9, 10.4 (broad), 12.5, 13.9 (broad), 16.2, 17.8, 19.4, 20.8, 21.7, 22.4–22.6 (broad), 24.3, 25.5, 26.2, and 27.1, and at least one pharmaceutically acceptable excipient, diluent or carrier.

8. A solid pharmaceutical composition comprising crystalline Form XIII atorvastatin or a hydrate thereof having an X-ray powder diffraction containing the following 2θ values measured using $CuK_\alpha$ radiation: 8.4, 8.9, 15.7 (broad), 16.4 (broad), 17.6 (broad), 18.1 (broad), 19.7 (broad), 20.8 (broad), and 23.8 (broad), and at least one pharmaceutically acceptable excipient, diluent or carrier.

9. A solid pharmaceutical composition comprising crystalline Form XIV atorvastatin or a hydrate thereof having an X-ray powder diffraction containing the following 2θ values measured using $CuK_\alpha$ radiation: 5.4, 6.7, 7.7, 8.1, 9.0, 16.5 (broad), 17.6 (broad), 18.0–18.7 (broad), and 19.5 (broad), and at least one pharmaceutically acceptable excipient, diluent or carrier.

10. A solid pharmaceutical composition comprising crystalline Form XV atorvastatin or a hydrate thereof having an X-ray powder diffraction containing the following 2θ values measured using $CuK_\alpha$ radiation: 5.7, 6.1, 6.8, 7.5, 8.1, 8.5, 9.5, 10.5 (broad), and 19.1–19.6 (broad), and at least one pharmaceutically acceptable excipient, diluent or carrier.

11. A solid pharmaceutical composition comprising crystalline Form XVI atorvastatin or a hydrate thereof having an X-ray powder diffraction containing the following 2θ values measured using CuK$_\alpha$ radiation: 5.2, 6.4, 7.5, 8.7, 10.5 (broad), 12.0 (broad), 12.7 (broad), 16.7, 18.3 (broad), 19.5, 20.1–20.4 (broad), 21.2–21.9 (broad), 22.9–23.3 (broad), and 24.4–25.0 (broad), and at least one pharmaceutically acceptable excipient, diluent or carrier.

12. A solid pharmaceutical composition comprising crystalline Form XVII atorvastatin or a hydrate thereof having an X-ray powder diffraction containing the following 2θ values measured using CuK$_\alpha$ radiation 5.0, 6.1, 7.3, 7.9, 8.5, 9.1, 10.0, 12.1 (broad), 14.8, 16.0–16.5 (broad), 17.5 (broad), 19.0 (broad), 19.5, 20.2 (broad), 21.3, 21.6, and 22.0, and at least one pharmaceutically acceptable excipient, diluent or carrier.

13. A solid pharmaceutical composition comprising crystalline Form XVIII atorvastatin or a hydrate thereof having an X-ray powder diffraction containing the following 2θ values measured using CuK$_\alpha$ radiation: 8.0, 9.2 (broad), 9.7 (broad), 12.1, 16.6 (broad), and 18.5, and at least one pharmaceutically acceptable excipient, diluent or carrier.

14. A solid pharmaceutical composition comprising crystalline Form XIX atorvastatin or a hydrate thereof having an X-ray powder diffraction containing the following 2θ values measured using CuK$_\alpha$ radiation: 5.2, 6.3, 7.0, 8.6, 10.5, 11,6 (broad), 12.7 (broad), 14.0, 16.7 (broad), 18.9, 20.8, 23.6 (broad), and 25.5 (broad), and at least one pharmaceutically acceptable excipient, diluent or carrier.

15. 9newA solid pharmaceutical composition comprising crystalline Form V atorvastatin or a hydrate thereof characterized by solid state $^{13}$C nuclear magnetic resonance having the following chemical shifts expressed in parts per million: 19.9, 25.6, 43.1, 68.0, 116.3, 117.0. 122.0, 128.4, 133.0, 136.3, 138.7, 166.9, 176.8, and 185.7, and at least one pharmaceutically acceptable excipient, diluent or carrier.

16. A solid pharmaceutical composition comprising crystalline Form VI atorvastatin or a hydrate thereof characterized by solid state $^{13}$C nuclear magnetic resonance having the following chemical shifts expressed in parts per million: 22.5, 25.9, 31.9, 36.9, 43.3, 70.5, 79.3, 88.2, 113.7, 118.8, 122.3, 127.8, 136.8, 159.8, 163.1, 168.2, and 176.5, and at least one pharmaceutically acceptable excipient, diluent or carrier.

17. A solid pharmaceutical composition comprising crystalline Form VII atorvastatin or a hydrate thereof characterized by solid state $^{13}$C nuclear magnetic resonance having the following chemical shifts expressed in parts per million: 20.2, 24.9, 26.3, 40.3, 43.5, 66.2, 68.3, 70.3, 74.5, 119.2, 122.3, 128.3, 137.6, 159.2, 166.5, 176.8, 183.3, and 186.5, and at least one pharmaceutically acceptable excipient, diluent or carrier.

18. A solid pharmaceutical composition comprising crystalline Form VIII atorvastatin or a hydrate thereof characterized by solid state $^{13}$C nuclear magnetic resonance having the following chemical shifts expressed in parts per million: 20.1, 20.9, 24.7, 26.7, 43.3, 67.0, 116.6, 121.8, 124.7, 128.7, 132.9, 139.4, 161.0, 167.9, 179.5, and 186.1, and at least one pharmaceutically acceptable excipient, diluent or carrier.

19. A solid pharmaceutical composition comprising crystalline Form V atorvastatin or a hydrate thereof characterized by Raman spectroscopy having the following peaks expressed in cm$^{-1}$: 130, 224, 245, 825, 1001, 1034, 1158, 1368, 1397, 1413, 1440, 1478, 1528, 1604, 1652, and 3062 and at least one pharmaceutically acceptable excipient, diluent or carrier.

20. A solid pharmaceutical composition comprising crystalline Form VI atorvastatin or a hydrate thereof characterized by Raman spectroscopy having the following peaks expressed in cm$^{-1}$: 997, 1157, 1412, 1478, 1525, 1556, 1603, 1651, 2935, and 3058 and at least one pharmaceutically acceptable excipient, diluent or carrier.

21. A solid pharmaceutical composition comprising crystalline Form VII atorvastatin or a hydrate thereof characterized by Raman spectroscopy having the following peaks expressed in cm$^{-1}$: 114, 824, 998, 1034, 1159, 1368, 1397, 1412, 1476, 1524, 1603, 1649, 2927, and 3060 and at least one pharmaceutically acceptable excipient, diluent or carrier.

22. A solid pharmaceutical composition comprising crystalline Form VIII atorvastatin or a hydrate thereof characterized by Raman spectroscopy having the following peaks expressed in cm$^{-1}$: 121, 997, 1413, 1481, 1510, 1531, 1603, 1658, 2923, and 3065 and at least one pharmaceutically acceptable excipient, diluent or carrier.

23. A solid pharmaceutical composition comprising crystalline Form XII atorvastatin or a hydrate thereof characterized by Raman spectroscopy having the following peaks expressed in cm$^{-1}$: 823, 1002, 1034, 1159, 1240, 1367, 1410, 1470, 1527, 1603, 1652, 2926, 2973, and 3064 and at least one pharmaceutically acceptable excipient, diluent or carrier.

24. A method of treating hyperlipidemia, hypercholesterolemia, osteoporosis or Alzheimer's Disease comprising administering to a host suffering therefrom a therapeutically effective amount of crystalline Form V atorvastatin or a hydrate thereof having an X-ray powder diffraction containing the following 2θ values measured using CuK$_\alpha$ radiation: 4.9 (broad), 6.0, 7.0, 8.0 (broad), 8.6, 9.9, 16.6, 19.0, and 21.1, in solid unit dosage form.

25. A method of treating hyperlipidemia, hypercholesterolemia, osteoporosis or Alzheimer's disease comprising administering to a host suffering therefrom a therapeutically effective amount of crystalline Form VI atorvastatin or a hydrate thereof having an X-ray powder diffraction containing the following 2θ values measured using CuK$_\alpha$ radiation: 7.2, 8.3, 11.0, 12.4, 13.8, 16.8, 18.5, 19.1 (broad), 20.9, and 25.0 (broad), in solid unit dosage form.

26. A method of treating hyperlipidemia, hypercholesterolemia, osteoporosis or Alzheimer's disease comprising administering to a host suffering therefrom a therapeutically effective amount of crystalline Form VII atorvastatin or a hydrate thereof having an X-ray powder diffraction containing the following 2θ values measured using CuK$_\alpha$ radiation: 8.6, 10.2, 12.4 (broad), 12.8 (broad), 17.6, 18.3 (broad), 19.3, 22.2 (broad), 23.4 (broad), 23.8 (broad), and 25.5 (broad), in solid unit dosage form.

27. A method of treating hyperlipidemia, hypercholesterolemia, osteoporosis or Alzheimer's disease comprising administering to a host suffering therefrom a therapeutically effective amount of crystalline Form VIII atorvastatin or a hydrate thereof having an X-ray powder diffraction containing the following 2θ values measured using CuK$_\alpha$ radiation: 7.5, 9.2, 10.0, 12.1, 12.8, 13.8, 15.1, 16.7 (broad), 18.6 (broad), 20.3 (broad), 21.2, 21.9, 22.4, 25.8, 26.5, 27.4 (broad), and 30.5, in solid unit dosage form.

28. A method of treating hyperlipidemia, hypercholesterolemia, osteoporosis or Alzheimer's disease comprising administering to a host suffering therefrom a therapeutically effective amount of crystalline Form IX atorvastatin or a hydrate thereof having an X-ray powder diffraction containing the following 2θ values measured using CuK$_\alpha$ radiation: 8.8, 9.4 (broad), 11.2–11.7 (broad), 16.7, 17.5 (broad), 19.3

(broad), 21.4 (broad), 22.4 (broad), 23.2 (broad), and 29.0 (broad), in solid unit dosage form.

29. A method of treating hyperlipidemia, hypercholesterolemia, osteoporosis or Alzheimer's disease comprising administering to a host suffering therefrom a therapeutically effective amount of crystalline Form XI atorvastatin or a hydrate thereof having an X-ray powder diffraction containing the following 2θ values measured using CuK$_\alpha$ radiation: 10.8 (broad), 12.0, 13.5, 16.5, 17.6–18.0 (broad), 19.7, 22.3, 23.2, 24.4, 25.8, 26.5, 27.3, 28.7, 29.5, 30.9 (broad), 32.8 (broad), 33.6 (broad), 36.0 (broad), and 38.5 (broad), in solid unit dosage form.

30. A method of treating hyperlipidemia, hypercholesterolemia, osteoporosis or Alzheimer's disease comprising administering to a host suffering therefrom a therapeutically effective amount of crystalline Form XII atorvastatin or a hydrate thereof having an X-ray powder diffraction containing the following 2θ values measured using CuK$_\alpha$ radiation: 5.4, 7.7, 8.0, 8.6, 8.9, 9.9, 10.4 (broad), 12.5, 13.9 (broad), 16.2, 17.8, 19.4, 20.8, 21.7, 22.4–22.6 (broad), 24.3, 25.5, 26.2, and 27.1, in solid unit dosage form.

31. A method of treating hyperlipidemia, hypercholesterolemia, osteoporosis or Alzheimer's disease comprising administering to a host suffering therefrom a therapeutically effective amount of crystalline Form XIII atorvastatin or a hydrate thereof having an X-ray powder diffraction containing the following 2θ values measured using CuK$_\alpha$ radiation: 8.4, 8.9, 15.7 (broad), 16.4 (broad), 17.6 (broad), 18.1 (broad), 19.7 (broad), 20.8 (broad), and 23.8 (broad), in solid unit dosage form.

32. A method of treating hyperlipidemia, hypercholesterolemia, osteoporosis or Alzheimer's disease comprising administering to a host suffering therefrom a therapeutically effective amount of crystalline Form XIV atorvastatin or a hydrate thereof having an X-ray powder diffraction containing the following 2θ values measured using CuK$_\alpha$ radiation: 5.4, 6.7, 7.7, 8.1, 9.0, 16.5 (broad), 17.6 (broad), 18.0–18.7 (broad), and 19.5 (broad), in solid unit dosage form.

33. A method of treating hyperlipidemia, hypercholesterolemia, osteoporosis or Alzheimer's disease comprising administering to a host suffering therefrom a therapeutically effective amount of crystalline Form XV atorvastatin or a hydrate thereof having an X-ray powder diffraction containing the following 2θ values measured using CuK$_\alpha$ radiation: 5.7, 6.1, 6.8, 7.5, 8.1, 8.5, 9.5, 10.5 (broad), and 19.1–19.6 (broad), in solid unit dosage form.

34. A method of treating hyperlipidemia, hypercholesterolemia, osteoporosis or Alzheimer's disease comprising administering to a host suffering therefrom a therapeutically effective amount of crystalline Form XVI atorvastatin or a hydrate thereof having an X-ray powder diffraction containing the following 2θ values measured using CuK$_{\alpha\ radiation}$: 5.2, 6.4, 7.5, 8.7, 10.5 (broad), 12.0 (broad), 12.7 (broad), 16.7, 18.3 (broad), 19.5, 20.1–20.4 (broad), 21.2–21.9 (broad), 22.9–23.3 (broad), and 24.4–25.0 (broad), in solid unit dosage form.

35. A method of treating hyperlipidemia, hypercholesterolemia, osteoporosis or Alzheimer's disease comprising administering to a host suffering therefrom a therapeutically effective amount of crystalline Form XVII atorvastatin or a hydrate thereof having an X-ray powder diffraction containing the following 2θ values measured using CuK$_\alpha$ radiation: 5.0, 6.1, 7.3, 7.9, 8.5, 9.1, 10.0, 12.1 (broad), 14.8, 16.0–16.5 (broad), 17.5 (broad), 19.0 (broad), 19.5, 20.2 (broad), 21.3, 21.6, and 22.0, in solid unit dosage form.

36. A method of creating hyperlipidemia, hypercholesterolemia, osteoporosis or Alzheimer's disease comprising administering to a host suffering therefrom a therapeutically effective amount of crystalline Form XVIII atorvastatin or a hydrate thereof having an X-ray powder diffraction containing the following 2θ values measured using CuK$_\alpha$ radiation: 8.0, 9.2 (broad), 9.7 (broad), 12.1, 16.6 (broad), and 18.5, in solid unit dosage form.

37. A method of treating hyperlipidemia, hypercholesterolemia, osteoporosis or Alzheimer's disease comprising administering to a host suffering therefrom a therapeutically effective amount of crystalline Form XIX atorvastatin or a hydrate thereof having an X-ray powder diffraction containing the following 2θ values measured using CuK$_\alpha$ radiation: 5.2, 6.3, 7.0, 8.6, 10.5, 11.6 (broad), 12.7 (broad), 14.0, 16.7 (broad), 18.9, 20.8, 23.6 (broad), and 25.5 (broad), in solid unit dosage form.

38. A method of treating hyperlipidemia, hypercholesterolemia, osteoporosis or Alzheimer's disease comprising administering to a host suffering therefrom a therapeutically effective amount of crystalline Form V atorvastatin or a hydrate thereof characterized by solid state $^{13}$C nuclear magnetic resonance having the following chemical shifts expressed in parts per million: 19.9, 25.6, 43.1, 68.0, 116.3, 117.0, 122.0, 128.4, 133.0, 136.3, 138.7, 166.9, 176.8, and 185.7, in solid unit dosage form.

39. A method of treating hyperlipidemia, hypercholesterolemia, osteoporosis or Alzheimer's disease comprising administering to a host suffering therefrom a therapeutically effective amount of crystalline Form VI atorvastatin or a hydrate thereof characterized by solid state $^{13}$C nuclear magnetic resonance having the following chemical shifts expressed in parts per million: 22.5, 25.9, 31.9, 36.9, 43.3, 70.5, 79.3, 88.2, 113.7, 118.8, 122.3, 127.8, 136.8, 159.8, 163.1, 168.2, and 176.5, in solid unit dosage form.

40. A method of treating hyperlipidemia, hypercholesterolemia, osteoporosis or Alzheimer's disease comprising administering to a host suffering therefrom a therapeutically effective amount of crystalline Form VII atorvastatin or a hydrate thereof characterized by solid state $^{13}$C nuclear magnetic resonance having the following chemical shifts expressed in parts per million: 20.2, 24.9, 26.3, 40.3, 43.5, 66.2, 68.3, 70.3, 74.5, 119.2, 122.3, 128.3, 137.6, 159.2, 166.5, 176.8, 183.3, and 186.5, in solid unit dosage form.

41. A method of treating hyperlipidemia, hypercholesterolemia, osteoporosis or Alzheimer's disease comprising administering to a host suffering therefrom a therapeutically effective amount of crystalline Form VIII atorvastatin or a hydrate thereof characterized by solid state $^{13}$C nuclear magnetic resonance having the following chemical shifts expressed in parts per million: 20.1, 20.9, 24.7, 26.7, 43.3, 67.0 116.6, 121.8, 124.7, 128.7, 132.9, 139.4, 161.0, 167.9, 179.5, and 186.1, in solid unit dosage form.

42. A method of treating hyperlipidemia, hypercholesterolemia, osteoporosis or Alzheimer's disease comprising administering to a host suffering therefrom a therapeutically effective amount of crystalline Form V atorvastatin or a hydrate thereof characterized by Raman spectroscopy having the following peaks expressed in cm$^{-1}$: 130, 224, 245, 825, 1001, 1034, 1158, 1368, 1397, 1413, 1440, 1478, 1528, 1604, 1652, and 3062, in solid unit dosage form.

43. A method of treating hyperlipidemia, hypercholesterolemia, osteoporosis or Alzheimer's disease comprising administering to a host suffering therefrom a therapeutically effective amount of crystalline Form VI atorvastatin or a hydrate thereof characterized by Raman spectroscopy having the following peaks expressed in cm$^{-1}$: 997, 1157, 1412, 1478, 1525, 1556, 1603, 1651, 2935, and 3058, in solid unit dosage form.

44. A method of treating hyperlipidemia, hypercholesterolemia, osteoporosis or Alzheimer's disease comprising administering to a host suffering therefrom a therapeutically effective amount of crystalline Form VII atorvastatin or a hydrate thereof characterized by Raman spectroscopy having the following peaks expressed in cm$^{-1}$: 114, 824, 998, 1034, 1159, 1368, 1397, 1412, 1476, 1524, 1603, 1649, 2927, and 3060, in solid unit dosage form.

45. A method of treating hyperlipidemia, hypercholesterolemia, osteoporosis or Alzheimer's disease comprising administering to a host suffering therefrom a therapeutically effective amount of crystalline Form VIII atorvastatin or a hydrate thereof characterized by Raman spectroscopy having the following peaks expressed in cm$^{-1}$: 121, 997, 1413, 1481, 1510, 1531, 1603, 1658, 2923, and 3065, in solid unit dosage form.

46. A method of treating hyperlipidemia, hypercholesterolemia, osteoporosis or Alzheimer's disease comprising administering to a host suffering therefrom a therapeutically effective amount of crystalline Form XII atorvastatin or a hydrate thereof characterized by Raman spectroscopy having the following peaks expressed in cm$^{-1}$: 823, 1002, 1034, 1159, 1240, 1367, 1410, 1470, 1527, 1603, 1652, 2926, 2973, and 3064, in solid unit dosage form.

* * * * *